US009970001B2

(12) United States Patent
Miller

(10) Patent No.: US 9,970,001 B2
(45) Date of Patent: May 15, 2018

(54) METHODS AND COMPOSITIONS FOR NUCLEASE DESIGN

(71) Applicant: Sangamo BioSciences, Inc., Richmond, CA (US)

(72) Inventor: Jeffrey C. Miller, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 260 days.

(21) Appl. No.: 14/731,821

(22) Filed: Jun. 5, 2015

(65) Prior Publication Data

US 2015/0353917 A1 Dec. 10, 2015

Related U.S. Application Data

(60) Provisional application No. 62/008,359, filed on Jun. 5, 2014.

(51) Int. Cl.
| | | |
|---|---|---|
| C12N 15/01 | (2006.01) | |
| C12N 15/113 | (2010.01) | |
| C12N 15/63 | (2006.01) | |
| C12N 9/22 | (2006.01) | |
| C12N 15/10 | (2006.01) | |

(52) U.S. Cl.
CPC .............. *C12N 15/01* (2013.01); *C12N 9/22* (2013.01); *C12N 15/102* (2013.01); *C12N 15/63* (2013.01); *C07K 2319/00* (2013.01); *C12Y 301/00* (2013.01)

(58) Field of Classification Search
CPC combination set(s) only.
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas et al. | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,503,717 B2 | 1/2003 | Case et al. | |
| 6,534,261 B1 | 3/2003 | Cox et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,824,978 B1 | 11/2004 | Cox, III et al. | |
| 6,933,113 B2 | 8/2005 | Case et al. | |
| 6,936,243 B2 | 8/2005 | Snyder et al. | |
| 6,979,539 B2 | 12/2005 | Cox et al. | |
| 7,013,219 B2 | 3/2006 | Case et al. | |
| 7,067,317 B2 | 6/2006 | Rebar et al. | |
| 7,074,596 B2 | 7/2006 | Darzynkiewicz et al. | |
| 7,163,824 B2 | 1/2007 | Cox, III et al. | |
| 7,262,054 B2 | 8/2007 | Jamieson et al. | |
| 7,888,121 B2 | 2/2011 | Urnov et al. | |
| 7,914,796 B2 | 3/2011 | Miller et al. | |
| 7,951,925 B2 | 5/2011 | Ando et al. | |
| 7,972,854 B2 | 7/2011 | Miller et al. | |
| 8,034,598 B2 | 10/2011 | Miller | |
| 8,110,379 B2 | 2/2012 | DeKelver et al. | |
| 8,153,773 B2 | 4/2012 | Jemielity et al. | |
| 8,329,986 B2 | 12/2012 | Butler et al. | |
| 8,409,861 B2 | 4/2013 | Guschin et al. | |
| 8,563,314 B2 | 10/2013 | Gregory et al. | |
| 8,586,526 B2 | 11/2013 | Gregory et al. | |
| 8,623,618 B2 | 1/2014 | Doyon et al. | |
| 8,697,359 B1 | 4/2014 | Zhang | |
| 2003/0232410 A1 | 12/2003 | Liljedahl et al. | |
| 2005/0026157 A1 | 2/2005 | Baltimore et al. | |
| 2005/0064474 A1 | 3/2005 | Urnov et al. | |
| 2005/0208489 A1 | 12/2005 | Carroll et al. | |
| 2006/0063231 A1 | 3/2006 | Li et al. | |
| 2007/0218528 A1 | 9/2007 | Miller | |
| 2008/0131962 A1 | 6/2008 | Miller | |
| 2008/0159996 A1 | 7/2008 | Ando et al. | |
| 2008/0299580 A1 | 12/2008 | DeKelver et al. | |
| 2008/0299590 A1 | 12/2008 | Frackelton, Jr. | |
| 2009/0068164 A1 | 3/2009 | Segal et al. | |
| 2010/0047805 A1 | 2/2010 | Wang et al. | |
| 2010/0218264 A1 | 8/2010 | Cui et al. | |
| 2011/0082093 A1 | 4/2011 | Gregory et al. | |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Feng Zhang et al (Multiplex Genome Engineering Using CRISPR/Cas Systems. Jan. 3, 2013 Science Feb. 15, 2013: vol. 339 No. 6121 pp. 819-823.*
Anders, et al., "Structural Basis of Pam-Dependent Target DNA Recognition by the Cas9 Endonuclease," *Nature* 513:569-573 (2014) doi:10.1038/nature13579.
Bateman and Haft, "HMM-Based Databases in Interpro," *Breifings Bioinformatics* 3(3):236-245 (2002).
Bauer, et al., "An Erythroid Enhancer of BCL11A Subject to Genetic Variation Determines Fetal Hemoglobin Level," *Science* 342(6155):253-257 (2013).
Bendle, et al., "Lethal Graft-Versus-Host Disease in Mouse Models of T Cell Receptor Gene Therapy," *Nature Medicine* 16:565-570 (2010).
Brouns, et al., "Small Crispr RNAs Guide Antiviral Defense in Prokaryotes," *Science* 321:960-964 (2008).

(Continued)

*Primary Examiner* — Kagnew H Gebreyesus
(74) *Attorney, Agent, or Firm* — Pasternak Patent Law; Susan Abrahamson

(57) ABSTRACT

Methods and compositions for genetic alteration of cells are provided.

10 Claims, No Drawings

(56) References Cited

U.S. PATENT DOCUMENTS

| | | |
|---|---|---|
| 2011/0201055 A1 | 8/2011 | Doyon et al. |
| 2011/0207221 A1 | 8/2011 | Cost et al. |
| 2011/0265198 A1 | 10/2011 | Gregory et al. |
| 2012/0017290 A1 | 1/2012 | Cui et al. |
| 2012/0093787 A1 | 4/2012 | Holmes et al. |
| 2012/0192301 A1 | 7/2012 | Jaenisch et al. |
| 2012/0195936 A1 | 8/2012 | Rudolph et al. |
| 2012/0214241 A1 | 8/2012 | Laganiere |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar et al. |
| 2013/0253040 A1 | 9/2013 | Miller et al. |
| 2014/0068797 A1 | 3/2014 | Doudna et al. |
| 2014/0120612 A1 | 5/2014 | Doyon et al. |
| 2014/0140969 A1 | 5/2014 | Beausejour et al. |
| 2014/0335063 A1 | 11/2014 | Cannon et al. |
| 2015/0056705 A1 | 2/2015 | Conway et al. |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 14/018423 A2 | 3/2014 |
| WO | WO 14/065596 A1 | 5/2014 |
| WO | 2014089290 A1 | 6/2014 |
| WO | 2014150624 A1 | 9/2014 |
| WO | 2014186585 A2 | 11/2014 |
| WO | 2014191521 A2 | 12/2014 |
| WO | 2015021426 A1 | 2/2015 |
| WO | 2015134812 A1 | 9/2015 |
| WO | 2016106338 A2 | 6/2016 |
| WO | 2016141224 A1 | 9/2016 |

OTHER PUBLICATIONS

Chui, et al., "Hemoglobin H Disease: Not Necessarily a Benign Order," *Blood* 101(3):791 (2003).

Cong, et al., "Multiplex Genome Engineering Using CRISPR/Cas Systems," Sciencexpress/10.1126/science.1231143 (2013).

Esvelt, et al., "Orthogonal Cas9 Proteins for RNA-Guided Gene Regulation and Editing," *Nat. Methods* 10(11): doi:10.1038/nmeth. 2681.

Fonfara, et al., "Phylogeny of Cas9 Determines Functional Exchangeability of Dual-RNA and Cas9 Among Orthologous Type II CRISPR-Cas Systems," *Nuc. Acids Research* 42(4):2377-2590 (2013).

Fu, et al., "Improving CRISPR-Cas Nuclease Specificity Using Truncated Guide RNAs," *Nature Biotech.* 32(3):279-284 (2014).

Godde and Bickerton, "The Repetitive DNA Elements Called CRISPRs and Their Associated Genes: Evidence of Horizontal Transfer Among Prokaryotes," *J. Mol. Evol.* 62:718-729 (2006).

Graham, et al., "Performance of AAV8 Vectors Expressing Human Factor IX From a Hepatic-Selective Promoter Following Intravenous Injection Into Rats," *Genet. Vaccines Ther.* 3:6-9 (2008) doi: 10.1186/1479-0556-6-9.

Guilinger, et al., "Fusion of Catalytically Inactive Cas9 to FOKL Nuclease Improves the Specificity of Genome Modification," *Nat. Biotechnol.* 32(6):577-582 (2014).

Guo, et al., "Directed Evolution of an Enhanced and Highly Efficient FOKI Cleavage Domain for Zinc Finger Nucleases," *J. Mol. Biol.* (2010) doi:10.101b/jjmb.2010.04.060.

Guschin, et al., "A Rapid and General Assay for Monitoring Endogenous Gene Modification," *Methods Mol. Biol.* 649:247-256 (2010).

Haft, et al., "The TIGRFAMS Database of Protein Families," *Nuc. Acids Res.* 31:371-373 (2003).

Haft, et al., "A Guild of 45 CRISPR-Associated (Cas) Protein Families and Multiple CRISPR/Cas Subtypes Exist in Prokaryotic Genomes," *PLoS Comput. Biol.* 1(6):e60, 474-483 (2005).

Hale, et al., "Prokaryotic Silencing (PSI)RNAs in Pyrococcus Furiosus," *RNA* 14:2572-2579 (2008).

Harteveld and Higgs, "A-Thalassaemia," *Orphanet Journal of Rare Diseases* 5:13 (2010).

Hsu, et al., "DNA Targeting Specificity of RNA-Guided Cas9 Nucleases," *Nature Biotech.* 31:827-832 (2013) doi:10.1038/nbt. 2647.

Hwang, et al., "Efficient Genome Editing in Zebrafish Using a CRISPR-Cas System," *Nature Biotechnology* 31(3):227-229 (2013).

Jansen, et al., "Identification of Genes That Are Associated With DNA Repeats in Prokaryotes," *Mol. Microbiol.* 43:1565-1575 (2002).

Jinek, et al., "A Programmable Dual-RNA-Guided DNA Endonuclease in Adaptive Bacterial Immunity," *Science* 337:816 (2012).

Jinek, et al., "Structures of Cas9 Endonucleases Reveal RNA-Mediated Conformational Activation," *Science* 343(6176):1247997 (2014).

Kim, et al., "Highly Efficient RNA-Guided Genome Editing in Human Cells Via Delivery of Purified Cas9 Ribonucleoproteins," *Genome Research* 24:1012-1019 (2014).

Kim, et al., "Insertion and Deletion Mutants of FOKI Restriction Endonuclease," *J. Biol. Chem.* 269:31,978-31,982 (1994).

Kim, et al., "Chimeric Restriciton Endonuclease," *PNAS USA* 91:883-887 (1994).

Kormann, et al., "Expression of Therapeutic Proteins After Delivery of Chemically Modified MRNS in Mice," *Nature Biotechnology* 29(2):154-157 (2011).

Lee, et al., "A New Potent HFIX Plasmid for Hemophilia B Gene Therapy," *Pharm. Res.* 21(7):1229-1232 (2004).

Lei, et al., "Repurposing CRISPR as an RNA-Guided Platform for Sequence-Specific Control of Gene Expression," *Cell* 152(5):1173-1183 (2013).

Li, et al., "Functional Domains in FOK 1 Restriction Endonuclease," *PNAS USA* 89:4275-4279 (1992).

Li, et al., "Alteration of the Cleavage Distance of FOK I Restriction Endonuclease by Insertion Mutagenesis," *PNAS USA* 90:2764-2768 (1993).

Lillestol, et al., "A Putative Viral Defence Mechanism in Archaeal Cells," *Archaea* 2:59-72 (2006).

Makarova, et al., "A Putative RNA-Interference-Based Immune System Inprokaryotes: Computational Analysis of the Predicted Enzymatic Machinery, Functional Analogies With Eukaryotic RNAI, and Hypothetical Mechanisms of Action," *Biol. Direct* 1:7 (2006).

Makarova, et al., A DNA Repair System Specific for Thermophilic Archaea and Bacteria Is Predicted by Genomic Context Analysis, *Nuc. Acids Res.* 30:482-496 (2002).

Mali, et al., "RNA-Guided Human Genome Engineering Via Cas9," *Science* 339:823-826 (2013).

Nakamura, "A Cell-Based Method for Screening RNA-Protein Interactions: Identification of Constitutive Transport Element-Interacting Proteins," *PLOS One* 7(10):e48194 (2012).

Nishimasu, et al., "Crystal Structure of Cas9 in Complex With Guide RNA and Target DNA," *Cell* 156:935-949 (2014).

Perez, et al., "Establishment of HIV-1 Resistance in CD4+ T Cells by Genome Editing Using Zinc-Finger Nucleases," *Nature Biotechnology* 26(7):808-816 (2008).

Qi, et al., "Repurposing CRISPR As an RNA-Guided Platform for Sequence-Specific Control of Gene Expression," *Cell* 152:1173-1183 (2013).

(56) References Cited

OTHER PUBLICATIONS

Sander and Joung, "CRISPR-Cas Systems for Genome Editing, Regulation and Targeting," *Nature Biotech.* 32(4):347-355 (2014).
Sankaran, et al., "Human Fetal Hemoglobin Expression Is Regulated by the Developmental Stage-Specific Repressor BCL11A," *Science* 322:1839 (2008).
Sorek, et al., "CRISPR—A Widespread System That Provides Acquired Resistance Against Phages in Bacteria and Archaea," *Nat. Rev. Microbiol.* 6:181-186 (2008).
Tang, et al., "Identification of Novel Non-Coding RNAs As Potential Antisense Regulators in the Archaeon Sulfolobus Solfataricus," *Mol. Microbiol.* 55:469-481 (2005).
Tang, et al., "Identification of 86 Candidates for Small Non-Messenger RNAs From the Archaeon Archaeoglobus Fulgidus," *PNAS USA* 99:7536-7541 (2002).
Tatsuov, et al., "The COG Database: An Updated Version Includes Eukaryotes," *BMC Bioinformatics* 4(1):41 (2003).
Tatsuov, et al., "A Genomic Perspective on Protein Families," *Science* 278(5338):631-637 (1997).
Thein, et al., "Control of Fetal Hemoglobin: New Insights Emerging From Genomics and Clinical Implications," *Hum. Mol. Genet.* 18(R2):R216-R223 (2009).
Tsai, et al., "Dimeric CRISPR RNA-Guided FOKL Nucleases for Highly Specific Genome Editing," *Nature Biotechnology* 32(6):569-577 (2014).
Tsai, et al., "Guide-Seq Enables Genome-Wide Profiling of Off-Target Cleavage by CRISPR-Cas Nucleases," *Nature Biotechnology* 33:187-187 (2015).
Umov, et al., "Highly Efficient Endogenous Human Gene Correction Using Designed Zinc-Finger Nucleases," *Nature* 435(7042):646-651 (2010).
Van Loenen, et al., "Mixed T Cell Receptor Dimers Harbor Potentially Harmful Neoreactivity," *PNAS USA* 107(24):10972-10977 (2010).
Wu, et al., "Genome-Wide Binding of the CRISPR Endonuclease Cas9 in Mammalian Cells," *Nature Biotech.* (2014) doi:10.1038/nbt.2889.
Zetsche, et al., "A Split-Cas9 Architecture for Inducible Genome Editing and Transcription Modulation," *Nature Biotechnology* 33(2):139 (2015).

* cited by examiner

METHODS AND COMPOSITIONS FOR NUCLEASE DESIGN

CROSS-REFERENCE TO RELATED APPLICATIONS

The present application claims the benefit of U.S. Provisional Application No. 62/008,359, filed Jun. 5, 2014, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Aug. 14, 2015, is named 8325-0122SL.txt and is 13,152 bytes in size.

TECHNICAL FIELD

The present disclosure is in the field of genome engineering.

BACKGROUND

Gene therapy holds enormous potential for a new era in human medicine. These methodologies will allow treatment for conditions that heretofore have not been addressable by standard medical practice. One area that is especially promising is the ability to genetically engineer a cell to cause that cell to express a product that has not previously been produced in that cell. Examples of uses of this technology include the insertion of a transgene encoding a novel therapeutic protein, insertion of a coding sequence encoding a protein that is lacking in the cell or in the individual, insertion of a wild type gene in a cell containing a mutated gene sequence, and insertion of a sequence that encodes a structural nucleic acid such as a microRNA or siRNA.

To meet the challenge of increasing global demand for food production, many effective approaches to improving agricultural productivity (e.g. enhanced yield or engineered pest resistance) rely on either mutation breeding or introduction of novel genes into the genomes of crop species by transformation. Both processes are inherently non-specific and relatively inefficient. For example, conventional plant transformation methods deliver exogenous DNA that integrates into the genome at random locations. The random nature of these methods makes it necessary to generate and screen hundreds of unique random-integration events per construct in order to identify and isolate transgenic lines with desirable attributes. Moreover, conventional transformation methods create several challenges for transgene evaluation including: (a) difficulty for predicting whether pleiotropic effects due to unintended genome disruption have occurred; and (b) difficulty for comparing the impact of different regulatory elements and transgene designs within a single transgene candidate, because such comparisons are complicated by random integration into the genome. As a result, conventional plant trait engineering is a laborious and cost intensive process with a low probability of success.

Precision gene modification overcomes the logistical challenges of conventional practices in plant systems, and as such has been a longstanding but elusive goal in both basic plant biology research and agricultural biotechnology. However, with the exception of "gene targeting" via positive-negative drug selection in rice or the use of pre-engineered restriction sites, targeted genome modification in all plant species, both model and crop, has until recently proven very difficult. Terada et al. (2002) *Nat Biotechnol* 20(10):1030; Terada et al. (2007) *Plant Physiol* 144(2):846; D'Halluin et al. (2008) *Plant Biotechnology J.* 6(1):93.

Transgene (or trait) stacking has great potential for production of plants, but has proven difficult. See, e.g., Halpin (2005) *Plant Biotechnology Journal* 3:141-155. In addition, polyploidy, where the organism has two or more duplicated (autoploidy) or related (alloploid) paired sets of chromosomes, occurs more often in plant species than in animals. For example, wheat has lines that are diploid (two sets of chromosomes), tetraploid (four sets of chromosomes) and hexaploid (six sets of chromosomes). In addition, many agriculturally important plants of the genus *Brassica* are also allotetraploids.

Transgenes can be delivered to a cell by a variety of ways, such that the transgene becomes integrated into the cell's own genome and is maintained there. In recent years, a strategy for transgene integration has been developed that uses cleavage with site-specific nucleases for targeted insertion into a chosen genomic locus (see, e.g., co-owned U.S. Pat. No. 7,888,121). Nucleases specific for targeted genes can be utilized such that the transgene construct is inserted by either homology directed repair (HDR) or by end capture during non-homologous end joining (NHEJ) driven processes. Targeted loci include "safe harbor" loci such as the AAVS1, HPRT and CCR5 genes in human cells, and Rosa26 in murine cells (see, e.g., U.S. Pat. Nos. 8,623,618; 8,034,598; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20060063231; 20080159996; 201000218264; 20120017290; 20110265198; 20130137104; 20130122591; 20130177983; 20130177960 and 20150056705) and the Zp15 locus in plants (see U.S. Pat. No. 8,329,986). Nuclease-mediated integration offers the prospect of improved transgene expression, increased safety and expressional durability, as compared to classic integration approaches that rely on random integration of the transgene, since it allows exact transgene positioning for a minimal risk of gene silencing or activation of nearby oncogenes.

Genome engineering can also include the knocking out of genes in addition to insertion methods described above. In the absence of a donor nucleic acid, a cell with a cleaved genome will resort to the error prone NHEJ pathway to heal the break. This process often adds or deletes nucleotides during the repair process ("indels") which may lead to the introduction of missense or non-sense mutations at the target site. For example, CCR5-specific zinc finger nucleases are being used in Phase I/II trials to create a non-functional CCR5 receptor, and thus prevent HIV infection (see U.S. Pat. No. 7,951,925).

Targeted nuclease-mediated genome cleavage at a desired location can be obtained by the use of an engineered nuclease. For example, a double-strand break (DSB) for can be created by a site-specific nuclease such as a zinc-finger nuclease (ZFN) or TAL effector domain nuclease (TALEN). See, for example, Urnov et al. (2010) *Nature* 435(7042):646-51; U.S. Pat. Nos. 8,586,526; 6,534,261; 6,599,692; 6,503,717; 6,689,558; 7,067,317; 7,262,054, the disclosures of which are incorporated by reference in their entireties for all purposes.

Another nuclease system involves the use of a so-called acquired immunity system found in bacteria and archaea known as the CRISPR/Cas system. CRISPR/Cas systems are found in 40% of bacteria and 90% of archaea and differ in the complexities of their systems. See, e.g., U.S. Pat. No. 8,697,359. The CRISPR loci (clustered regularly interspaced short palindromic repeat) is a region within the organism's genome where short segments of foreign DNA are integrated between short repeat palindromic sequences. These loci are transcribed and the RNA transcripts ("pre-crRNA") are processed into short CRISPR RNAs (crRNAs). There are three types of CRISPR/Cas systems which all incorporate these RNAs and proteins known as "Cas" proteins (CRISPR associated). Types I and III both have Cas endonucleases that process the pre-crRNAs, that, when fully processed into crRNAs, assemble a multi-Cas protein complex that is capable of cleaving nucleic acids that are complementary to the crRNA.

In type II systems, crRNAs are produced using a different mechanism where a trans-activating RNA (tracrRNA) complementary to repeat sequences in the pre-crRNA, triggers processing by a double strand-specific RNase III in the presence of the Cas9 protein. Cas9 is then able to cleave a target DNA that is complementary to the mature crRNA however cleavage by Cas 9 is dependent both upon base-pairing between the crRNA and the target DNA, and on the presence of a short motif in the crRNA referred to as the PAM sequence (protospacer adjacent motif) (see Qi et al (2013) *Cell* 152:1173). In addition, the tracrRNA must also be present as it base pairs with the crRNA at its 3' end, and this association triggers Cas9 activity.

The Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand.

The requirement of the crRNA-tracrRNA complex can be avoided by use of an engineered "single-guide RNA" (sgRNA) that comprises the hairpin normally formed by the annealing of the crRNA and the tracrRNA (see Jinek et al (2012) *Science* 337:816 and Cong et al (2013) *Sciencexpress*/10.1126/science.1231143). In *S. pyrogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing (see Ramalingam ibid) and has been useful for zebrafish embryo genomic editing in vivo (see Hwang et al (2013) *Nature Biotechnology* 31 (3):227) with editing efficiencies similar to ZFNs and TALENs.

Thus, there remains a need for systems for genomic editing, including for treatment and/or prevention of diseases and for agricultural uses.

SUMMARY

Disclosed herein are methods and compositions for genetic modification, for example for the treatment of a disease or for production of genetically modified plants. Genome editing is used to correct an aberrant gene, insert a wild type gene, or change the expression of an endogenous gene. One or more endogenous genes can be targeted for genomic editing, including any mammalian or plant gene(s). By way of non-limiting example, a wild-type gene encoding β globin may be inserted into the genome of a cell to treat a hemoglobinopathy caused by faulty β globin. In some instances, the wild type gene may be inserted into a safe harbor locus or at a locus known to be highly expressed in a tissue of interest such as the β globin locus in erythroid cells. Another approach disclosed here involves the use of gene correction where a faulty endogenous gene is targeted and the mutant sequence replaced using an engineered donor (e.g., the mutant is replaced with a functional sequence). Alternately, one or more regulatory genes involved in the modulation of another gene may be altered, for example a regulatory gene involved in repression of a gene may be altered or knocked out such that the normally repressed gene is now expressed or not expressed, or the regulatory binding site upstream of the a gene or in other areas of the locus are altered so that the regulators are not able to interact properly with the DNA at the gene locus and regulate gene expression. Another approach further involves the use of modified stem cells (e.g., hematopoietic stem cell or red blood cell (RBC) precursor), which can then be used to engraft into a patient, for treatment of a hemoglobinopathy or other disease (e.g., genetic disease).

In one aspect, described herein is a CRISPR/Cas system that binds to a target site in a region of interest in an endogenous gene (e.g., an endogenous or safe harbor gene, or a regulatory gene or its DNA target) in a genome, wherein the CRISPR/Cas system comprises one or more engineered single guide RNAs that recognize the target gene and a functional domain (e.g., a transcriptional regulatory domain and/or a nuclease domain).

The CRISPR/Cas system as described herein may bind to and/or cleave the region of interest in a coding or non-coding region within or adjacent to the gene, such as, for example, a leader sequence, trailer sequence or intron, or within a non-transcribed region, either upstream or downstream of the coding region. In certain embodiments, the CRISPR/Cas binds to and/or cleaves a gene. In other embodiments, the CRISPR/Cas binds to and/or cleaves a safe-harbor gene, for example a CCR5 gene, a PPP1R12C (also known as AAVS1) gene, or a Rosa gene in mammalian cells, and the Zp15 locus in plants. PPP1R12C has 22 exons in its coding sequence, and an especially preferred location for targeting is within intron 1 (i.e. at or near chr19:55624164-55624759), enabling the insertion of a promoter-less transgene. In addition, to aid in selection in mammalian systems, the HPRT locus may be used (see U.S. Pat. Nos. 9,222,105; and 8,895,264). In some embodiments, the CRISPR/Cas binds to and cleaves at regulatory elements. In another aspect, described herein are compositions comprising one or more of the CRISPR/Cas nucleases as described herein.

In one aspect, the CRISPR/Cas system as described may bind to and/or modulate expression of a gene of interest. In one embodiment, the CRISPR/Cas system binds to a DNA sequence and prevents binding of other regulatory factors. In another embodiment, the binding of a CRISPR/Cas system fusion protein may modulate (i.e. induce or repress) expression of a target DNA.

In another aspect, described is a polynucleotide encoding one or more CRISPR/Cas system described herein. The polynucleotide may be, for example, mRNA. In some aspects, the mRNA may be chemically modified (See e.g. Kormann et al, (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication 2012/0195936).

In another aspect, described is a CRISPR/Cas system expression vector comprising a polynucleotide encoding one or more CRISPR/Cas components described herein, operably linked to a promoter. In one embodiment, the expression vector is a viral vector. In another embodiment, the expression vector is a DNA minicircle.

In one aspect, described herein is a Cas protein that is used to cleave a target DNA.

In another aspect, described herein is a method of modifying an endogenous gene (e.g., modulating expression of the endogenous gene), the method comprising administering to the cell a first nucleic acid molecule comprising a single guide RNA that recognizes a target site in the endogenous gene and a second nucleic acid molecule that encodes a functional domain, wherein the functional domain associates with the single guide RNA on the target site, thereby modifying the endogenous gene. The first and second nucleic acids may be on the same or different vectors. In some embodiments, the guide RNA associating domain is delivered to the cell as a protein. In certain embodiments, the endogenous gene is selected from the group consisting of a mammalian β globin gene (HBB), a gamma globin gene (HBG1), a B-cell lymphoma/leukemia 11A (BCL11A) gene, a Kruppel-like factor 1 (KLF1) gene, a CCR5 gene, a CXCR4 gene, a PPP1R12C (AAVS1) gene, an hypoxanthine phosphoribosyltransferase (HPRT) gene, an albumin gene, a Factor VIII gene, a Factor IX gene, a Leucine-rich repeat kinase 2 (LRRK2) gene, a Hungtingin (Htt) gene, a rhodopsin (RHO) gene, a Cystic Fibrosis Transmembrane Conductance Regulator (CFTR) gene, a surfactant protein B gene (SFTPB), a T-cell receptor alpha (TRAC) gene, a T-cell receptor beta (TRBC) gene, a programmed cell death 1 (PD1) gene, a Cytotoxic T-Lymphocyte Antigen 4 (CTLA-4) gene, an human leukocyte antigen (HLA) A gene, an HLA B gene, an HLA C gene, an HLA-DPA gene, an HLA-DQ gene, an HLA-DRA gene, a LMP7 gene, a Transporter associated with Antigen Processing (TAP) 1 gene, a TAP2 gene, a tapasin gene (TAPBP), a class II major histocompatibility complex transactivator (CIITA) gene, a dystrophin gene (DMD), a glucocorticoid receptor gene (GR), an IL2RG gene, an RFX5 gene, a FAD2 gene, a FAD3 gene, a ZP15 gene, a KASII gene, a MDH gene, an EPSPS gene, microtubule associated protein tau (MAPT gene, encoding Tau proteins) and/or apolipoprotein E (APOE) alleles (e.g., apoE2, apoE3 or apoE4, for stroke, concussion and/or Alzheimer's disease (AD), and epilepsy); alpha-synuclein (SNCA); amyloid precursor protein (APP), presenilin 1: PSEN1 and/or presenilin 2: PSEN2 (e.g., for AD); SLC6A4, HTR2A, alpha-1 subunit of a voltage-dependent calcium channel (CACNAIC) and/or calcium channel, voltage-dependent, beta 2 subunit (CACNB2) (e.g., for depression and/or migraines); dystrophia myotonica-protein kinase (DMPK for myotonic dystrophy); CACNA1A, ATP1A2, SCN1A (e.g., for migraine); FXN (for Friedrich's Ataxia); PMP22 (CMT); dystrophin (DMD) and/or utrophin (UTRN, e.g., for Duchenne's muscular dystrophy); C9orf72, SOD1, TARDBP, FUS, ANG, ALS2, SETX, progranulin gene (GRN) and/or VAPB (e.g., for Amyotrophic lateral sclerosis (ALS) and/or dementia); FMR1 (e.g., for Fragile X) and/or HPRT (e.g., for Lesch-Nyhan Disease); MECP2 (Rett syndrome); ASPA (Canavan Disease); SCN1A, SCN8A (Dravet syndrome); SMN1, SMN1 (SMA); UGT1A1 (Crigler Najjir); OPRM1, OPRK1, OPRD1 (opiate addiction); OPRM1 (Borderline personality disorder); SLC6A4, HTR2a, TPH2 (Major depressive disorder); DRD2, GRM3, GRIN2A, SRR, GRIA1, CACNA1C, CACNB2, CACN11I, GAD1, RELN, BDNF, TET1, and DTNBP1 (Schizophrenia); ANK3, ODZ4, TRANK1, ADCY2, CACNA1C, BDNF (Bipolar disorder); PRDM16, AJAP1, MEF2D, TRPM8, TGFBR2, PHACTR1, FHM5, c7orf10, MMP16, ASTN2, TSPAN2, GFRA2 and LRP1 (Migraine); HLA-DRB1, IL7Ra, IL2Ra, CYP27Ba, TYK2 (multiple sclerosis); NRXN1, AADAC, CTNNA3, FSCB, KCHE1, KCHE2, RCAN1 (Tourette syndrome); CAMSAP1LK1, NMDA receptor subunit 1, GAMA-A receptor subunit alpha-1, GAD65, adenosine kinase, GCNF, BDNF, IGF, neuropeptide Y, galanin (epilepsy).

In any of the methods and compositions described herein, the cell can be any eukaryotic cell(s), for example a plant cell or a mammalian cell or cell line, including COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodopterafugiperda* (Sf), or fungal cells such as *Saccharomyces, Pichia* and *Schizosaccharomyces*. In certain embodiments, the cell line is a CHO, MDCK or HEK293 cell line. Primary cells can also be edited as described herein, including but not limited to fibroblasts, blood cells (e.g., red blood cells, white blood cells), liver cells, kidney cells, neural cells, and the like. Suitable cells also include stem cells such as, by way of example, embryonic stem cells, induced pluripotent stem cells (iPSCs), hematopoietic stem cells, neuronal stem cells and mesenchymal stem cells. In other aspects, genetically modified blood cell precursors (hematopoietic stem cells known as "HSCs") are given in a bone marrow transplant and the HSCs differentiate and mature in vivo.

In other aspects, genetically modified RBC precursors and/or hematopoietic stem cells (HSCs) are given in a bone marrow transplant and the RBCs differentiate and mature in vivo. In some embodiments, the HSCs are isolated from the peripheral blood following G-CSF-induced mobilization, and in others, the cells are isolated from human bone marrow or umbilical cord blood. In some aspects, the HSCs are edited by treatment with a nuclease designed to knock out a specific gene or regulatory sequence. In other aspects, the HSCs are modified with an engineered nuclease and a donor nucleic acid such that a wild type gene is inserted and expressed and/or an endogenous aberrant gene is corrected. In some embodiments, an engineered gene is inserted and expressed. In some embodiments, the modified HSCs are administered to the patient following mild myeloablative pre-conditioning. In other aspects, the HSCs are administered after full myeloablation such that following engraftment, a majority of the hematopoietic cells are derived from the newly engrafted modified HSC population.

In one aspect, the methods and compositions described herein comprise at least one mutated Cas nuclease. In some embodiments, the mutant Cas nucleases are Cas9 nucleases, and have altered functionality. In some embodiments, the Cas9 protein is mutated in the HNH domain, rendering it unable to cleave the DNA strand that is complementary to the crRNA. In other embodiments, the Cas9 is mutated in the RuvC domain, making it incapable of cleaving the non-complimentary DNA strand. These mutations can result in the creation of Cas9 nickases. In some embodiments, two Cas nickases are used with two separate crRNAs to target a DNA, which results in two nicks in the target DNA at a specified distance apart. In other embodiments, both the HNH and RuvC endonuclease domains are altered to render a Cas9 protein which is unable to cleave a target DNA.

In another aspect, the methods and compositions of the invention comprise truncations of the Cas9 protein. In one embodiment, the Cas9 protein is truncated such that one or more of the Cas9 functional domains are removed. In one embodiment, the removal of part or one of the nuclease domains renders the Cas nuclease a nickase. In one embodiment, the Cas9 comprises only the domain responsible for interaction with the crRNA or sgRNA and the target DNA.

In still further aspects, the methods and compositions of the invention also comprise fusion proteins wherein the Cas9 protein, or truncation thereof, is fused to a functional domain. In some aspects, the functional domain is an activation or a repression domain. In other aspects, the functional domain is a nuclease domain. In some embodiments, the nuclease domain is a wild-type or engineered FokI endonuclease domain (e.g. Tsai (2014) *Nature Biotech* doi:10.1038/nbt.2908). In some embodiments, the FokI domain comprises mutations in the dimerization domain. In some aspects, a nuclease-defective (catalytically inactive) Cas 9 protein is fused to a FokI domain (e.g., a wild type FokI domain or a FokI domain that comprises mutations in the dimerization domain). In some embodiments, the Cas9 protein is nuclease defective due to one or more mutations in the Cas9 nuclease domain(s) (e.g., stop codons, insertions mutations, deletions and/or combinations thereof) while in others, the one or more truncations in the Cas9 protein result in a defective (inactive) nuclease. Thus, in some embodiments, the fusion proteins (comprising the Cas9 proteins) as described herein are nucleases comprised of a dimer of two further fusion proteins, where each fusion protein of the dimer comprises a Cas9 DNA recognition domain and heterologous nuclease (cleavage) domain. In some embodiments, the heterologous nuclease domain is a FokI nuclease domain. In further embodiments, the FokI domain comprises mutations in the dimerization domain. In some aspects, the Cas9-FokI nuclease comprises a dimer of two fusion proteins comprising a Cas9 DNA recognition domain and a FokI nuclease domain comprising a mutation in the dimerization domain, wherein the two FokI domains in the active nuclease dimer comprise different dimerization domain mutations (e.g., dimerization domains that form obligate heterodimers).

In another aspect, the methods and compositions of the invention include an active Cas9 nuclease dimer comprising two fusion proteins, wherein each fusion comprises a Cas9 DNA recognition domain fused to a nuclease domain in which the two Cas9 DNA recognition domains are not identical to each other (e.g., the two Cas9 proteins of the dimer are different, for example they differ in their interaction with the target DNA). In further embodiments, the two Cas9 proteins of the dimer utilize different PAM sequences for DNA recognition. In some embodiments, the Cas9 proteins in the dimer are identical except for the regions in the Cas9 protein that interact with the PAM sequence.

In further aspects, described herein is a system comprising two Cas9 nuclease dimer pairs (four Cas9 nucleases), in which each nuclease comprises a different FokI domain (four different FokI domains) (see, e.g., US Patent Publication No. 20110201055), in which FokI domain of a given pair forms an active heterodimer but which do not form active heterodimers with the either domain of the other pair. (e.g., ELD/KKR domains in the first pair and DAD/RVR in the second pair). In this embodiment, simultaneous cleavage occurs at two target sites within a genome. The nuclease pairs that cleave at the two desired loci productively dimerize in only the designed configuration, i.e, the pairs will not homodimerize or transheterodimerize to create an active pair. For example, if target 1 is cleaved by Cas9-Fok fusion pair A+B, and target 2 is cleaved by Cas9-Fok fusion pair X+Y, pairings of A+A (homodimers), A+X and A+Y (transheterodimers), for example, are avoided. Typically, The DNA targets sites are selected such that they comprise a PAM sequence specific for the Cas9 domain in the fusion.

Thus, described herein is a Cas9 nuclease dimer comprising two fusion proteins, each fusion comprising a Cas9 DNA recognition domain fused to a FokI nuclease domain, wherein the FokI nuclease domains are different from each other. In certain embodiments, the Cas9 DNA recognition domains interact with different PAM sequences, for example, these proteins differ only in regions that interact with the PAM sequence. A system comprising any of the Cas9 nuclease dimers described herein and one or more single guide RNAs (sgRNAs) is also provided. Also provided is a system comprising first, second, third and fourth Cas9 nucleases comprising first, second, third and fourth Cas9 domains and first, second, third and fourth FokI domains, wherein: (i) the first, second, third and fourth FokI domains are different from each other; (ii) the first and second FokI domains dimerize to form a first active dimer pair; (iii) the third and fourth FokI domains dimerize to form a second active dimer pair; and (iv) the first and second FokI domains do not dimerize with the third or fourth FokI domains. By "active" dimer pair is meant a nuclease dimer that makes a single- or double-stranded cut when dimerized. In certain embodiments, the system further comprises first, second, third and fourth sgRNAs. In any of the systems described herein, one or more of the FokI domains may comprise one or more mutations, for example in the dimerization domain and/or in the catalytic domain (e.g., such that the dimer functions as a nickase. Furthermore, in any of the systems described herein, the Cas9 domains may be derived from at least two different bacterial species. Also provided is a method of cleaving at least one target sequence in a cell, the method comprising introducing a system as described herein into the cell such that the target is cleaved.

In further aspects, orthogonal Cas9 domains, wherein Cas9 domains are selected from different bacterial species, are used in conjunction with the orthogonal Fok I domains described above.

In yet another aspect, the methods and compositions described herein include a Cas polypeptide (e.g., Cas9) comprising one or more mutations (insertions, deletions and/or substitutions) that alter interaction of the Cas polypeptide with the PAM sequence. In certain embodiments, the Cas polypeptide is altered so that it interacts with a PAM sequence having the sequence 5'NGA, 5'NGG, 5'NGC, 5'NGT, 5'NAG, 5' NAC, 5'NAT, 5'NCA, 5'NCT, 5'NTA, 5'NTC, 5'NCG, 5'NTG, 5'NAA, 5'NCC or 5'NTT. In certain embodiments, the altered (mutated) Cas polypeptide interacts with a PAM sequence having the sequence 5'NGA, 5'NGC, 5'NGT, 5' NAC, 5'NAT, 5'NCA, 5'NCT, 5'NTA, 5'NTC, 5'NCG, 5'NTG, 5'NAA, 5'NCC or 5'NTT. In certain embodiments, the altered (mutated) Cas polypeptide has an interaction preference for PAM sequences with a specific base pair in the first position of the PAM (e.g. 5'AGG, 5'CGG, 5'GGG, and 5'TGG). In other embodiments, the altered (mutated) Cas polypeptide has an interaction preference for PAM sequences with a specific base pair in the position immediately 3' of the PAM sequence (e.g. 5'NGGA, 5'NGGC, 5'NGGG, and 5'NGGT where N can be A, C, T or G). In any of the altered Cas polypeptides described herein, the mutation(s) is/are in the α-helical lobe of a Cas9 protein are present to alter PAM interaction (see Jinek et al (2014) *Science* 343; 1247997). In some aspects, mutations are in the region of the Cas9 protein extending between approximately amino acid 78 to amino acid 718 (or anywhere therebetween), as numbered relative to SEQ ID NO:2. In other aspects, the C-terminal domain comprises one or more mutations that alter PAM interaction. In some aspects, mutations are generated in the Cas9 protein between amino acids 1099 to 1368 or 1200 to 1368 (or anywhere therebetween), numbered relative to SEQ ID NO:2. In some embodiments, the Cas9 protein comprises an altered tryptophan containing loop at amino acids 447-502 (numbered relative to SEQ ID NO:2), or comprises one or more mutations in the tryptophan containing loop (amino acids 1102-1137, numbered relative to SEQ ID NO:2). In further embodiments, the Cas9 protein comprises one or more alterations in both the 447-50 and 1102-1137 loops (numbered relative to SEQ ID NO:2) such that an altered DNA PAM site recognition occurs. Also described are systems and complexes (e.g., CRISPR/Cas systems and complexes) comprising one or more Cas polypeptides as described herein and one or more sgRNAs as well as such systems complexed to a target sequence (e.g., in an endogenous gene). Methods of cleaving a target sequence in a cell (e.g., isolated cell) are also provided using the polypeptides and/or systems described herein. Also provided are methods of screening for altered Cas polypeptides as described herein. Thus, described herein is a Cas polypeptide that binds to a target sequence comprising a protospacer adjacent motif (PAM) sequence, the Cas polypeptide (e.g., Cas9 polypeptide) comprising one or more mutations as compared to wild-type, wherein the mutations alter interaction of the Cas polypeptide with the PAM sequence of the target sequence. In certain embodiments, the mutations are: in the α-helical lobe of the Cas9 protein; in the region of the Cas9 protein extending between amino acid 78 to amino acid 718 of SEQ ID NO:2; in the C-terminal domain of the Cas polypeptide; between amino acids 1099 to 1368 or 1200 to 1368 (or anywhere therebetween), as compared to the wild-type sequence (SEQ ID NO:2); and/or in an altered tryptophan containing loop between amino acids 447-502 or 1102-1137 (or anywhere therebetween) as compared to wild-type (SEQ ID NO:2). A system comprising any of the Cas polypeptides described herein and a single guide RNA (sgRNA) is also provided. A complex comprising any of the systems described herein, a target sequence (e.g., in an endogenous gene) and a PAM sequence is also provided. Also provided are methods of cleaving a target sequence in a cell, the method comprising introducing any of the systems described herein into the cell such that the target is cleaved. A cell comprising a cleaved target made by the systems and methods as described herein is also provided.

In some embodiments, the active nuclease dimer comprises two fusion proteins wherein the two FokI nuclease domains differ in their dimerization domains, and in which the Cas9 recognition domains differ in their PAM recognition sequences. In further embodiments, the active nuclease dimer comprises two Cas9-FokI fusion proteins wherein the FokI nuclease domains in each fusion protein differ in their dimerization domains, and the Cas9 DNA recognition domains in each fusion protein are orthogonal to each other in that they require distinct guide RNA scaffold sequences (see Mali et al., (2013) *Science* 339:823-826). These orthogonal Cas9 domains can either be derived from different species (Esvelt et al., *Nat. Methods.* (2013) 10:1116-1121) or derived by mutating residues in one or both Cas9 domains and mutating one or more nucleotides in the guide RNA scaffold such that each Cas9 domain interacts with a distinct guide RNA. Such a nuclease dimer would retain activity at the intended target, but would no longer retain activity at genomic sites where a single guide RNA is able to bind at two genomic loci within 100 base pairs of each other.

In another aspect, described herein is a method for inserting a sequence into an endogenous gene (e.g., safe harbor gene) in a cell (e.g. stem cell), the method comprising cleaving the endogenous gene using one or more nucleases and inserting a sequence into the cleavage site. In certain embodiments, a genomic sequence in any target gene is replaced, for example using a CRISPR/Cas system (or vector encoding said CRIPSR/Cas system) as described herein and a "donor" sequence (also known as a "transgene") that is inserted into the gene following targeted cleavage. The donor sequence may be present in the CRISPR/Cas vector, present in a separate vector (e.g., Ad, AAV, DNA minicircle or LV vector) or, alternatively, may be introduced into the cell using a different nucleic acid delivery mechanism. For example, mRNA encoding the Cas nuclease protein may be introduced into a cell with the desired sgRNA by electroporation. Such insertion of a donor nucleotide sequence into the target locus (e.g., safe-harbor gene) results in the expression of the transgene under control of the target locus's genetic control elements. In some embodiments, the transgene encodes a non-coding RNA (e.g. an shRNA). Expression of the transgene prior to stem cell differentiation will result in a derivative cell containing the non-coding RNA of interest.

In some embodiments, the methods and compositions of the invention are performed in and/or comprise plant cells. In some aspects, the plant cells are meristematic cells. In some embodiments, the plant cells comprise a nuclease of the invention. In other embodiments, the plant cells additionally comprise a transgene. In yet another aspect, described herein is a method for introducing one or more exogenous sequence into the genome of a plant cell, the method comprising the steps of: (a) contacting the cell with the one or more exogenous sequences (donor vector, transgene or GOI); and (b) expressing one or more nucleases (e.g., CRISPR/Cas system) as described herein in the cell, wherein the one or more nucleases cleave chromosomal DNA; such that cleavage of chromosomal DNA in step (b) stimulates incorporation of the donor vector into the genome by homologous recombination. Multiple transgenes may be integrated simultaneously (in parallel) or the steps may be repeated for sequential addition of transgenes (transgene stacking).

In other embodiments, the transgene comprises a functional protein, for example a globin (e.g., wild type beta and/or wild type gamma) protein. In other embodiments, the transgene encodes an engineered gene for production of a novel protein with desirable qualities. In some embodiments, insertion of the transgene of interest into an endogenous gene, results in expression of an intact exogenous protein sequence and lacks any sequences encoded by the endogenous gene. In other embodiments, the expressed exogenous protein is a fusion protein and comprises amino acids encoded by the transgene and by the endogenous gene (e.g., from the endogenous target locus). When present, endogenous sequences may be present on the amino (N)-terminal portion of the exogenous protein and/or the carboxy (C)-terminal portion of the exogenous protein. In some aspects, the safe harbor is selected from the AAVS1, Rosa, HPRT, Zp15 or CCR5 locus (see U.S. Patent Publications Nos. 20080299580; 20080159996; and 201000218264 U.S. Pat. Nos. 8,329,986; 9,222,105; and 8,895,264).

In yet another aspect, provided herein are genomically modified cell lines and/or transgenic organisms such as animal models (systems). In some embodiments, the transgenic cell and/or organism (e.g., animal) includes a transgene that encodes a human gene. In some instances, the transgenic animal comprises a knock out at the endogenous locus corresponding to exogenous transgene, thereby allowing the development of an in vivo system where the human protein may be studied in isolation. Such transgenic models may be used for screening purposes to identify small molecules or large biomolecules or other entities which may interact with or modify the human protein of interest. In some embodiments, the cell lines of the invention are used in cell-based assays for activity screens in pharmaceutical development, while in other embodiments, the cell lines are used in diagnostic assays. In some aspects, the transgene is integrated into the selected locus (e.g., safe-harbor) into a stem cell (e.g., an embryonic stem cell, an induced pluripotent stem cell, a hematopoietic stem cell, etc.) or animal embryo obtained by any of the methods described herein, and then the embryo is implanted such that a live animal is born. The animal is then raised to sexual maturity and allowed to produce offspring wherein at least some of the offspring comprise edited endogenous gene sequence or the integrated transgene.

In a still further aspect, a cell (e.g., plant or mammalian cell) obtained according to any of the methods described herein is also provided.

In another aspect, provided herein is an organism (e.g., plant or animal) comprising a cell (e.g., plant or animal) as described herein.

In another aspect, provided herein is a seed from a plant comprising the plant cell that is obtained as described herein.

In another aspect, provided herein is fruit obtained from a plant comprising plant cell obtained as described herein.

In any of the compositions (cells or plants) or methods described herein, the plant cell can comprise a monocotyledonous or dicotyledonous plant cell. In certain embodiments, the plant cell is a crop plant, for example, wheat, tomato (or other fruit crop), potato, maize, soy, alfalfa, etc.

In a still further aspect, provided herein is a method for site-specific integration of a nucleic acid sequence into an endogenous locus (e.g., safe harbor gene) of a chromosome, for example into the chromosome of an embryo. In certain embodiments, the method comprises: (a) injecting an embryo with (i) at least one DNA vector, wherein the DNA vector comprises an upstream sequence and a downstream sequence flanking the nucleic acid sequence to be integrated, and (ii) at least one RNA molecule encoding a CRISPR/Cas system nuclease that recognizes the site of integration in the target locus (e.g., globin or safe harbor locus), and (b) culturing the embryo to allow expression of the CRISPR/Cas system nuclease, wherein a double stranded break introduced into the site of integration by the CRISPR/Cas system nuclease is repaired, via homologous recombination with the DNA vector, so as to integrate the nucleic acid sequence into the chromosome.

In any of the methods described herein, the polynucleotide encoding the CRISPR/Cas system can comprise DNA, RNA or combinations thereof. In certain embodiments, the polynucleotide comprises a plasmid. In other embodiments, the polynucleotide encoding the nuclease comprises mRNA.

A kit, comprising a CRISPR/Cas system of the invention, is also provided. The kit may comprise nucleic acids encoding a CRISPR/Cas system, (e.g. RNA molecules or CRISPR/Cas system encoding genes contained in a suitable expression vector), or aliquots of the nuclease proteins, donor molecules, suitable host cell lines, instructions for performing the methods of the invention, and the like.

These and other aspects will be readily apparent to the skilled artisan in light of disclosure as a whole.

DETAILED DESCRIPTION

Disclosed herein are methods and compositions for genome engineering, including genome engineering to study and treat a disease or for the creation of a plant with desirable traits. The invention describes genomic editing of any target cell such that there is a favorable change in the expression of one or more genes, which in turn results in treatment of a disease in a subject in need thereof or the production of a desirable plant. Non-limiting examples of diseases include genetic diseases (e.g., hemoglobinopathies, hemophilia, lysosomal storage diseases, cystic fibrosis etc.), infectious diseases (e.g., HIV), neurological diseases (e.g., PD, HD, etc.), cancers, and the like. Additionally, delivery of altered stem cells in a transplant altered to express a desired protein product can be similarly beneficial in a disease. Also described are cell lines and organisms (e.g., plants or animals) with altered gene expression. Described below are genes to be targeted by the CRISPR/Cas system using the sgRNAs of the invention. Mammalian gene locations as described are relative to the UCSC Genome Brower created by the Genome Bioinformatics Group of UC Santa Cruz, software copyright the Regents of the University of California. Human genomic coordinates are provided in the GRCh37/hg19 assembly of the human genome, and correspond to numbers on a double stranded DNA. Thus, any position described by a genomic coordinate corresponds to either the (+) or Watson strand, or may specify its corresponding (−) or Crick strand.

Exemplary targets include genes involved in hemoglobinopathies. Hemoglobin is a heterotetramer comprising two α-like globin chains and two β-like globin chains and 4 heme groups. In adults the α2β2 tetramer is referred to as Hemoglobin A (HbA) or adult hemoglobin. Typically, the alpha and beta globin chains are synthesized in an approximate 1:1 ratio and this ratio seems to be critical in terms of hemoglobin and RBC stabilization. In fact, in some cases where one type of the globin genes is inadequately expressed (see below), reducing expression (e.g. using a specific siRNA) of the other type of globin, restoring this 1:1 ratio, alleviates some aspects of the mutant cellular phenotype (see Voon et al (2008) *Haematologica* 93(8):1288). In a developing fetus, a different form of hemoglobin, fetal hemoglobin (HbF) is produced which has a higher binding affinity for oxygen than Hemoglobin A such that oxygen can be delivered to the baby's system via the mother's blood stream. Fetal hemoglobin also contains two α globin chains, but in place of the adult β-globin chains, it has two fetal γ-globin chains (α2γ2). At approximately 30 weeks of gestation, the synthesis of γ-globin in the fetus starts to drop while the production of β-globin increases. By approximately 10 months of age, the newborn's hemoglobin is nearly all α2β2 although some HbF persists into adulthood (approximately 1-3% of total hemoglobin). The regulation of the switch from production of γ to β is quite complex, and primarily involves an expressional down-regulation of γ-globin with a simultaneous up-regulation of β-globin expression.

Genetic defects in the sequences encoding the hemoglobin chains can be responsible for a number of diseases known as hemoglobinopathies, including sickle cell anemia and thalassemias. In the majority of patients with hemoglobinopathies, the genes encoding γ-globin remain present, but expression is relatively low due to normal gene repression occurring around parturition as described above.

It is estimated that 1 in 5000 people in the U.S. have sickle cell disease (SCD), mostly in people of sub-Saharan Africa descent. There appears to be a benefit of sickle cell heterozygosity for protection against malaria, so this trait may have been selected for over time, such that it is estimated that in sub-Saharan Africa, one third of the population has the sickle cell trait. Sickle cell disease is caused by a mutation in the β-globin gene in which valine is substituted for glutamic acid at amino acid #6 (a GAG to GTG at the DNA level), where the resultant hemoglobin is referred to as "hemoblobin S" or "HbS." Under lower oxygen conditions, the deoxy form of HbS exposes a hydrophobic patch on the protein between the E and F helices. The hydrophobic residues of the valine at position 6 of the beta chain in hemoglobin are able to associate with the hydrophobic patch, causing HbS molecules to aggregate and form fibrous precipitates. These aggregates in turn cause the abnormality or 'sickling' of the RBCs, resulting in a loss of flexibility of the cells. The sickling RBCs are no longer able to squeeze into the capillary beds and can result in vaso-occlusive crisis in sickle cell patients. In addition, sickled RBCs are more fragile than normal RBCs, and tend towards hemolysis, eventually leading to anemia in the patient.

Thalassemias are also diseases relating to hemoglobin and typically involve a reduced expression of globin chains. This can occur through mutations in the regulatory regions of the genes or from a mutation in a globin coding sequence that results in reduced expression. Alpha thalassemias are associated with people of Western Africa and South Asian descent, and may confer malarial resistance. Beta thalassemia is associated with people of Mediterranean descent, typically from Greece and the coastal areas of Turkey and Italy. Treatment of thalassemias usually involves blood transfusions and iron chelation therapy. Bone marrow transplants are also being used for treatment of people with severe thalassemias if an appropriate donor can be identified, but this procedure can have significant risks.

Correction of the human HBB gene that encodes beta globin can be accomplished with the CRISPR/Cas system of the invention. Preferred locations of cleavage include targeting the HBB gene sequence (i.e. at or near chr11: 5246696-5248301). Especially preferred is to target regions of HBB in a HBS allele to achieve gene correction of a sickle allele. Especially preferred for use of a *S. pyogenes* Cas9 system is targeting sequences where the PAM site is at or near positions on chromosome 11: 5248110, 5248106, 5248100, 5248090, 5248122, 5248112 for correction of a sickle allele. For gene correction of a beta-globin allele associated with a beta thalessemia there are many potential targets. One well known mutation associated with beta thalassemia is the so-called IVS1.1 mutation, where a preferred targeting region would be around nucleotides 1093-1192 of the HBB gene sequence. Most preferred are targeting sequences where the PAM site is at or near positions on chromosome 11: 5248170-5248171, 5248168-5248169, 5248167-5248168, 5248164-5248165, 5248163-5248164, 5248155-5248156 and 5248147-5248148.

One approach for the treatment of both SCD and beta thalassemias that has been proposed is to increase the expression of γ-globin with the aim to have HbF functionally replace the aberrant adult hemoglobin. As mentioned above, treatment of SCD patients with hydroxyurea is thought to be successful in part due to its effect on increasing γ-globin expression. The first group of compounds discovered to affect HbF reactivation activity were cytotoxic drugs. The ability to cause de novo synthesis of gamma-globin by pharmacological manipulation was first shown using 5-azacytidine in experimental animals (DeSimone (1982) *Proc Natl Acad Sci USA* 79(14):4428-31). Subsequent studies confirmed the ability of 5-azacytidine to increase HbF in patients with β-thalassemia and sickle cell disease (Ley, et al. (1982) *N. Engl. J. Medicine,* 307: 1469-1475, and Ley, et al., (1983) *Blood* 62: 370-380). In addition, short chain fatty acids (e.g. butyrate and derivatives) have been shown in experimental systems to increase HbF (Constantoulakis et al. (1988) *Blood* 72(6):1961-1967). There is a segment of the human population with a condition known as 'Hereditary Persistence of Fetal Hemoglobin' (HPFH) where elevated amounts of HbF persist in adulthood (10-40% in HPFH heterozygotes (see Thein et al. (2009) *Hum. Mol. Genet* 18 (R2): R216-R223)). This is a rare condition, but in the absence of any associated beta globin abnormalities, is not associated with any significant clinical manifestations, even when 100% of the individual's hemoglobin is HbF. When individuals that have a beta thalassemia also have co-incident HPFH, the expression of HbF can lessen the severity of the disease. Further, the severity of the natural course of sickle cell disease can vary significantly from patient to patient, and this variability, in part, can be traced to the fact that some individuals with milder disease express higher levels of HbF.

One approach to increase the expression of HbF involves identification of genes whose products play a role in the regulation of γ-globin expression. One such gene is BCL11A, first identified because of its role in lymphocyte development. BCL11A encodes a zinc finger protein that is thought to be involved in the stage specific regulation of γ-globin expression. BCL11A is expressed in adult erythroid precursor cells and down-regulation of its expression leads to an increase in γ-globin expression. See, Sankaran et at (2008) *Science* 322 p. 1839. The protein appears to interact with the β-globin locus to alter its configuration and thus its expression at different developmental stages. In addition, another regulatory protein KLF1 (encoded at chr19: 12995237-12998017), appears to be involved in regulation of γ-globin expression. It has been found that KLF1 levels are directly proportional to BCL11A levels, and both are inversely proportional to γ-globin levels in a Maltese family with persistent expression of HbF that carries a heterozygous mutation of the KLF1 gene (Borg et al, (2011) *Haematologica* 96(5): 635-638). The KLF1 gene product appears to bind directly to the BCL11A gene in vivo, and thus may be responsible for its upregulation (see Borg et al (2010) *Nat Genet* 42(9):801-805; Bieker (2010) *Nat Genet* 42(9): 733-734; Zhou et al. (2010) *Nat Genet* 42(9):742-744). Thus, if KLF1 stimulates BCL11A expression, the action of BCL11A will result in the suppression of γ-globin and HbF production. Use of an inhibitory RNA targeted to the BCL11A gene has been proposed (see, e.g., U.S. Patent Publication No. 20110182867) but this technology has several potential drawbacks, namely that complete knock down may not be achieved, delivery of such RNAs may be problematic and the RNAs must be present continuously, requiring multiple treatments for life. Thus, the methods and compositions of the invention may be used to treat SCD and hemoglobinopathies with a CRISPR/Cas system where the single guide RNA comprises sequences to target the KLF1 or BCL11a genes. Knock out of the KLF1 gene through double strand cleavage may be accomplished through the CRIPSR/Cas system of the invention. Preferred sites for targeting are in exon 1, exon 2 and exon 3 to give the desired knock out of the gene. Especially preferred are the regions on chromosome 19 at or near 12994239-12999017, 12997868-12998017, and 12996131-12996956. Especially preferred is targeting the region of chromosome 19 at or near 12997877-12997912. Non-limiting examples of sequences suitable for targeting are shown in Table 1.

Knock out of the BCL11A gene through double strand cleavage may be accomplished using a CRISPR/Cas system and the sgRNAs of the invention. Preferred is to target the BCL11A gene (chr2:60684329-60780633). Also preferred is to cleave the BCL11A gene in an exonic sequence (e.g. at or near chromosome 2: 60780351-60780633 (exon 1), 60773106-60773435, especially 60773362-60773400 (exon 2), 60695867-60695968 (exon 3), 60687817-60689559 (exon 4), 60678302-60679801 (exon 5)). Especially preferred is targeting the enhancer sequence in the BCL11A gene (see Bauer et al (2013), *Science* 342 (6155):253-7). Thus, targeting sequences at or near chromosome 2 60725317-60725682, 60722125-60722677 and 60718031-60718382 is especially preferred.

Another approach to alter the expression of gamma globin is to target the regulatory sites on the gene encoding gamma globin (HBG1, located on chromosome 11: 5268501-5272087). Preferred is to target the transcriptional start site at or near chromosome 11:5271086-5271087, Especially preferred is to target the so-called "HPFH" region, known because of patients with hereditary persistence of fetal hemoglobin (see Thein et al (2009) *Hum. Mol. Genet* 18 (R2): R216-R223). Thus, targeting sequences at or near chromosome 11:5272286-5272290, 5272263-5272263 and 5272198-5272205 is especially preferred.

Alpha thalassemias are also prevalent in the human population, especially in Asia and some type of alpha globin aberrancy is thought to be the commonest genetic disorder in humans. In the tropical and subtropical areas of the world, alpha globin disorder is found in 80-90% of the population (see Harteveld and Higgs (2010) *Orphanet Journal of Rare Diseases* 5:13).

Humans carry 2 copies of the alpha globin gene in tandem (α1 and α2) on chromosome 16, so in a normal diploid cell there are 4 copies all together. The α2 gene normally accounts for 2-3 times more α-globin mRNA than the α1 gene. The tandem organization of these two genes may be associated with the high prevalence of large deletions in alpha globin genes in alpha thalessemia patients, where generally the number of alpha globin genes that are non-functional relates directly to the severity of any alpha thalessemia (see Chui et al (2003) *Blood* 101(3):791). Deletion of one copy seems to be fairly common (30% of African Americans and 60-80% of people living in Saudi Arabia, India, and Thailand), and is generally not evident in the individual unless genetic testing is done. Deletion of two copies, whether on the same chromosome (cis) or one from each chromosome (trans), may cause the afflicted person to have mild anemia. When three α-globin genes are deleted, such that the individual has only one functioning α-globin gene, moderate anemia is found, but more importantly, the crucial α globin to β globin ratio is disrupted. β4 tetramers, comprising four beta-globin chains, are often observed in patients with only one functional alpha-globin gene, an condition known as HbH. The β4 tetramers are able to bind oxygen but do not release it into the periphery, causing what is known as Hb H disease. Individuals with HbH disease have RBCs with shortened half-lives and which undergo hemolysis easily, leading to increased anemia. Loss of all four α-globin genes is usually fatal in utero. Thus, the methods and compositions of the invention may be used to treat thalassemias with a CRISPR/Cas system where the single guide RNA comprises sequences to target the regulatory region of the alpha globin gene. Non-limiting examples of sequences suitable for targeting are shown in Table 1.

Other exemplary targets include genes encoding receptors, for example viral receptors. When HIV infects human T cells, it relies on association with the T cell receptor CD4 and one of two co-receptors, the chemokine receptor CCR5 or CXCR4, to gain entry into the cell. Natural CCR5 variants ("CCR5-delta 32") in the human population were identified who appear to be resistant to HIV infection, especially in the homozygous state. Thus, to prevent HIV from infecting T cells, and ultimately leading to T cell death and decreased immune function in the HIV infected patient, disruption of one or both of the co-receptors may be accomplished to render the cell resistant to the virus (see U.S. Pat. No. 7,951,925). Currently clinical trials are underway where HIV patient T cells are edited at the CCR5 locus ex vivo to knock out the CCR5 gene. These cells are then re-introduced into the patient to treat HIV. Thus, the methods and compositions of the invention may be used to disrupt CCR5 alleles with a CRISPR/Cas system where the single guide RNA comprises sequences to target a human CCR5 gene (chr3:46411633-46417697), especially at or near the exon region (chr3:46414394-46415452). One especially preferred region for targeting the CCR5 gene for knock out is the region near the delta-32 mutation region (at or near chr3: 46414923-46415020). Another especially preferred region is around the chr3: 46414522-46414643, which encodes part of the second extracellular loop of the CCR5 protein. The region at or near the ATG protein translation initiation site (at or near chr3:46414347-46414466) is also especially preferred for genome modification, such as fusion of a C34 peptide to the N-terminus of CCR5 by targeted integration for anti-HIV therapy. Similar studies are in progress in animal models of CXCR4-dependent HIV where the CXCR4 is selectively disrupted, or disrupted in tandem with CCR5 to prevent HIV infection of T cells (see U.S. Patent Publication No. 20100291048). Thus, the methods and compositions of the invention may be used to disrupt CXCR4 alleles with a CRISPR/Cas system where the single guide RNA comprises sequences to target a human CXCR4 gene (chr2:136871919-136875725), especially at or near the exon 2 region (chr2:136872439-136873482) and the region surrounding the small exon1 (chr2:136875616-136875630). One preferred region for targeting the CXCR4 gene for knock out is the region at or near chr2:136872863-136872982 that is an analog to the delta-32 mutation region in CCR5 gene. The region at or near chr2:136875540-136875687 near the ATG protein translation initiation site of exon1 is especially preferred, and the region at or near chr2:136873389-136873558 near the splicing site of exon2 is especially preferred for gene modification, such as fusion of a C34 peptide to the N-terminus of CXCR4 by targeted integration for anti-HIV therapy. Thus, a sgRNA can be designed to bind to sequences anywhere in the CCR5 or CXCR4 locus, including, but not limited to, a sequence in one or more of these preferred targeting regions.

Another receptor of interest is the glucocorticoid receptor (see U.S. Patent Publication US20080188000). Knock out of this receptor in specific therapeutic treatments allows the use of steroids that are normally taken up by the glucocorticoid receptor. Thus, the receptor may be targeted by a CRISPR/Cas system using the sgRNAs of the invention to target at or near chromosome 5: 142646254-142783254. Especially preferred is to target the exonic sequences, for example, at or near chromosome 5 142646255-142783254 (exon 1), 142782776-142783254 (exon 2), 142779221-142780417, and especially useful 142657496-142658976 (exon 3), 142693567-142693733 (exon 4), 142689662-142689778 (exon 5), 142680050-142680328 (exon 6), 142678233-142678377 (exon 7), 142675025-142675155 (exon 8), 142662133-142662290 (exon 9).

Specific nucleases can also be engineered to insert a peptide fusion inhibitor on to an HIV receptor to prevent HIV infection of T cells (see co-owned US patent publication no. 20120093787), where an example of such a peptide fusion inhibitor is C34 or fuzeon. Similarly HIV can be treated by using engineered nucleases to insert anti-HIV transgenes in safe harbor loci within the cell to combat the virus. Examples of such anti-HIV genes may be selected from the group consisting of a sequence encoding a zinc finger transcription factor that represses an HIV polyprotein, a sequence encoding a zinc finger transcription factor that represses expression of an HIV receptor, a CCR5 ribozyme, an siRNA sequence targeted to an HIV polyprotein, a sequence encoding a Trim5alpha (Trim5α) restriction factor, a sequence encoding an APOBEC3G restriction factor, a sequence encoding a RevM10 protein, a sequence encoding C46, other anti-HIV genes, a suicide cassette and combinations thereof. Thus, the methods and compositions of the invention may be used to treat or prevent HIV with a CRISPR/Cas system where the single guide RNA comprises sequences to target the CCR5 or CXCR4 gene for integration of a suitable anti-HIV transgene. Additional non-limiting examples of sequences suitable for targeting are shown in Table 1.

Genomic editing as described herein may be performed on any endogenous target. In certain embodiments, genomic modifications (e.g., transgene integration) are at a "safe harbor" gene. Specific "safe harbor" locations in the genome may be utilized for transgene integration that may either utilize the promoter found at that safe harbor locus, or allow the expressional regulation of the transgene by an exogenous promoter that is fused to the transgene prior to insertion. Several such "safe harbor" loci have been described, including the AAVS1 (also known as PPP1R12C) and CCR5 genes in human cells, Rosa26 and albumin (see co-owned U.S. Pat. Nos. 9,394,545 and 9,150,847 and U.S. Publication Nos. 20080299580, 20080159996 and 201000218264 and Zp15 in plants (see U.S. Pat. No. 8,329,986)). An exogenous nucleic acid or transgene sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.). The exogenous nucleic acid sequence is introduced into the cell such that it is integrated into the genome of the cell (e.g. the PPP1R12C gene, which lies on chromosome 19, i.e. chr19: 55602840-55624858). Integration of exogenous sequences can proceed through both homology-dependent and homology-independent mechanisms. Thus, the methods and compositions of the invention may be used to insert transgenes into a safe harbor locus with a CRISPR/Cas system where the single guide RNA comprises sequences to target the safe harbor gene. Non-limiting examples of sequences suitable for targeting are shown in Table 1.

As described above, nucleases (e.g., CRISPR/Cas) specific for the safe harbor can be utilized such that the transgene construct is inserted by either HDR- or NHEJ-driven processes. Hypoxanthine-guanine phosphoribosyl-transferase (HPRT) is an enzyme involved in purine metabolism encoded by the HPRT1 gene (chrX:133594175-133634698). HPRT1 is located on the X chromosome, and thus is present in single copy in males. HPRT1 encodes the transferase that catalyzes the conversion of hypoxanthine to inosine monophosphate and guanine to guanosine monophosphate by transferring the 5-phosphorobosyl group from 5-phosphoribosyl 1-pyrophosphate to the purine. The enzyme functions primarily to salvage purines from degraded DNA for use in renewed purine synthesis. In the presence of 6-TG, HPRT is the enzyme responsible for the integration of 6-TG into DNA and RNA in the cell, resulting in blockage of proper polynucleotide synthesis and metabolism. Thus, 6-TG can be used as a selection agent to kill cells with a functional HPRT enzyme, and in addition, 6-TG can be given to cause mild immunoablation in subjects in need thereof. In a patient receiving a stem cell graft (e.g. hematopoietic or progenitor stem cells), a transgene of interest can be integrated into the HPRT locus, knocking out the HPRT1 gene. Such a cell population will be resistant to 6-TG toxicity. Thus when the transgene (+)/HPRT1(−) cells are infused into the patient, a mild course of 6-TG may increase engraftment of the cells, and those cells that engraft will have a greater percentage of transgene integration.

HPRT has been targeted traditionally as a safe harbor for transgene integration (see for example Jasin et al (1996) *Proc Natl Acad Sci USA* 93, p. 8804). It is constitutively expressed at a low level, and disruption of the HPRT gene can be selected for both in vitro and in vivo using 6-TG. However, integration into an HPRT locus via random integration can be difficult and occurs only at a low frequency. Use of specific nucleases will allow improved targeting of the HPRT locus. Thus, the methods and compositions of the invention may be used to insert transgenes into a HPRT locus with a CRISPR/Cas system where the single guide RNA of the invention comprises sequences to target the safe harbor gene. Preferred is targeting the HPRT gene (chrX: 133594175-133634698). Especially preferred is to target sequences in intron 1 (at or near chromosome X: 133597660-133597662, 133603544-133603546 and 133604282-133604284). Also preferred is cleaving in exon 3, especially at or near chromosome x: 133609240-133609242. Another preferred location is in the active domain of the enzyme at or near chromosome X: 133627552-133627554. Thus, a sgRNA can be designed to bind to sequences anywhere in the HPRT locus, including, but not limited to, a sequence in one or more of these preferred targeting regions. Additional non-limiting examples of sequences suitable for targeting are shown in Table 1.

Another useful gene to target with the methods and compositions of the invention is the IL2 receptor common gamma chain (encoded by the IL2RG gene, at or near chrX:70327254-70331481). The IL2RG protein is the common receptor chain in several cytokine receptors, and mutations in this gene are associated with X-linked severe combined immunodeficiency ("X-SCID"). Thus, targeting this gene with a CRISPR/Cas system and the sgRNAs of the invention to facilitate gene correction would be beneficial to X-SCID patients. Preferred is to target near the end of exon 1 (at or near Chr x: 70331274-70331276). Especially preferred is to target intron 1 at or near chromosome x: 70331196-70331198, or in exon 5, at or near chromosome x: 70329158-70329160.

The albumin gene is highly expressed in the liver. Thus, insertion of a transgene into the endogenous albumin locus using a specific nuclease results in high level expression of the protein or gene product encoded by that transgene, which may also be secreted into the blood stream The transgene can encode any protein or peptide including those providing therapeutic benefit. For example, the transgene can encode a protein involved in disorders of the blood, for example, clotting disorders, and a variety of other monogenic diseases. The transgene can be inserted into the endogenous albumin locus such that expression of the transgene is controlled by the albumin expressional control elements, resulting in liver-specific expression of the transgene encoded protein at high concentrations. Proteins that may be expressed may include clotting factors such as Factor VII, Factor VIII, Factor IX, Factor X, Factor XI, Factor XIII, vWF and the like, antibodies, proteins relevant to lysosomal storage, insulin, alpha 1-antitrypsin, and indeed any peptide or protein that when so expressed provides benefit. Thus, the methods and compositions of the invention may be used to insert transgenes into an albumin gene with a CRISPR/Cas system where the single guide RNA comprises sequences to target the albumin gene (at or near chr4:74269972-74287129). Preferred targets are those in the exonic sequences, for example at or near chr:4 74270073-74270883 (exon 1, especially preferred, most preferred at chromosome 4: 74270385-74270485), 74270840-74272396 (exon 2, especially preferred at or near chromosome 4: 74270840-74272396), 74272428-74274361 (exon 3), 74274472-74275122 (exon 4), 74275154-74276079 (exon 5), 74276076-74277763 (exon 6), 74277792-74279187 (exon 7), 74279301-74280802 (exon 8), 74280834-74282023 (exon 9), 74282020-74283298 (exon 10), 74283336-74283855 (exon 11), 74283978-74285274 (exon 12, especially preferred), 74285306-74286021 (exon 13, especially preferred), and 74285988-74286859 (exon 14, especially preferred). Thus, a sgRNA can be designed to bind to sequences anywhere in the albumin locus, including, but not limited to, a sequence in one or more of these preferred targeting regions. Additional non-limiting examples of sequences suitable for targeting are shown in Table 1.

Lysosomal storage diseases (LSDs) are a group of rare metabolic monogenic diseases characterized by the lack of functional individual lysosomal proteins normally involved in the breakdown of waste lipids, glycoproteins and mucopolysaccharides. These diseases are characterized by a buildup of these compounds in the cell since it is unable to process them for recycling due to the mis-functioning of a specific enzyme. The most common examples are Gaucher's (glucocerebrosidase deficiency—gene name: GBA), Fabry's (α galactosidase deficiency—GLA), Hunter's (iduronate-2-sulfatase deficiency-IDS), Hurler's (alpha-L iduronidase deficiency—IDUA), and Niemann-Pick's (sphingomyelin phosphodiesterase 1deficiency—SMPD1) diseases. When grouped all together, LSDs have an incidence in the population of about 1 in 7000 births. These diseases have devastating effects on those afflicted with them. They are usually first diagnosed in babies who may have characteristic facial and body growth patterns and may have moderate to severe mental retardation. Treatment options include enzyme replacement therapy (ERT) where the missing enzyme is given to the patient, usually through intravenous injection in large doses. Such treatment is only to treat the symptoms and is not curative, thus the patient must be given repeated dosing of these proteins for the rest of their lives, and potentially may develop neutralizing antibodies to the injected protein. Often these proteins have a short serum half-life, and so the patient must also endure frequent infusions of the protein. For example, Gaucher's disease patients receiving the Cerezyme® product (imiglucerase) must have infusions three times per week. Production and purification of the enzymes is also problematic, and so the treatments are very costly (>$100,000 per year per patient). Thus, the specific nucleases of the invention may be used to insert genes encoding the missing wild type versions of the proteins involved in lysosomal storage diseases into safe harbor loci such as albumin for expression and treatment of the LSD.

Hemophilia B is a genetic disorder of the blood-clotting system, characterized by bleeding into joints and soft tissues, and by excessive bleeding into any site experiencing trauma or undergoing surgery. While hemophilia B is clinically indistinguishable from hemophilia A, factor VIII (FVIII) is deficient or absent in hemophilia A and factor IX (FIX or F.IX) is deficient or absent in patients with hemophilia B. Factor IX encodes one of the serine proteases involved with the coagulation system, and it has been shown that restoration of even 3% of normal circulating levels of wild type Factor IX protein can prevent spontaneous bleeding.

Gene therapy, including liver-directed gene therapy protocols and direct intramuscular injection, involving the introduction of plasmid and other vectors (e.g., AAV) encoding a functional FIX protein have been described for treatment of hemophilia B. See, e.g., U.S. Pat. No. 6,936,243; Lee et al. (2004) *Pharm. Res.* 7:1229-1232; Graham et al. (2008) *Genet Vaccines Ther.* 3:6-9. However, in these protocols, the formation of inhibitory anti-factor IX (anti-FIX) antibodies and antibodies against the delivery vehicle remains a major complication of FIX protein replacement-based treatment for hemophilia B. Thus, use of designed nucleases and related technology to either correct the endogenous Factor VIII or Factor IX gene or introduce a wild type copy of the gene in a safe harbor locus can restore clotting activity in a treated patient. A preferred targeting region for the Factor VIII gene is at or near the gene sequence located at chrX:154064064-154250998. Especially preferred for targeting the Factor VIII gene is the region of intron 22, which is a site of common inversion evens that account for up to 50% of FVIII mutations in severe hemophilia A patients, located at or near chrX:154091503-154124351. For the Factor IX (F.IX) gene, preferred for targeting is the gene sequence located at or near chrX:138,612,895-138,645,617. Especially preferred are targets in regions in intron 1, e.g. at or near chrX:138613760-138613816, chrX:138618832-138618887 and/or chrX:138613815-138613872. Thus, a sgRNA can be designed to bind to sequences anywhere in the Factor VIII or Factor IX loci, including, but not limited to, a sequence in one or more of these preferred targeting regions.

Parkinson's disease (PD) is a neurodegenerative disease that afflicts approximately 4-6 million people worldwide. In the United States, approximately one to two hundred people per 100,000 have PD. The prevalence of PD increases in the older population, with approximately 4% of people over the age of 80 suffering from this disease (Davie (2008) *Brit Med Bull* 86(1) p. 109), although 10% of patients are under 40 years of age (Kumari (2009) *FEBS J.* 276(22) p. 6455).

It appears that many factors can play a role in disease onset and/or progression of PD. For example, genetic mutations in the leucine rich repeat kinase 2 gene (LRRK2, also known as PARK8) has been identified to be involved in both familial and sporadic forms of PD. In fact, studies suggest that LRRK2 mutations may be responsible for between 5 and 13% of familial PD, and from 1 to 5% of sporadic PD. The protein itself is a large (>280 kD) multidomain protein containing the following known domains: armadillo (ARM), ankryn (ANK), LRR, Ras of complex proteins (ROC), C-terminal of ROC (COR), mitogen-activated protein kinase kinase kinase and WD40. Thus, LRRK2 contains several protein-protein interactive domains (ARM/ANK, LRR and WD40) suggesting that LRRK2 plays a role in protein complex formation (Kumari, ibid). Several clusters of mutations have been identified which fall across its length of the gene, with the majority of pathological mutations clustering in the enzymatic domains of the protein.

Specifically, the LRRK2 mutation G2019S has been suggested to play an important role in PD in some ethnicities. The mutation is autosomal dominant and the lifetime penetrance for the mutation has been estimated at 31.8%. The SNP responsible for this missense mutation in patients is annotated as rs34637584 in the human genome, and is a G to A substitution at the genomic level (6055G>A). This LRRK2 mutation can be referred to either as G2019S or 6055G>A and is found at or near chr12:40734202. The G2019S mutation has been shown to increase LRRK2 kinase activity, and is found in the within the activation domain or protein kinase-like domain of the protein (Luzon-Toro (2007) *Hum Mol Genet* 16(17) p. 2031). Thus, a specific nuclease can be used to correct a mutation in the LRRK2 gene for the treatment of PD. Thus, the methods and compositions of the invention may be used to correct a LRRK2 gene with a CRISPR/Cas system where the single guide RNA comprises sequences to target the LRRK2 gene. Especially preferred is a sgRNA designed to target at or near chr12:40734202-40734202. Non-limiting examples of sequences suitable for targeting are shown in Table 1.

Trinucleotide repeat expansion disorders were first characterized in the early 1990s (see Di Prospero and Fischbeck, (2005) *Nature Reviews Genetics* vol 6: 756-765). These disorders involve the localized expansion of unstable repeats of sets of three nucleotides and can result in loss of function of the gene in which the repeat resides, a gain of toxic function, or both. Trinucleotide repeats can be located in any part of the gene, including non-coding and coding gene regions. Repeats located within the coding regions typically involve either a repeated glutamine encoding triplet (CAG) or an alanine encoding triplet (CGA). Expanded repeat regions within non-coding sequences can lead to aberrant expression of the gene while expanded repeats within coding regions (also known as codon reiteration disorders) may cause mis-folding and protein aggregation.

Huntington's Disease (HD), also known as Huntington's Chorea, is a progressive disorder of motor, cognitive and psychiatric disturbances The mean age of onset for this disease is age 35-44 years, although in about 10% of cases, onset occurs prior to age 21, and the average lifespan post-diagnosis of the disease is 15-18 years. Prevalence is about 3 to 7 among 100,000 people of western European descent. The disease is associated with expansion of the CAG repeat region in the endogenous Huntintin gene (Htt, chr4:3076237-3245687). Normal Htt alleles contain 15-20 CAG repeats, while alleles containing 35 or more repeats can be considered potentially HD causing alleles and confer risk for developing the disease. Alleles containing 36-39 repeats are considered incompletely penetrant, and those individuals harboring those alleles may or may not develop the disease (or may develop symptoms later in life) while alleles containing 40 repeats or more are considered completely penetrant and no asymptomatic persons containing HD alleles with this many repeats have been reported. Those individuals with juvenile onset HD (<21 years of age) are often found to have 60 or more CAG repeats. Thus, the methods and compositions of the invention may be used to disrupt a Htt allele with a CRISPR/Cas system where the single guide RNA comprises sequences to target the expanded Htt gene. Especially preferred is targeting chromosome 4, at or near 3071604-3081660. The methods and compositions of the invention may also be used to selectively repress a mutant Htt allele using a CRISPR/Cas system fusion protein comprising a repression domains. Non-limiting examples of sequences suitable for targeting are shown in Table 1.

Retinitis pigmentosa (RP) refers to a diverse group of hereditary diseases affecting two million people worldwide that lead to incurable blindness. RP is one of the most common forms of inherited retinal degeneration, and there are multiple genes whose mutation can lead to RP. More than 100 mutations in 44 genes expressed in rod photoreceptors have thus far been identified, accounting for 15% of all types of retinal degeneration, most of which are missense mutations and are usually autosomal dominant.

Rhodopsin is a pigment of the retina that is involved in the first events in the perception of light. It is made of the protein moiety opsin covalently linked to a retinal cofactor. Rhodopsin is encoded by the RHO gene (chr3:129247482-129254187), and the protein has a molecular weight of approximately 40 kD and spans the membrane of the rod cell. The retinal cofactor absorbs light as it enters the retina and becomes photoexcited, causing it to undergo a change in molecular configuration, and dissociates from the opsin. This change initiates the process that eventually causes electrical impulses to be sent to the brain along the optic nerve. In relation to RP, more than 80 mutations in the rhodopsin gene have been identified that account for 30% of all Autosomal Dominant Retinitis Pigmentosa (ADRP) in humans (Dryja et al (2000) *Invest Opthalmol Vis Sci* 41: 3124-3127). Three point mutations in the human rhodopsin gene (leading to P23H, Q64X and Q344X in the protein sequence) are known to cause ADRP in humans. See, e.g., Olsson et al. (1992) *Neuron* 9(5):815-30. The P23H mutation is the most common rhodopsin mutation in the United States. Due to problems with protein folding, P23H rhodopsin only partially reconstitutes with retinal in vitro (Liu et al (1996) *Proc Nat'l Acad Sci* 93:4554-4559), and mutant rhodopsin expressed in transgenics causes retinal degeneration (Goto et al (1995) *Invest Opthalmol Vis Sci* 36:62-71). Thus, the methods and compositions of the invention may be used to disrupt a RHO allele with a CRISPR/Cas system where the single guide RNA comprises sequences to target a human RHO gene (at or near chr3:129247482-129254187). Targeting RHO at specific locations is useful for facilitating gene correction. Preferred target locations include exon 1 (at or near chr3:129247577-129247937 for correcting the sequence associated with the P23H or Q64X mutations), and exon5 (at or near chr3:129251376-129251615). Non-limiting examples of sequences suitable for targeting are shown in Table 1.

Lung diseases, including inherited disorders such as Cystic Fibrosis (CF) and Surfactant Protein B (SP-B) Deficiency remain an issue in pediatric populations. SP-B deficiency is a rare lung disease where protein and fat molecules accumulate in the distant parts of the lungs and affect breathing. The disease is caused by a deficiency of the lung surfactant protein B, primarily due to a defect in the SFTPB gene (located at or near chr2:85884440-85895374) which encodes the pulmonary-associated surfactant B protein (SPB), an amphipathic surfactant protein essential for lung function and homeostasis after birth. The most common mutation in SP-B deficiency is a mutation designated "121ins2" which results in the nucleotide "C" at position 131 in the mRNA being converted into "GAA" (in the genomic sequence, this corresponds to 375C-GAA and is located in exon 4). Thus, the methods and compositions of the invention can be used to targets a CRISPR/Cas system using a sgRNA of the invention to the SFTPB gene at or near chr2:85884440-85895374, and most preferably, to exon 4 (at or near chr2:85893740-85893865).

CF is an autosomal recessive disorder affecting 1 in 1500 to 4000 live births, and is one of the most common inherited pediatric disorders. The primary defect in CF is in the regulation of epithelial chloride transport by a chloride channel protein encoded by the cystic fibrosis transmembrane conductance regulator (CFTR) gene (located chr7: 117120017-117308718). See, e.g., Kerem et al. (1989) *Science* 245:1073-1080; Kreda et al. (2005) *Mol Biol Cell* 16:2154-2167. About 70% of mutations observed in CF patients result from deletion of three base pairs in CFTR's nucleotide sequence, resulting in the loss of the amino acid phenylalanine located at position 508 in the protein (a mutation referred to as ΔF508, (located in exon 11). In a wild type genome, amino acid 507 is an isoleucine, and is encoded by the codon TAG where the G is nucleotide 1652 in the gene. Amino acid 508 is a phenylalanine, encoded by AAA. In the Δ508 mutation, the G from the 507 codon is deleted along with the first two As of the 508 codon, such that the mutation has the sequence TAA at the deleted 507-508 encoding position. TAA also encodes an isoleucine, but the phenylalanine at wild type position 508 is lost. For the ΔI507 deletion, either the isoleucine at position 506 or 507 is deleted. For this mutation, the nucleotides at 1648-1650 or 1651-1653 are lost, or some combination thereof to result in only one isoleucine in the resultant protein. Compound (heterozygous) mutations (ΔF508 and ΔI507) have also been documented. See, e.g., Orozco et al. (1994) *Am J Med Genet.* 51(2):137-9. CF patients, either compound heterozygous ΔI507/ΔF508 or homozygous ΔF508/ΔF508, fail to express the fully glycosylated CFTR protein and the partially glycosylated protein is not expressed on the cell surface (see, e.g., Kreda et al. (2005) *Mol Biol Cell* 16:2154-2167; Cheng et al. (1990) *Cell* 63:827-834) as is required for CFTR function. Individuals bearing either the ΔI507 or ΔF508 CFTR mutations at only one allele (i.e. wt/ΔI507 or wt/ΔF508) are CF carriers and exhibit no defects in lung cell function. See, e.g., Kerem et al. (1990) *Proc Natl Acad Sci USA* 87:8447-8451. Thus, the methods and compositions of the invention may be used to disrupt or correct a CFTR allele with a CRISPR/Cas system where the single guide RNA comprises sequences to target a human CFTR gene. Especially preferred for targeting is at or near chr7:117227793-117227887). Non-limiting examples of sequences suitable for targeting are shown in Table 1.

Muscular dystrophies are diseases that are characterized by a progressive degeneration and weakening of muscle groups. One well known muscular dystrophy is Duchenne's muscular dystrophy, which is an X-linked disease that afflicts 1 in every 3500 boys. It is caused by the lack of the protein dystrophin in the individual muscle cells, and symptoms first appear when the child is approximately 3 years old, and depending on the severity of the disease, death can occur when the patient is in his twenties. The gene encoding dystrophin, DMD (located at or near chrX:31137345-33229673), is extremely large and covers 2.4 megabases of DNA comprising 79 exons that encode a 14 kb mRNA. In patients that lack functional dystrophin, approximately 40% have point mutations that cause a frameshift in the coding sequence such that during translation, a premature stop is encountered resulting in the production of a truncated or non-functioning protein. The other 60% have large insertions or deletions that also result in alteration of frame and similarly result in production of a non-functional protein (Nowak and Davies (2004) *EMBO Reports* 5(9): 872-876). Patients with non-functional dystrophin have the most severe disease, which is also known as Duchenne's Muscular Dystrophy (DMD). Other patients, whose mutations are characterized by gene deletions of regions that encode internal portions of dystrophin, resulting in less functional dystrophin protein as compared to wild type, may have less severe disease, which is called Becker Muscular Dystrophy (BMD). BMD patients have been known to live into their 50's. Targeting the DMD gene may be useful for gene correction of point mutations or for changing splicing patterns of the mRNA transcript, allowing the cell to produce a functional dystrophin protein. Thus, a sgRNA can be designed to bind to sequences anywhere in the DMD locus, at or near chrX:31137345-33229673. Adoptive immunotherapy is the practice of achieving highly specific T cell stimulation of a certain subpopulation of CTLs that possess a high-avidity TCR to the tumor antigen, stimulating and expanding them ex vivo, and then introducing them into the patient. Adoptive immunotherapy is particularly effective if native lymphocytes are removed from the patient before the infusion of tumor-specific cells. The idea behind this type of therapy is that if the introduced high-avidity CTLs are successful, once the tumor has been cleared, some of these cells will remain as memory T cells and will persist in the patient in case the cancer reappears. However, transfer of any TCR transgenes into host T cells carries with it the caveats associated with most gene transfer methods, namely, unregulated and unpredictable insertion of the TCR transgene expression cassette into the genome, often at a low level. Such poorly controlled insertion of the desired transgene can result in effects of the transgene on surrounding genes as well as silencing of the transgene due to effects from the neighboring genes. In addition, the endogenous TCR genes that are co-expressed in the T cell engineered with the introduced TCR transgene could cause undesired stimulation of the T cell by the antigen recognized by the endogenous TCR, undesired stimulation of the T cell by unintended antigens due to the mispairing of the TCR transgene with the endogenous TCR subunits creating a novel TCR complex with novel recognition properties, or can lead to suboptimal stimulation against the antigen of interest by the creation of inactive TCRs due to heterodimerization of the transgene encoded TCR subunits with the endogenous TCR proteins. In fact, the risk of severe autoimmune toxicity resulting from the formation of self-reactive TCR from mispairing of endogenous and exogenous chains has been recently highlighted in a murine model (Bendle et al. (2010) *Nature Medicine* 16:565-570) and in human cells (van Loenen et al. (2010) *Proc Natl Acad Sci USA* 107:10972-7). Additionally, the tumor-specific TCR may be expressed at suboptimal levels on the cell surface, due to competition with the endogenous and mispaired TCR for the CD3 molecules, required to express the complex on the cell surface. Low TCR expression affects the avidity and efficacy of the transgenic T cell. Examples of targets that can be used to make high affinity TCRs against for introduction into a T cell are WT1 and NYEso. Thus, the methods and compositions of the invention may be used to disrupt or correct an endogenous TCR gene with a CRISPR/Cas system where the single guide RNA comprises sequences to target a human TCR alpha (TRAC or TCRA, located at or near chr6:42883727-42893575) or beta (TRBC or TCRB, located at or near chr7:142197572-142198055) gene. Non-limiting examples of sequences suitable for targeting are shown in Table 1.

The programmed death receptor (PD1 or PD-1, also known as PDCD1) has been shown to be involved in regulating the balance between T cell activation and T cell tolerance in response to chronic antigens. Upon T cell activation, PD1 expression is induced in T cells. The ligands for the PD1 receptor are PD1 ligand (PDL1 also known as B7-H1 and CD272) and PDL2 (also known as B7-DC and CD273), and are normally expressed in antigen presenting cells and in the periphery. PD1-PDL (PD1 ligand) coupling causes deactivation of the T cell and is involved in inducing T cell tolerance (see Pardoll (2012) *Nat Rev* 12:252). During HIV1 infection, expression of PD1 has been found to be increased in CD4+ T cells, and PDL1 expression is increased on antigen presenting cells (APCs), tipping the balance between T cell inhibition and T cell stimulation towards T cell inhibition (see Freeman et al (2006) *J Exp Med* 203 (10):2223-2227). It is thought that PD1 up-regulation is somehow tied to T cell exhaustion (defined as a progressive loss of key effector functions) when T cell dysfunction is observed in the presence of chronic antigen exposure as is the case in HIV infection. PD1 up-regulation may also be associated with increased apoptosis in these same sets of cells during chronic viral infection (see Petrovas et al, (2009) *J Immunol.* 183(2):1120-32). PD1 may also play a role in tumor-specific escape from immune surveillance. It has been demonstrated that PD1 is highly expressed in tumor-specific cytotoxic T lymphocytes (CTLs) in both chronic myelogenous leukemia (CML) and acute myelogenous leukemia (AML). PD1 is also up-regulated in melanoma infiltrating T lymphocytes (TILs) (see Dotti (2009) *Blood* 114 (8): 1457-58). Tumors have been found to express the PD1 ligand PD-L1 or, more rarely, the PD1 ligand PDL2 which, when combined with the up-regulation of PD1 in CTLs, may be a contributory factor in the loss in T cell functionality and the inability of CTLs to mediate an effective anti-tumor response. Researchers have shown that in mice chronically infected with lymphocytic choriomeningitis virus (LCMV), administration of anti-PD1 antibodies blocked PD1-PDL interaction and was able to restore some T cell functionality (proliferation and cytokine secretion), leading to a decrease in viral load (Barber et al (2006) *Nature* 439(9): 682-687). Additionally, a fully human PD-1 specific IgG4 monoclonal antibody has been tested in the clinic in an oncology setting on patients with a variety of disease backgrounds (advanced melanoma, renal cell carcinoma, non-small cell lung cancer, colorectal cancer or prostate cancer). Clinical activity was observed in melanoma, renal cell and non-small cell lung cancer patients and preliminary data suggested that detection of PD1 ligand expression by the tumor prior to treatment correlated with clinical outcome (see Wolfe (2012) *Oncology Business Review*, July; and Pardoll, ibid). Thus, the methods and compositions of the invention may be used to disrupt a PD1 allele with a CRISPR/Cas system where the single guide RNA comprises sequences to target a human PD1 gene (chr2:242792033-242801058). One preferred region for targeting the PD1 gene for knock out is at or near the region near that ATG protein translation initiation site. This corresponds to nucleotides chr2: 242800981-242800982 of the PD1 gene. Especially preferred are target sites the PD1 gene where the PAM position for the *S. pyogenes* Cas9 is located at or near chromosome 2 at position 242800980-242800981, 242800975-242800976, 242800971-242800972, 242800970-242800971, 242800967-242800968, and 242800965-242800966. Another especially preferred targeting location is around the region near the PD-1 ligand binding domain (chromosome 2, nucleotides 242794834-242794835 and 242794828-242794829). Another preferred region for targeting is at or near the region near the immunoreceptor tyrosine-based switch motif (e.g., chromosome 2 242793349-242793350, 242793338-242793339, 242793330-242793331 or 242793327-242793328). Mutations in this region disable PD1 function. Especially preferred are target sites for the *S. pyogenes* Cas9 protein at positions at or near chromosome 2: 242800953-242800979, 242794976-242795005, 242794416-242794444 and 242793405-242793433. A preferred targeting region for the Factor VIII gene is at or near the gene sequence located at chrX:154064064-154250998. Especially preferred for targeting the Factor VIII gene is the region of intron 22, which is a site of common inversion evens that account for up to 50% of FVIII mutations in severe hemophilia A patients, located at or near chrX:154091503-154124351. For the Factor IX (F.IX) gene, preferred for targeting is the gene sequence located at or near chrX:138,612,895-138,645,617. Especially preferred are targets in regions in intron 1, e.g. at or near chrX:138613760-138613816, chrX:138618832-138618887 and/or chrX:138613815-138613872. Thus, a sgRNA can be designed to bind to sequences anywhere in the PD1 locus, including, but not limited to, a sequence in one or more of these preferred targeting regions. Non-limiting examples of sequences suitable for targeting are shown in Table 1.

Another modulator of T cell activity is the CTLA-4 receptor. Similar to the T cell receptor CD28, CTLA-4 interacts with the CD80 and CD86 ligands on antigen presenting cells. But while interaction of these antigens with CD28 causes activation of T cells, interaction of CD80 or CD86 with CTLA-4 antagonizes T-cell activation by interfering with IL-2 secretion and IL-2 receptor expression, and by inhibiting the expression of critical cell cycle components. CTLA-4 is not found on the surface of most resting T cells, but is upregulated transiently after T-cell activation. Thus CTLA-4 is also involved in the balance of activating and inhibiting T cell activity (see Attia et al (2005) *J Clin Oncol.* 23(25): 6043-6053). Initial clinical studies involving the use of CTLA 4 antibodies in subjects with metastatic melanoma found regression of the disease (Attia, ibid), but later studies found that subject treated with the antibodies exhibited side effects of the therapy (immune-related adverse events: rashes, colitis, hepatitis etc.) that seemed to be related to a breaking of self-tolerance. Analysis of this data suggested that greater tumor regression as a result of the anti-CTLA4 antibody correlated directly with a greater severity of immune-related adverse events (Weber (2007) *Oncologist* 12(7): 864-872). Thus, the methods and compositions of the invention may be used to disrupt a CTLA-4 gene with a CRISPR/Cas system where the single guide RNA comprises sequences to target a human CTLA-4 gene, located at or near chr2:204732511-204738683. Non-limiting examples of sequences suitable for targeting are shown in Table 1.

Chimeric Antigen Receptors (CARs) are molecules designed to target immune cells to specific molecular targets expressed on cell surfaces. In their most basic form, they are receptors introduced to a cell that couple a specificity domain expressed on the outside of the cell to signaling pathways on the inside of the cell such that when the specificity domain interacts with its target, the cell becomes activated. Often CARs are made from variants of T-cell receptors (TCRs) where a specificity domain such as a scFv or some type of receptor is fused to the signaling domain of a TCR. These constructs are then introduced into a T cell allowing the T cell to become activated in the presence of a cell expressing the target antigen, resulting in the attack on the targeted cell by the activated T cell in a non-MHC dependent manner (see Chicaybam et al (2011) *Int Rev Immunol* 30:294-311). Currently, tumor specific CARs targeting a variety of tumor antigens are being tested in the clinic for treatment of a variety of different cancers. Examples of these cancers and their antigens that are being targeted includes follicular lymphoma (CD20 or GD2), neuroblastoma (CD171), non-Hodgkin lymphoma (CD20), lymphoma (CD19), glioblastoma (IL13Rα2), chronic lymphocytic leukemia or CLL and acute lymphocytic leukemia or ALL (both CD19). Virus specific CARs have also been developed to attack cells harboring virus such as HIV. For example, a clinical trial was initiated using a CAR specific for Gp100 for treatment of HIV (Chicaybam, ibid).

As useful as it is to develop a technology that will cause a T cell to re-direct its attention to specific cells such as cancer cells, there remains the issue that these target cells often express of PD-1 ligand. As such, the PD1-PD-L1/PD-L2 interaction enables the tumor to escape action by the CAR-targeted T cell by deactivating the T cells and increasing apoptosis and cell exhaustion. Additionally, the PD1-PDL interactions are also involved in the repression of the T cell response to HIV, where increased expression of both PD1 and PDL leads to T cell exhaustion. Induction of CTLA-4 expression on activated T cells is also one of the first steps to damping the immune response, and thus a T cell armed with a CAR might become inactive due to the engagement of this system designed to balance T cell activation with T cell inhibition. Thus, the CRISPR/Cas system of the invention can be used with the sgRNAs of the invention described above to knockout CTLA-4 and/or PD1 in a T cell comprising a CAR.

MHC antigens were first characterized as proteins that played a major role in transplantation reactions. Rejection is mediated by T cells reacting to the histocompatibility antigens on the surface of implanted tissues, and the largest group of these antigens is the major histocompatibility antigens (MHC). MHC proteins are of two classes, I and II. The class I MHC proteins are heterodimers of two proteins, the α chain, which is a transmembrane protein encoded by the MHC1 gene, and the β2 microblogulin chain, which is a small extracellular protein that is encoded by a gene that does not lie within the MHC gene cluster. The α chain folds into three globular domains and when the β2 microglobulin chain is associated, the globular structure complex is similar to an antibody complex. The foreign peptides are presented on the two most N-terminal domains which are also the most variable. Class II MHC proteins are also heterodimers, but the heterodimers comprise two transmembrane proteins encoded by genes within the MHC complex. The class I MHC:antigen complex interacts with cytotoxic T cells while the class II MHC presents antigens to helper T cells. In addition, class I MHC proteins tend to be expressed in nearly all nucleated cells and platelets (and red blood cells in mice) while class II MHC protein are more selectively expressed. Typically, class II MHC proteins are expressed on B cells, some macrophage and monocytes, Langerhans cells, and dendritic cells.

The class I HLA gene cluster in humans comprises three major loci, B, C and A, as well as several minor loci. HLA-A, HLA-B and HLA-C are the HLA class I heavy chain paralogues. The class I molecule is a heterodimer consisting of a MHC alpha heavy chain (HLA-A, HLA-B or HLA-C) and a light chain (beta-2 microglobulin). The heavy chain is anchored in the membrane. Class I molecules play a central role in the immune system by presenting peptides derived from the endoplasmic reticulum lumen. The heavy chain is approximately 45 kDa and its gene contains 8 exons. Exon 1 encodes the leader peptide, exons 2 and 3 encode the alpha1 and alpha2 domains, which both bind the peptide, exon 4 encodes the alpha3 domain, exon 5 encodes the transmembrane region, and exons 6 and 7 encode the cytoplasmic tail. Polymorphisms within exon 2 and exon 3 are responsible for the peptide binding specificity of each class one molecule. A preferred region for targeting an sgRNA in HLA-A, B or C is within the gene sequence, (e.g. chr6:29910247-29912868 for HLA-A, chr6:31236526-31239913 for HLA-B, and chr6:31236526-31239125 for HLA-C). Especially preferred is targeting sequences within the leader sequence (e.g., at or near chr6:31324936-31324989 for HLA-B), the alpha 1 and alpha 2 domains (e.g. at or near chr6:31324863-31324935 and chr6:31324735-31324862, respectively for HLA-B) and the alpha3 domain (e.g. at or near chr6:31324465-31324734 for HLA-B).

The class II HLA cluster also comprises three major loci, DP, DQ and DR, and both the class I and class II gene clusters are polymorphic, in that there are several different alleles of both the class I and II genes within the population. HLA-DPA1, HLA-DQA1 and HLA-DRA belong to the HLA class II alpha chain paralogues. This class II molecule is a heterodimer consisting of an alpha (DPA) and a beta (DPB) chain, both anchored in the membrane. They play a central role in the immune system by presenting peptides derived from extracellular proteins. Class II molecules are expressed in antigen presenting cells (APC: B lymphocytes, dendritic cells, macrophages). The alpha chains are approximately 33-35 kDa and their genes (chr6_ssto_hap7:3,754,283-3,759,493 for HLA-DRA, chr6:32605183-32611429 for HLA-DQ and chr6:33032346-33048555 for HLA-DPA) contain 5 exons. Exon one (e.g. at or near chr6:33041248-33041347 for HLA-DPA1) encodes the leader peptide, exons 2 and 3 (e.g. at or near chr6:33037418-33037663 and chr6:33036796-33037077 for HLA-DPA1) encode the two extracellular domains, exon 4 (e.g. at or near hr6:33036427-33036581 for HLA-DPA1) encodes the transmembrane domain and the cytoplasmic tail. Thus, especially preferred regions to target with a CRIPSR-Cas system of the invention are within exons one, two and three. Within the DP molecule both the alpha chain and the beta chain contain the polymorphisms specifying the peptide binding specificities, resulting in up to 4 different molecules. Thus, a sgRNA can be designed to bind to sequences anywhere in the HLA-DPA1, HLA-DQ1 or HLA-DRA loci, including, but not limited to, a sequence in one or more of these preferred targeting regions.

There are also several accessory proteins that play a role in HLA functioning as well. The Tap1 (encoded at chr6:32812986-32821748) and Tap2 (encoded at chr6:32793187-32806547) subunits are parts of the TAP transporter complex that is essential in loading peptide antigens on to the class I HLA complexes, and the LMP2 and LMP7 proteosome subunits play roles in the proteolytic degradation of antigens into peptides for display on the HLA. Reduction in LMP7 (chr6_dbb_hap3:4089872-4093057) has been shown to reduce the amount of MHC class I at the cell surface, perhaps through a lack of stabilization (see Fehling et al (1999) *Science* 265:1234-1237). In addition to TAP and LMP, there is the tapasin gene (chr6:33271410-33282164), whose product forms a bridge between the TAP complex and the HLA class I chains and enhances peptide loading.

Reduction in tapasin results in cells with impaired MHC class I assembly, reduced cell surface expression of the MHC class I and impaired immune responses (see Grandea et al (2000) *Immunity* 13:213-222 and Garbi et al (2000) *Nat Immunol* 1:234-238). Regulation of class II MHC expression is dependent upon the activity of the MHCII enhanceosome complex. The enhanceosome components (one of the most highly studied components of the enhanceosome complex is the RFX5 gene product (see Villard et al (2000) *MCB* 20(10): 3364-3376)) are nearly universally expressed and expression of these components does not seem to control the tissue specific expression of MHC class II genes or their IFN-γ induced up-regulation. Instead, it appears that a protein known as CIITA (class II transactivator) which is a non-DNA binding protein, serves as a master control factor for MCHII expression. In contrast to the other enhanceosome members, CIITA does exhibit tissue specific expression, is up-regulated by IFN-γ, and has been shown to be inhibited by several bacteria and viruses which can cause a down regulation of MHC class II expression (thought to be part of a bacterial attempt to evade immune surveillance (see Leibund Gut-Landmann et al (2004) *Eur. J. Immunol* 34:1513-1525)). Thus, the methods and compositions of the invention may be used to disrupt an HLA gene or an HLA regulatory gene with a CRISPR/Cas system where the single guide RNA comprises sequences to target a human HLA gene or HLA regulatory gene. A sgRNA can be designed to bind to sequences anywhere in the HLA locus, including, but not limited to, a gene sequence encoding HLA-A, HLA-B, HLA-C, HLA-DPA, HLA-DQ or HLA-DRA, and to preferred targeting regions within these genes discussed above. Additionally, sgRNAs can be designed to bind to sequences in genes whose products interact with the MHC proteins, including TAP1, TAP2, LMP2, LMP7, and tapasin, or to sequences in genes whose products regulate the expression of these genes, including those in the MHCII enhanceosome complex (RFX5 (chr1:151313116-151319769) and CIITA (chr16:10971055-11002744).

The methods and compositions of the invention can be used to alter the expression of one or more genes in a cell wherein those genes are related to a nervous system disease. The cells may be modified in vivo or ex vivo (i.e., isolated cells, including patient derived cells, patient derived induced pluripotent stem cells or isolated stem cells) can be modified and re-introduced into a subject with the nervous system disease. For example, for the treatment or prevention of Alzheimer's disease, alteration of the expression of the Tau gene and/or an allele of ApoE (e.g., ApoE4) may be beneficial. Alzheimer's Disease (AD) pathogenesis is thought to be triggered by accumulation of the amyloid beta peptide due to over production of this protein and failure of its natural clearance mechanisms. Amyloid beta self-aggregates and accumulates in plaques thought to be synaptotoxins. The plaques also may interfere with phosphorylation of tau, leading to its hyperphosphorylation and loss of normal function. Tau is a microtubule associated protein involved in axonal transport, and an alteration of its normal function leads to accumulation of neurofibrillary tangles (Medeiros et al, (2011) *CNS Neurosci Ther* 17(5): p. 514). Another potentially important target for Alzheimer's disease is the APOE4 allele of apolipoprotein E (apoE). The APOE4 allele is the greatest genetic risk factor for AD and a person with two APOE4 alleles has 15 times the risk of developing AD than a person with APOE3 alleles. ApoE is thought to bind amyloid beta and the soluble forms of this complex may modulate levels of neurotoxic amyloid beta. Clearance of soluble amyloid beta appears to be slower in the presence of the APOE4 encoded apoE, and apoE may also serve a role in the aggregation and deposition of amyloid beta (Tai et al (2014) *Molecular Neurodegeneration* 9(2)). The interaction sites on the apoE and amyloid beta proteins have been identified studies have shown that blockage of that interaction by use of a peptide Aβ12-28P reduced the behavioral and biochemical hallmarks of AD in a mouse model (Liu et al (2014) *Neurochemistry* 128:577). Thus, the methods and compositions of the invention can be used to treat or prevent AD. Engineered nucleases against Tau or APOE4 can cause a knock out of the endogenous genes and prevent accumulation of the toxic amyloid beta aggregates. In addition, fusion proteins of the invention comprising transcription factor regulatory domains may be used to down regulate expression of either or both Tau and APOE4. Fusion proteins of the invention may also be used to increase the expression beneficial apoE alleles (e.g. APOE2) in a heterozygous subject.

The methods and compositions described herein can also be used to treat and/or prevent Charcot-Marie-Tooth Disease (CMT). CMT is the most common inherited neuro muscular disorder, with a prevalence of approximately 17-40 per 100,000 in the population. The disease is characterized clinically by wasting and weakness in the distal limb muscles, skeletal deformities and a decrease or absence of deep tendon reflexes. The disease can be linked to mutations in a number of different genes, but the various mutations all lead to axonal degeneration where the longer axon fibers are affected first and more severely resulting in the observed impairment of the feet and lower legs (Pareyson et al, (2006) *Neuromolecular Medicine* 8:3). The most frequent subtype of CMT, CMT 1A is usually caused by a 1.5 Mb duplication of chromosome 17p11.2 which leads to an increase in gene dosage or overexpression of the PMP22 gene. PMP22 is an integral membrane protein that is an important component of compact peripheral nervous system myelin sheath. A more severe form of CMT is seen in patients with missense mutations in one copy of PMP22, indicating a toxic gain of function mutation. In mouse models where PMP22 is over-expressed via a regulatable tetracycline operator and causes dysmyelination, reduction of gene expression lead to reversal of the CMT phenotype and myelination of previously unmyelinated nerve fibers (Perea et al (2001) *Human Mol Gen* 10(10):1007). Thus, the methods and compositions of the invention can be used to treat CMT. Specific nucleases of the invention can be designed to knock out or correct specific PMP22 missense mutations, or specific transcription factors of the invention may be designed to reduce expression of PMP22.

Duchenne Muscular Dystrophy (DMD), a disease with nervous system implications, and the most common severe form of muscular dystrophy can also be treated and/or prevented using the methods and compositions described herein. Prevalence of DMD is approximately 1 in 3500 male births and follows an X-linked recessive inheritance pattern. It arises out of mutations in the dystrophin gene, which is the largest gene in the human genome. Dystrophin is a 427 kDa cytoskeletal protein that is required for muscle fiber stability, and loss of the protein results in necrosis and diminished regenerative capacity of muscle, ultimately leading to fibrosis of the muscle tissue. A similar protein, utrophin, is also a cytoskeletal protein that may be able to compensate for defective dystrophin levels. A zinc finger-based transcription factor designed to upregulate utrophin was disclosed in Onori et al (2013, *BMC Molecular Biology* 14(3)) and U.S. Pat. No. 8,304,235. In adult muscle, utrophin localizes to the neuromuscular and myotendinous junctions while dystrophin localizes to the entire sarcolemma. In developing muscle however, utrophin can be found along the sacrolemma. In some DMD patients, utropin levels are upregulated, and there appears to be a positive correlation between the level of utrophin expression and disease progression (Kleopa et al (2006) *Hum Mol Genet* 15(10):1623). Current therapies for patients afflicted with DMD have increased life expectancy by decreasing respiratory complications. However, as patients live longer than in the past, cardiac function complications are becoming more prevalent as a result of cardiomyopathies that occur later in the disease progression (Malik et al (2012) *Expert Opin Emerg Drugs* 17(2):261). Thus, the methods and compositions of the invention can be used to treat, delay and/or prevent the onset of symptoms associated with DMD. Engineered DNA binding proteins (e.g. ZFP, TALEs, CRIPSR/Cas systems) are fused to transcriptional regulator domains to cause an increase in expression of the utrophin and/or dystrophin protein. See, also, U.S. Publication No. 20140140969.

Amyotrophic Lateral Sclerosis (ALS) is the most common adult-onset motor neuron disorder and is fatal for most patients less than three years from when the first symptoms appear. Generally, it appears that the development of ALS in approximately 90-95% of patients is completely random (sporadic ALS, sALS), with only 5-10% of patients displaying any kind of identified genetic risk (familial ALS, fALS). Mutations in several genes, including the C9orf72, SOD1, TARDBP, FUS, ANG, ALS2, SETX, and VAPB genes, cause familial ALS and contribute to the development of sporadic ALS. Mutations in the C9orf72 gene are responsible for 30 to 40 percent of familial ALS in the United States and Europe. The C9orf72 mutations are typically hexanucleotide expansions of GGGGCC in the first intron of the C9orf72 gene. The pathology associated with this expansion (from approximately 30 copies in the wild type human genome to hundreds in fALS patients) appears to be related to the formation of unusual structures in the DNA and to some type of RNA-mediated toxicity (Taylor (2014) *Nature* 507:175). Incomplete RNA transcripts of the expanded GGGGCC form nuclear foci in fALS patient cells and also the RNAs can also undergo repeat-associate non-ATP-dependent translation, resulting in the production of three proteins that are prone to aggregation (Gendron et al (2013) *Acta Neuropathol* 126:829). C9orf72 mutations are also the most common genetic cause of frontotemporal dementia (FTD), a common form of early-onset dementia. Other genetic causes of FTD include mutations in the progranulin gene (GRN) and in the gene encoding Tau (Mahoney et al (2012) *Brain* 135:736). Zinc finger proteins linked to repression domains have been successfully used to preferentially repress the expression of expanded Htt alleles in cells derived from Huntington patients by binding to expanded tracts of CAG. See, also, U.S. Patent Publication Nos. 20110082093 and 20130253040. Thus, the methods and compositions of the invention can be used to treat, delay or prevent ALS and FTD. For example, engineered DNA binding proteins (e.g. ZFPs, TALEs, Cas) can be constructed to bind to the expansion tract of the C9orf72 disease associated allele and repress its expression. Alternatively or in addition, a wild type version of C9orf72, lacking the abnormally expanded GGGGCC tract, may be inserted into the genome to allow for the normal expression of the gene product. Additionally, the fusion proteins of the invention can be used to modulate the expression of other genes (e.g. GRN, Tau) or disrupt them via use of the engineered nucleases of the invention to prevent or treat FTD.

Parkinson's disease (PD) is a neurodegenerative disease that afflicts approximately 4-6 million people worldwide. In the United States, approximately one to two hundred people per 100,000 have PD. It appears that many factors can play a role in disease onset and/or progression of PD. For example, genetic mutations in the leucine rich repeat kinase 2 gene (LRRK2, also known as PARK8) and alpha-synuclein have been identified to be involved in both familial and sporatic forms of PD and have been targeted by nucleases. See, also, U.S. Patent Publication Nos. 20120192301 and 20120214241.

Fragile X syndrome is the leading monogenic cause of intellectual disability and autism. The FMR1 gene (encoding the fragile X mental retardation protein, FMRP) is found on the X chromosome and comprises a CGG trinucleotide repeat track, which in normal FMR1 genes, contains about 5-44 CGG repeats. Subjects with 45-54 repeats are considered to be at risk for Fragile X syndrome, and people with 55-200 repeats are considered to have a pre-mutation for the syndrome. Patients afflicted with Fragile X have between 200 and 1000 CGG repeats. As discussed above, these repeats are also capable of forming the unusual structures in the DNA (G-quadruplexes, see Kettani et al (1995) *J Mol Biol* 254(4):638) As a result, the Fragile X-associated FMR1 gene is methylated and is silenced or improperly expressed. Without sufficient FMRP, mental retardation results. Thus the methods and compositions of the invention can be used to insert a wild type copy of the gene in a safe harbor location to supply the subject with FMRP lacking due to the repeat expansion mutation.

Myotonic dystrophy is another muscle wasting disease associated with neuropathy that affects approximately 1 in 8000 people worldwide. Patients often have prolonged muscle contractions and may not be able to relax specific muscles after use and there may be cardiac conduction defects leading to abnormalities in the electric signals that control heartbeat. There are two types: type 1 and type 2. Type one is apparent at birth (congenital) with muscle impairment generally in the lower legs, hands, neck and face while type 2 has muscle impairment in the neck, shoulders, elbows and hips. DM1 (type 1) and DM2 (type 2) are inherited autosomal dominant diseases caused by unstable expanded sequences (CTG and CCTG, respectively) in the non-coding regions of DMPK and ZNF9 (also known as CNBP), respectively. Radvanszky et al. (2013) *Neuromuscul Disord.* 23(7):591-8. The mutations in both genes result in the intranuclear accumulation of mutant transcripts and misplaced transcripts, resulting in RNA-mediated toxicity. In addition, the presence of neurotangles in the brain of DM patients suggests that DM is also a degenerative brain disease belonging to the class of tauopathies (Calliet-Boudin et al (2013) *Front Mol Neurosci* 6(57)). Thus the methods and compositions of the invention can be used to treat or prevent myotonic dystrophy. Engineered transcription factors can be used to down regulate expression of a diseased allele associated with either DM1 or DM2, or the diseased allele can be knocked out via cleavage by an engineered nuclease. In addition, wild type versions of these genes can be inserted into an endogenous location in the genome to allow for expression of the normal gene product.

Rett syndrome (RTT) is a neurodevelopmental disorder that affects 1 in 10,000 live female births. The symptoms of RTT appear after an early period (approximately 6-18 months of life) of apparently normal development in an infant. Initially there is a slowing down or stagnation of learning skills followed by a loss of communication skills and purposeful use of the hands. RTT can present with a wide range of disability ranging from mild to severe and causes problems in brain function that are associated with cognitive, sensory, emotional, motor and autonomic functions leading to effects on speech, sensation, mood, movement, breathing, cardiac function, and digestion. Life expectancy is thought to be 40 to 50 years, with patients requiring intensive care for daily life. RTT is usually caused by a mutation in the Methyl CpG binding protein 2 (MECP2) where 35% of RTT cases are cause by nonsense mutations in MECP2 (see Pitcher et al, (2015) *Hum Mol Genet* 1-11, doi: 10.1093/hmg/ddv030). In fact, 60% of RTT cases are caused by 8 different mutations in the MECP2 protein as follows: R106W; R133C; T158M; R168X; R255X; R270X; R294X and R306C. Thus, the methods and compositions of the invention can be used to treat RTT. Engineered transcription factors can be designed to shut off the expression of mutant MECP2 genes and/or to upregulate a wild type MECP2 gene in a heterozygous individual. Engineered nucleases can be used to introduce a double strand break in the 5' end of the mutant MECP2 gene followed by targeted integration of a cDNA comprising a sequence encoding the MECP2 gene and a poly A signaling sequence. The MECP2 promoter will thus drive normal expression of the inserted transgene while silencing the mutant copy. Viral vectors comprising either the engineered transcription factor or engineered nuclease can be introduced into the brain to edit the cells therein. Similarly, these viral vectors can be introduced into other target tissue such as the heart and/or lung tissue to cause the expression of the wild type protein in these tissues. Additionally, altered regulation (e.g. up regulation of gene expression) of other factors which interact with MECP2 are also contemplated, including brain derived neutrotrophic factor (BDNF) and insulin like growth factor (IGF), both of which have been found to partially reverse some of the phenotypes associated with RTT in rodent models (Pitcher ibid).

Canavan's disease (CD) is a hereditary leukodystrophy caused by mutations in the aspartoacylase gene (ASPA) that lead to a loss of enzyme activity and an increase in concentrations of the enzyme's substrate N-acetylaspartate (NAA) in the brain. There are over 54 characterized loss of function mutations in ASPA that lead to CD, and the disease is characterized by dysmyelination, intramyelinic edema, and extensive vacuolization of the CNS white matter (see Ahmed and Gao (2013) *Mol Ther* 21(3): 505-506). Clinically, CD leads to macrocephaly, severe cognitive and motor delays, epilepsy and death, typically after about thirty years of life. Symptoms appear in the first 3 to 6 months of life and progress rapidly. Gene therapy has been attempted for this disease were AAV comprising the ASPA gene was introduced into the brain with some success (see Leone et al (2012) *Sci Transl Med* 4(165): 165ra163. Doi:10.1126/scitranslmed.3003454). Additionally, stem cell therapy where corrected neuronal stem cells derived from patent iPSC has also been proposed (see Goldman et al, (2008) *Hum Mol Genet* 17(1) R76-R83). Thus, the methods and compositions of the invention can be used to prevent or treat Canavan's disease. Since the accumulation of the ASPA precursor NAA is tied to many of the symptoms of the disease, an engineered transcription factor can be used to increase the expression of a wild type ASPA allele in situ in the brain. Similarly, engineered nucleases can be used to knock out expression of an aberrant ASPA allele, or can be used to introduce a short oligonucleotide to correct a mutated gene and/or to introduce a wild type cDNA. Additionally, wild type ASPA protein may be made hepatically (e.g. from the albumin locus) where the protein comprises a peptide allowing it to cross the blood brain barrier. Thus the methods and compositions of the invention can be utilized to cause a decrease in the accumulation of NAA and thus decrease the symptoms of the disease. In addition, the invention contemplates the correction of an aberrant ASPA gene in an iPSC derived from a Canavan patient that can be forced along the pathway to becoming a neuronal stem cell. These altered neuronal stem cells are then reintroduced into the brain of the patient and correct and/or treat the disease.

Dravet syndrome (DS, also known as Severe Myoclonic Epilepsy of Infancy) is a genetic epilepsy syndrome associated with loss of function mutations in SCN1A, the gene that encodes the alpha 1 subunit of the voltage dependent sodium channels (SCN1A mutations are found in 79% of diagnosed DS patients). The alpha subunits form the transmembrane pore in the channel. Typically, the SCN1A mutations cluster in the C-terminus of the protein and cause a loss of function, resulting in decreased activity in GABAergic inhibitory neurons (see Rossi (2014) *Epil Curr* 14(4):189-190). Additionally the activity of the Nav1.6 sodium channels is reduced in DS. Unfortunately, DS is refractory to most current anti-epileptic medications. Symptoms appear in the first year of life as prolonged seizure events. At two years of age, patients begin suffering from a variety of other seizure types and developmental milestones begin to plateau and then regress during this phase. Eventually the symptoms include motor and balance issues, delayed language and speech, growth and nutrition issues, sleeping difficulties, and chronic infections. In addition to SCN1A, the SCN8A gene may also be involved in DS, as it has been found that increased seizure resistance is found in mice with mutations in the mouse Scn8A gene. Thus, SCN8A may be a genetic modifier of DS (see Martin et al (2007) *Hum Mol Gene* 16(23):2892-2899). Hence, the methods and compositions of the invention can be used to prevent or treat DS. Engineered transcription factors can be used to down regulate expression of SCN8A in the brain to decrease seizure frequency. Engineered nucleases could be designed to cleave the mutant SCN1A alleles to knock out expression. Alternatively or in addition, a wild type cDNA encoding the SCN1A gene could be introduced into the brain using various methods known in the art (e.g. through a viral vector such as AAV2) in addition to mutant SNC1A specific nucleases to cause expression of the wild type gene in place of the mutant. Stem cells corrected by the methods of the invention can also be introduced into specific seizure centers to treat or prevent Canavan disease.

Another genetic disease of the nervous system is Spinal Muscular Atrophy (SMA). SMA is the most frequent genetic cause of death in infants and toddlers (approximately 1 in 6-10,000 births) and involves progressive and symmetric muscle weakness involving the upper arm and leg muscles as well as the muscles of the head and trunk and intercostal muscles. Additionally there is degeneration of the motor neurons in the spinal cord. SMA onset has been divided into three categories as follows: Type I, the most common, has an onset at about 6 months of age and results in death by about 2 years; Type II has an onset between 6 and 18 months where the patient can have the ability to sit up, but not walk; and type III, which has an onset after 18 months, where the patients have some ability to walk for some amount of time. 95% of all types of SMA are tied to a homozygous loss of the survival motor neuron 1 (SMN1) protein. The severity of SMA can be offset by the expression of the SMN2 protein, which is nearly identical to SMN1 except for a single mutation that plays a role in the splicing of the RNA message. SMN2 is truncated however and rapidly degraded so while high expression of SMN2 may partially alleviate the loss of SMN1, it is not fully able to compensate (see Iascone et al (2015) *F1000 Pri Rep* 7:04). In fact, there appears to be an inverse correlation with the amount of SMN2 mRNA and the severity of the SMA disease. Since SMA is associated with a homozygous loss of the SMN1 gene, some researchers have tried introducing the SMN1 gene via an AAV9 viral vector in animal models of SMA (see Bevan et al (2011) *Mol Ther* 19(11):1971-1980). This early work showed that the gene could be delivered either through IV administration or through direct injection into the cerebral spinal fluid. However, penetration of the virus and complications relating to the crossing of the blood brain barrier still exist. The methods and compositions of the invention can be used to prevent or treat SMA. Engineered transcription factors specific for SNM2 may be designed to increase the expression of this gene. Engineered nucleases can also be used to cleave and correct the SMN2 mutation and cause stable expression by essentially turning it into the SMN1 gene. Furthermore, a wild type SMN1 cDNA may be inserted into the genome by targeted insertion using an engineered nuclease. The wild type SMN1 gene may be inserted into the endogenous SMN1 gene and thus be expressed under the regulation of the SMN1 promoter, or it may be inserted into a safe harbor gene (e.g. AAVS1). The gene may also be inserted via nuclease directed targeted integration into neuronal stem cells, where the engineered stem cells are then re-introduced into the patient such that the neurons that are derived from these stem cells function normally.

Crigler Najjir syndrome is a disease related to hyperbilirubinemia caused by an excess of unconjugated bilirubin in the blood which leads to severe neurological damage. The disease is tied to deficiency in the uridine-diphosphate (UDP) glucuronosyltransferase 1A1 enzyme encoded by the UGT1A1 gene. Mutations in the UGT1A1 gene that result in no expression cause the disease, and current treatment is limited to phototherapy treatment for 10-12 hours per day. The lack of UDP1A1 leads to high concentrations of unconjugated bilirubin in the blood. Normally the enzyme acts on bilirubin to make it more water soluble and thus allows the molecule to be more easily eliminated from the body. Mutations in the promoter region of UGT1A1 may also be tied to a closely related, but milder disease known as Gilbert syndrome. UGT1A1 is most highly expressed in the liver. In rat models of Crigler Najjir disease (the so-called Gunn rat) adenoviral or lentiviral vectors have been able to deliver the UCT1A1 gene to the liver and normalize plasma bilirubin levels (see van der Wegen (2005) *Mol Ther* 13(2) p. 374). Additional studies using delivery by AAV have also shown promise (see Bortolussi et al (2014) *Hum Gen Ther* 25:844-855). The methods and compositions of the invention provide a treatment for both Crigler Najjir and Gilbert syndromes. Engineered nucleases can be used to insert the UGT1A1 gene into the albumin promoter in the liver and cause expression of the enzyme such that serum bilirubin levels are dropped. Alternatively, the gene can be inserted into other safe harbor loci in the liver (e.g. AAVS1).

Opiate addiction is undergoing a resurgence and has emerged as an epidemic, especially in parts of the United States. It is estimated that between 26 and 36 million people worldwide participate in opiate abuse, with an estimated 2.1 million people in the United States suffering from substance use disorders related to prescription opioid pain relievers in 2012, and an estimated 467,000 people in the US are addicted to heroin (see United Nations Office on Drugs and Crime, World Report 2012 and Substance Abuse and Mental Health Services Administration, NSDUG Series H-46, HHS Publication No (SMA) 13-4795). In the brain, the primary site of action of nearly all analgesic and addictive opiates is the mu opioid receptor (MOP-r, encoded by the OPRM1 gene). The endogenous ligands for this receptor are the peptide products of the precursor proteins proopiomelanocortin (POMC) and proenkephalin (PENK). The endogenous opioid system also includes two other receptors, delta (DOP-r, encoded by OPRD1) and kappa (KOP-r, encoded by OPRK1). It has been reported that mutations in the endogenous opiate system may play a role in the susceptibility of an individual to opiate addiction, and the success of treatment from addiction (see Reed et al (2014) *Curr Psychiatry Rep* 16:504). For example, the A118G SNP in OPRM1 results in the Asn40Asp amino acid substitution in MOP-r and is associated with a substantial reduction of OPRM1 mRNA expression, and thus reduced levels of MOP-r. The MOP-r that is produced also has an increased binding affinity for its natural ligand. Importantly, the A118G SNP results in an altered response in the stress and hypothalamic-pituitary-adrenal axis in humans. This alone is thought to be a major factor in the vulnerability to specific addictions. In fact, the A118G SNP is associated with a substantial increase in the vulnerability to heroin addiction (Reed, ibid). Polymorphisms in other genes associated with the endogenous opiate system such as OPRK1 and OPRD1 may also prove to be factors leading to susceptibility to opiate addiction. Additionally, transcription factors that are elevated in response to stimulation of MOP-r such as ELK1 (tied to many cellular processes such as cell division, differentiation, migration and apoptosis) are elevated to a greater extent in people with the A118G SNP than in controls (Sillivan et al (2013) *Biol Pyschiatry* 74(7): 5110519).

The mu opiate receptor (MOP-r) has also been tied to other disorders of the brain. For example, borderline personality disorder (BPD, shown to be present by epidemiological data in 1-5% of the population) may be tied to a dysregulation of the endogenous opiate system. Patients with BPD suffer from a dysregulation of emotional processing and MOP-r is implicated in emotional and stress response regulation (see Prossin et al (2010) *Am J Psychiatry* 167:925-933). Studies have demonstrated that BPD patients at baseline have an increase in MOP-r availability then controls, although the OPRM1 genotype was not investigated. This increased MOP-r availability is thought to cause a greater activation of stress and emotional responses leading to the dysregulation observed in BPD patients. BPD patients have a marked increase in morbidity and mortality that includes risk for suicide and over the long term, they have severe and persistent impairment in social functioning. BPD patients also display an increased susceptibility to opiate addiction as nearly 40% have a co-diagnosis of drug use disorder (see Panagopoulos et al (2013) *Drug Alcohol Depend* 128(3)). Both opiate addiction and BPD represent chronic states that have enormous impact on patients over a lifetime. Thus the methods and compositions of the invention can be used to prevent or treat dysfunction in the endogenous opiate system that are associated with opiate addiction and/or BPD. Engineered transcription factors comprising DNA binding domains specific for OPRM1 may be used to repress the expression of dysfunctional receptors in opiate addicts and BPD patients. Similarly, engineered nucleases may be used to knock out or correct specific genes encoding mutant receptors such as the A118G OPRM1 variant. Nucleic acids encoding these engineered proteins may be delivered to the brain via viral delivery systems. In addition, wild type genes encoding MOP-r may be delivered to specific areas of the brain known to be highly active in the pathology of addiction and/or BPD and inserted into the genome via nuclease targeted integration to treat or prevent these disorders. Similarly, stem cells corrected by the methods of the invention can be introduced into the brain that are associated with addiction and/or BPD to treat or prevent these conditions.

Major depressive disorder (MDD) is another common psychiatric illness with high levels of morbidity and mortality. Approximately 10 to 15 percent of the population will experience clinical depression during their lifetime, and twin studies suggest that MDD has a heritability of 40 to 50%. Due to the response of MDD patients to medications related to serotonin, several investigators have examined the serotonin system in MDD. Some studies have implicated variants in the serotonin transporter (5HTT/SLC6A4) and serotonin receptor 2A (HTR2A) as potential targets for the treatment of MDD. For example, a 44 by repeat polymorphism in the promoter region of SLC6A4 may be implicated in MDD (Lohoff (2010) *Curr Psychiatry Rep* 12(6):539-546). BDNF (brain derived neurotrophic factor) is another gene that has been suggested to have a tie to MDD. For example, the Val66Met mutation in the BDNF protein may be implicated in MDD. Other genes, associated with the synthesis of serotonin in the brain such as tryptophan hydroxylase (encoded by TPH2) may be targeted for the treatment of MDD. The Arg441His variant in TPH2 results in an 80% reduction of serotonin production in vitro, and so may play a similar role in MDD in vivo (Lohoff, ibid). Thus, the methods and compositions of the invention may be used to prevent or treat MDD in a patient. Mutant alleles in SLC6A4, HTR2A and/or TPH2 may be targeted by the engineered transcription factors or nucleases of the invention to repress or knock out expression. Wild type genes for these loci may also be introduced via nuclease-dependent targeted integration. Similarly, stem cells corrected by the methods of the invention can be introduced into the brain. Corrective measures (i.e. engineered transcription factors, nucleases, donor DNAs, stem cells) can be targeted in areas of the brain that are associated with MDD.

Schizophrenia (SZ) does not appear to be linked to a single gene, yet while it occurs in 1% of the general population, a family history of psychosis increases the risk to about 10% of people with a parent or sibling with SZ. Twin studies have also shown that an identical twin has about a 50% chance of having SZ if their twin has it. Overall, 80% of SZ patients appear to have a genetic component to their disease. Early studies showed evidence of SNPs in the DTNBP1 (dystrobrevin-binding protein 1 or dysbindin) were strongly associated with SZ (Straub et al (2002) *Am J Hum Genet* 71:337-348). More recently, genome-wise association studies have found 108 independent associated loci that are associated with SZ, and of these 108, 75% were located in protein coding genes (see Ripke et al (2014) *Nature* 511(7510): 421-427). Notably, associations were found with the DRD2 gene (currently the target of all effective anti-psychotic drugs), and genes involved in glutamatergic neutrotransmission and synaptic plasticity (e.g. GRM3, GRIN2A, SRR, GRIA1). Associations were also seen with voltage gated calcium channel subunits (e.g. CACNA1C, CACNB2, CACN11I). SZ also may be associated with epigenetic regulation. An observed down regulation of glutamic acid decarboxylase67 (GAD1), reelin (RELN) and BDNF expression in the brain of patients suffering from SZ is associated with overexpression of DNA methyltransferase 1 (DNMT1) and ten-eleven translocase methylcytosine dioxygenase 1 (TET1). DNMT1 and TET1 encode enzymes that methylate and hydroxymethylate cytosines near and within cytosine phosphodiester guanine (CpG) islands of many gene promoters. Other evidence suggests that expression of GAD1 is epigenetically regulated in specific regions of the brain by epigenetic mechanisms (see Mitchell (2014) *Schizophr Res* doi:10.1016/j.schres 2014). Thus, the methods and compositions of the invention can be used to prevent or treat SZ. Specific nucleases of the invention may be designed to target disease associated SNPs such as in DTNBP1 to knock out disease associated alleles. Further, specific transcription factors and/or nucleases can be engineered to modulate specific alleles of DRD2, GRM3, GRIN2A, SRR, GRIA1, CACNA1C, CACNB2, CACN11I, GAD1, RELN, BDNF, TET1, and DTNBP1. Nucleic acids encoding these modulators can be injected into the brain in the regions of the brain known to be most affected by SZ, or they can be delivered via viral vectors. Similarly, stem cells corrected by the methods of the invention can be introduced into the brain and used to treat or prevent SZ.

Bipolar disorder (BD) is another extremely debilitating psychiatric disorder affecting about 1% of the population worldwide, and is associated with increased morbidity and mortality that appears to have a strong genetic component. Among mental disorders, BD is associated with the highest risk of suicide and is characterized by cyclothymic and irritable temperaments, leading to a rate of suicide that is up to 20 times that of the average population (see Dwivedi and Zhang (2015) *Front Neurosci* 8(457)). Genome wide association studies have been performed and have identified a number of SNPs in specific chromosomal regions in the genome. These include ANK3, ODZ4, TRANK1, ADCY2, CACNA1C and a region of the genome between MIR2113 and POU3F2 (see Muhleisen et al (2014) *Nat Com* 5, article number 3339; and Ferreira et al (2008) *Nat Genet* 40(9): 1056-1058). Epigenetic regulation of BDNF expression also seems to play a role in BD. BD patients often respond favorably to therapeutic lithium treatment, and it appears that one of the mechanisms of lithium is to cause hypomethylation of the BDNF exon IV promoter resulting in increased BDNF expression. Thus, the methods and compositions of the invention can be used to prevent or treat BD. Specific nucleases of the invention may be designed to target disease associated SNPs such as in ANK3, ODZ4, TRANK1, ADCY2, and CACNA1C to knock out disease associated alleles. Further, specific transcription factors can be engineered to modulate and increase the expression of BDNF. Nucleic acids encoding these modulators or stem cells corrected by the methods of the invention can be introduced into the brain in the regions of the brain known to be most affected by BD, or they can be delivered via viral vectors.

Migraine is the most common disorder in the NS, affecting approximately 14% of the adult population. Genome wide association studies pooling data from several studies (considering over 23,000 individual migraine suffers) have identified 12 loci that have an association with migraine. These include SNP rs2651899 in PRDM16, rs10915437 near AJAP1, rs12134493 in MEF2D, rs7577262 in TRPM8, rs6790925 near TGFBR2, rs9349379 in PHACTR1, rs13208321 in FHM5, rs4379368 in c7orf10, rs10504861 near MMP16, rs64782541 in ASTN2, rs12134493 near TSPAN2, rs701567 near GFRA2 and rs11172113 in LRP1 (See Anittila et al (2013) *Nat Genet* 45(8):912-917). Interestingly, eight of the 12 identified loci are located in or immediately outside genes with known function in synaptic or neuronal regulation and several exert regulatory control on one another, suggesting a common circuitry. Thus, the methods and compositions of the invention may be used to prevent or treat chronic migraine in patients. Engineered transcription factors and nucleases may be designed to repress or knockout mutant genes known to induced recurrent migraine. In addition or alternatively, wild type genes may be inserted in to safe harbor loci of cells in the brain via nuclease dependent targeted integration to cause expression of wild type proteins. Similarly, stem cells corrected by the methods of the invention can be introduced into the brain in the areas know to be associated with migraine to treat or prevent the disease.

Genetic factors contributing to multiple sclerosis (MS) are not well characterized although there is strong evidence that a genetic link exists. MS is a chronic inflammatory autoimmune disease believed to arise from a complex interaction of both environmental and genetic factors and manifests in different forms and severity. The genes encoding the major histocompatibility complex (MHC) are associated with susceptibility to MS, in particular the HLA-DRB1allele HLA-DRB1*1501 (SNP rs3135388, Lincoln et al (2005) *Nat Genet* 37(10):1108-12) as are the genes IL7Ra and IL2Ra (Tan et al (2014) *Ann Transl Med* 2(12):124). Other genome wide association studies have found two mutant alleles in two additional genes that may be candidates for the methods and compositions of the invention. In the gene CYP27Ba, which encodes the vitamin-D activating 1-alpha hydroxylase enzyme, a loss of function variant has been identified (R389H) which seems to be associated with susceptibility to MS. Another SMP (rs55762744) found in TYK2, also may be associated with a high frequency of developing MS. TYK2 encodes a tyrosine kinase that modulates the function of multiple immune related genes, and mutations in this gene may lead to MS (see Jiang et al (2014) *Ann Transl Med* 2(12):125). Thus, the methods and compositions of the invention may be used to prevent or treat MS. Engineered transcription factors and/or nucleases can be used to repress or knockout mutant alleles associated with MS such as HLA-DRB1*1501. Additionally, wild type genes can be inserted into the genome via nuclease assisted targeted integration in safe harbor genes where the genes and nucleases are delivered to the brain in the regions most associated with MS phenotype. Stem cells corrected by the methods of the invention can also be used. Delivery can be via direct introduction of cells, or via viral vectors.

Tourette syndrome (TS) is a neuropsychiatric disorder characterized by repetitive, involuntary movements and vocalizations called tics and is often accompanied by obsessive-compulsive disorder and/or attention-deficit/hyperactivity disorder. Worldwide prevalence of TS is estimated to be between 0.3 and 1% of the population and the heritability behind TS appears to be complex. Several researchers have identified multiple rare copy number variants (CNVs) including genomic deletions and duplications that may play a role in TS. Several exon-affecting rare CNVs were found in one study and three had previously been implicated in studies related to schizophrenia, autism and attention-deficit hyperactivity disorder. The five loci were in the NRXN1, AADAC, CTNNA3, FSCB and KCHE1, KCHE2, RCAN1 genes. A deletion of the 5' exon of the neurexin 1 gene (NRXN1) is associated with TS (also with autism, schizophrenia) as is deletion of the 5' region of microsomal arylacetamide deacetylase (AADAC). Deletion of 450 Kb of the FSCB gene (encoding fibrous sheath CABYR-binding protein) was also associated with TS as was a duplication of genes involved with voltage-gated potassium channels (KCNE1, KCNE2) and a regulator of calcineutin 1 (RCAN1). Some of these genes encode cell adhesion molecules (e.g. NRXN1) which may play a role in linking synaptic cell adhesion to cognition (Sundaram et al (2010) *Neurology* 74(20):1583). Thus, the methods and compositions of the invention can be used to prevent or treat TS. Engineered transcription factors and/or nucleases can be used to repress or knockout mutant alleles associated with TS such as those in NRXN1, AADAC, CTNNA3, FSCB and KCHE1, KCHE2, RCAN1. Additionally, wild type genes can be inserted into the genome via nuclease assisted targeted integration in safe harbor genes or corrected stem cell, where the genes, nucleases and/or stem cells are delivered to the brain in the regions most associated with TS phenotype. Delivery can be via direct introduction or via viral vectors.

Epilepsy affects about three percent of the population and comprises a wide constellation of primary and syndromic neurological disorders. The epileptic encephalopathies (EE) are the most severe of the epilepsies, distinguished by multiple refractory seizures, cognitive deficit, and poor developmental outcome. De novo mutations in several genes are known causes of EE, but the genetic etiology of the vast majority of these encephalopathies is unknown. People with epilepsy tend to suffer from recurrent seizures due to excessive neuronal discharge. It appears that genetic factors play a role in 40% of epilepsies, however it has been difficult to identify the specific genes involved. In a study of Han Chinese subjects, two highly correlated SNPs, rs2292096 and rs6660197 located in the CAMSAP1LK1 gene showed a relationship with epilepsy. CAMSAP1L1 encodes a cytoskeletal protein (Tan et al, 2014, ibid). Some approaches to epilepsy embrace the idea of using gene therapy to treat the symptoms of the disease such as anti-seizure approaches (e.g. to decrease the effect of excitatory neurotransmitters such as antisense approaches against NMDA receptor subunit 1, or increase the inhibition of neurotransmission such as GAMA-A receptor subunit alpha-1, GAD65 or adenosine kinase) or disease modifying approaches. For example, overexpression of an endogenous molecule with anticonvulsant properties at the area in the brain associated with seizure onset could modify the frequency and intensity of seizures. Enhanced release of neurotrophic factors such as GDNF, BDNF, and FGF also could be helpful. Neuropeptides and as galanin and neuropeptide Y (NPY) could be promising candidates for such a purpose (see Noe et al., 2012. Noebels et al, editors. Jaspar's Basic Mechanisms of the Epilepsies. 4th Edition. Bethesda (Md.): National Center for Biotechnology Information). Thus the methods and compositions of the invention can be used to prevent or treat epilepsy. Approaches that are helpful to decrease excitatory neurotransmitters can be carried out where the engineered transcription factors and/or nucleases of the invention are used to repress or knock out NMDA receptor subunit 1, GAMA-A receptor subunit alpha-1, GAD65 or adenosine kinase. Other uses of these methods and compositions can be to repress or knock out specific mutant alleles associated with SNPs in the CAMSAP1LK1 gene. In addition, genes encoding transcription factors to increase the expression of GCNF, BDNF and IGF may be administered in a localized fashion at the seizure centers within the brain. Similarly, cDNAs encoding anti-convulsant peptides such as NPY and galanin can be inserted via nuclease driven targeted integration in to seizure centers to inhibit the frequency and magnitude of seizures.

Thus, alterations to genes encoding proteins involved in NS disorders using the methods and compositions as described herein can be used to correct an aberrant endogenous gene or insert a wild type gene at a desired location in the genome of a cell (e.g., into a "safe harbor" gene of an HSC). Precursor cells can be derived from subjects in need, modified ex vivo, and then given back to the subject either in a bone marrow graft. Alternatively, polynucleotides encoding the fusion proteins of the invention can be delivered to the neural tissue for correction, modification of expression, gene silencing and/or targeted insertion of a gene for the treatment or prevention of a nervous system disorder. Non-limiting examples of sequences suitable for targeting are shown in Table 1.

Disclosed herein are compositions and methods useful for modulation of expression and targeted cleavage and alteration of genes in plants, particularly paralogous genes in plants. Regulation of a paralogous gene can be modulated, e.g., by using engineered transcription factors or modifying gene regulatory regions. Genes can be altered, e.g., by targeted cleavage followed by intrachromosomal homologous recombination or by targeted cleavage followed by homologous recombination between an exogenous polynucleotide (comprising one or more regions of homology with the gene nucleotide sequence) and a genomic sequence. A non-limiting example of a paralogous gene in plants is the EPSPS gene. Thus, the methods and compositions of the invention may be used to disrupt an EPSPS gene with a CRISPR/Cas system where the single guide RNA comprises sequences to target a plant EPSPS gene.

The present disclosure provides methods and compositions for expressing one or more products of an exogenous nucleic acid sequence (i.e. a protein or a RNA molecule) that has been integrated into a Zp15 gene in a plant cell. As shown in the co-owned U.S. Pat. No. 8,329,986, the integration of one or more exogenous sequences at or near the Zp15 locus does not appear to impair the ability of the host plant to regenerate, flower or produce seed and, optionally, allows heritable transmission of the exogenous sequence(s) over generations. The exogenous nucleic acid sequences can comprise, for example, one or more genes or cDNA molecules, or any type of coding or noncoding sequence, as well as one or more control elements (e.g., promoters). For instance, herbicide tolerance genes can be integrated into this locus to produce crop plants with the desired herbicide resistance. Cells containing exogenous nucleic acids at or near the Zp15 locus can also contribute to the gametophyte (germline) and therefore be transmitted to progeny in subsequent generations. Thus, the methods and compositions of the invention may be used to disrupt a Zp15 gene with a CRISPR/Cas system where the single guide RNA comprises sequences to target a plant ZP15 gene.

The present disclosure provides compositions and methods for modulating expression and for targeted alteration in whole plants or plant cells of one or more plant genes involved in fatty acid biosynthesis, thereby altering the fatty acid composition in the whole plant or plant cells. Whole plants or plant cells can be from monocotyledonous (monocots) or dicotyledonous (dicots) plant species, including in some particular embodiments oil-producing plants, and also include cultured cells, cells in a plant at any stage of development, and plant cells that have been removed from a whole plant and which cells (or their descendants) will be regenerated into plants. Plant cells can contain one or more homologous or paralogous gene sequences, any number of which or all of which can be targeted for modification by the methods disclosed herein.

In one aspect, described herein is a DNA-binding domain (e.g., Cas protein) that specifically binds to a gene involved in a plant fatty acid biosynthesis pathway. In some embodiments, the gene is a *Brassica napus* gene. In some particular embodiments, the *Brassica napus* gene can encode Acetyl-COA carboxylase (ACCase), β-ketoacyl-ACP synthetases (KAS, e.g., KASI-KAS IV), Fatty acid thioesterase B (FATB, e.g., FATB1-FATB5, or other plastidial thioesterases), Fatty acid synthase (FAS), Fatty acid elongase (FAE, e.g., FAE1), Fatty acid thioesterase A (FatA), Fatty acid desaturase (Fad2, Fad3), plastidial G-3-P dehydrogenase (GPDH), glycerokinase (GK), stearoyl-acyl carrier protein desaturase (S-ACP-DES), and oleoyl-ACP hydrolase. In some particular embodiments, the gene can be an ortholog or a homolog of these genes in other oil-producing plant species. Thus, the methods and compositions of the invention may be used to disrupt a gene involved with fatty acid biosynthesis with a CRISPR/Cas system where the single guide RNA comprises sequences to target a fatty acid synthesis gene.

Malate dehydrogenase (MDH) catalyzes a reversible NAD+-dependent-dehydrogenase reaction involved in central metabolism and redox homeostasis between organelle compartments in both plants and mammals. Plant tissues contain multiple isoforms of malate dehydrogenase (1-malate-NAD-oxidoreductase [MDH]; EC 1.1.1.37) that catalyze the interconversion of malate and oxaloacetate (OAA) coupled to reduction or oxidation of the NAD pool. Notably, OAA is readily transported both into and out of isolated plant mitochondria, in contrast to mammalian mitochondria, which are essentially impermeable to this organic acid. MDH-mutant plants exhibit either no obvious phenotype or slower growth rates and altered photorespiratory characteristics. See, e.g., Tomaz et al. (2010) *Plant Physiol.* 154(3):1143-1157, Goodman, M. M., Newton K. J. and Stuber, C. W. (1981) *Proc. Nat. Acad. Sci. USA* 78:1783-1785 or Imsande, J. et al. (2001) *J. Heredity* 92:333-338 and U.S. Patent Publication No. 20090123626 describes the use of MDH antisense to reduce asparagine levels, which in turn lowers the level of acrylamide that accumulates upon processing-associated heating of the plant and plant products. Thus, the methods and compositions of the invention may be used to disrupt a malate dehydrogenase (MDH) with a CRISPR/Cas system where the single guide RNA comprises sequences to target a MDH gene.

The CRISPR/Cas system comprises an engineered sgRNA (or its equivalent) to target desired locations in a genome. Only 12 base pairs of this guide RNA and 2 base pairs of the PAM sequence (14 base pairs total) appear to be critical for CRISPR/Cas activity in the *S. pyogenes* Cas. Assuming the CRISPR/Cas construct is absolutely specific for these 14 base pairs, we would expect such a construct to cleave approximately 20 times in the human genome since a given 14 nucleotide sequence will occur approximately once every 268,435,456 ($4^{14}$) nucleotides, the haploid human genome contains approximately 3,000,000,000 nucleotides, and the 14 nucleotide sequence can be on either of the two strands of the genome. This figure also requires absolute specificity of recognition. So the actual number of off target cleavage sites could be higher. The instant invention provides methods and compositions to increase the target size of the CRISPR/Cas system to increase its specificity. The Cas nuclease comprises two nuclease domains, the HNH and RuvC-like, for cleaving the sense and the antisense strands of the target DNA, respectively. The Cas nuclease can thus be engineered such that only one of the nuclease domains is functional, thus creating a Cas nickase (see Jinek et al, ibid). Nickases can be generated by specific mutation of amino acids in the catalytic domain of the enzyme, or by truncation of part or all of the domain such that it is no longer functional. Since Cas comprises two nuclease domains, this approach may be taken on either domain. A double strand break can be achieved in the target DNA by the use of two such Cas nickases. The nickases will each cleave one strand of the DNA and the use of two will create a double strand break. Thus, specificity of the system is increased greatly by using two Cas nickase proteins because the target length is increased from 12-14 nucleotides to 24-28 nucleotides (not including the spacer in between the two subtargets). Using this approach, the expected number of perfectly matched off-target sites in a human genome drops by a factor or $4^{14}$, from ~20 (as described above) to ~<$10^{-7}$ (assuming a 28 base pair DNA recognized by the CRISPR/Cas nickase dimer).

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid or between two nucleic acids). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

The terms "chimeric RNA", "chimeric guide RNA", "guide RNA", "single guide RNA" and "synthetic guide RNA" are used interchangeably and refer to the polynucleotide sequence comprising the guide sequence, the tracr sequence and the tracr mate sequence. The term "guide sequence" refers to the about 10-30 (10, 11, 12, 13, 14, 15, 16, 17, 18, 19, 20, 21, 22, 23, 24, 25, 26, 27, 28, 29, 30) base pair sequence within the guide RNA that specifies the target site and may be used interchangeably with the terms "guide" or "spacer". The term "tracr mate sequence" may also be used interchangeably with the term "direct repeat(s)".

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,586,526 6,140,081; 6,453,242; and 6,534,261; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 8,586,526; 5,789, 538; 5,925,523; 6,007,988; 6,013,453; 6,200,759; as well as WO 95/19431; WO 96/06166; WO 98/53057; WO 98/54311; WO 00/27878; WO 01/60970 WO 01/88197; WO 02/099084.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases (e.g., CRISPR/Cas) as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional CRISPR/Cas nucleases and/or additional pairs of zinc-finger or TALEN proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 2007/0218528, 2008/0131962 and 2011/0201055, incorporated herein by reference in their entireties.

By "orthogonal" or "orthogonal dimers" is meant a dimer that does not dimerize with a second dimer. For example, the components of a first dimer of species a and species b (dimer "ab") do not dimerize with the components of a second dimer comprising species c and species d (e.g., dimers of "ac" and "ad", or "bc" and "bd" are not formed). Non-limiting examples of such orthogonal dimers are found in U.S. Pat. No. 8,623,618 and U.S Publication Nos. 20110201055 and 20140120612, including nuclease fusion proteins that can form dimers using the FokI mutants ELD/KKR and DAD/RVR or RDD/DRR, but cannot form ELD/RVR, ELD/DAD, KKR/DAD, KKR/RVR, ELD/DRR, RDD/KKR, ELD/RDD or KKR/DRR dimers.

A "nuclease defective" or "catalytically inactive" Cas9 protein is a protein (for example in dimer) that exhibits reduced or eliminated nuclease (cleavage activity) as compared to wild-type, for example via one or more mutations (e.g., substitutions, deletions, insertions and/or truncations). DNA-binding capability of a nuclease defective Cas9 protein is typically not affected.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. Suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is known to those with skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the probe sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylates, demethylases, acetylases, deacetylases, kinases, phosphatases, integrases, recombinases, ligases, topoisomerases, gyrases and helicases. Thus, the term includes "transgenes" or "genes of interest" which are exogenous sequences introduced into a cell.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™), Agrobacterium-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid. A "fusion polypeptide" is a polypeptide comprising a polypeptide or portion (e.g., one or more domains) thereof fused or bonded to heterologous polypeptide. Examples of fusion polypeptides include immunoadhesins which combine a portion of the Cas protein with an immunoglobulin sequence, and epitope tagged polypeptides, which may comprise a Cas protein, for example, or portion thereof fused to a "tag polypeptide". The tag polypeptide has enough residues to provide an epitope against which an antibody can be made, yet is short enough such that it does not interfere with nuclease activity of Cas. Suitable tag polypeptides generally have at least six amino acid residues and usually between about 6-60 amino acid residues.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. An "engineered gene" refers to a gene which has been altered in some manner such that it is non-identical with a wild type gene. Alterations can be in the form of targeted deletions, insertions and truncations. An engineered gene can comprise coding sequences from two heterologous genes or may comprise synthetic gene sequences. An engineered gene may also comprise changes in the coding sequence that are silent in the protein sequence (e.g. codon optimization). An engineered gene can also comprise a gene with altered regulatory sequences.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a CRISPR/Cas system as described herein. Thus, gene inactivation may be partial or complete.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soy, canola (rapeseed), and alfalfa. Plant cells may be from any part of the plant and/or from any stage of plant development.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

"Red Blood Cells" (RBCs), or erythrocytes, are terminally differentiated cells derived from hematopoietic stem cells. They lack a nuclease and most cellular organelles. RBCs contain hemoglobin to carry oxygen from the lungs to the peripheral tissues. In fact, 33% of an individual RBC is hemoglobin. They also carry $CO_2$ produced by cells during metabolism out of the tissues and back to the lungs for release during exhale. RBCs are produced in the bone marrow in response to blood hypoxia which is mediated by release of erythropoietin (EPO) by the kidney. EPO causes an increase in the number of proerythroblasts and shortens the time required for full RBC maturation. After approximately 120 days, since the RBC do not contain a nucleus or any other regenerative capabilities, the cells are removed from circulation by either the phagocytic activities of macrophages in the liver, spleen and lymph nodes (~90%) or by hemolysis in the plasma (~10%). Following macrophage engulfment, chemical components of the RBC are broken down within vacuoles of the macrophages due to the action of lysosomal enzymes.

"Secretory tissues" are those tissues in an animal that secrete products out of the individual cell into a lumen of some type which are typically derived from epithelium. Examples of secretory tissues that are localized to the gastrointestinal tract include the cells that line the gut, the pancreas, and the gallbladder. Other secretory tissues include the liver, tissues associated with the eye and mucous membranes such as salivary glands, mammary glands, the prostate gland, the pituitary gland and other members of the endocrine system. Additionally, secretory tissues include individual cells of a tissue type which are capable of secretion.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a Cas DNA-binding domain is fused to an activation domain, the Cas DNA-binding domain and the activation domain are in operative linkage if, in the fusion polypeptide, the Cas DNA-binding domain portion is able to bind its target site and/or its binding site, while the activation domain is able to up-regulate gene expression. When a fusion polypeptide in which a Cas DNA-binding domain is fused to a cleavage domain, the Cas DNA-binding domain and the cleavage domain are in operative linkage if, in the fusion polypeptide, the Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the or stem cells of the invention can be administered. Subjects of the present invention include those that have been exposed to one or more chemical toxins, including, for example, a nerve toxin.

The CRISPR/Cas System

Compelling evidence has recently emerged for the existence of an RNA-mediated genome defense pathway in archaea and many bacteria that has been hypothesized to parallel the eukaryotic RNAi pathway (for reviews, see Godde and Bickerton, 2006. *J. Mol. Evol.* 62: 718-729; Lillestol et al., 2006. *Archaea* 2: 59-72; Makarova et al., 2006. *Biol. Direct* 1: 7; Sorek et al., 2008. *Nat. Rev. Microbiol.* 6: 181-186). Known as the CRISPR-Cas system or prokaryotic RNAi (pRNAi), the pathway is proposed to arise from two evolutionarily and often physically linked gene loci: the CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60). CRISPR loci in microbial hosts contain a combination of CRISPR-associated (Cas) genes as well as non-coding RNA elements capable of programming the specificity of the CRISPR-mediated nucleic acid cleavage. The individual Cas proteins do not share significant sequence similarity with protein components of the eukaryotic RNAi machinery, but have analogous predicted functions (e.g., RNA binding, nuclease, helicase, etc.) (Makarova et al., 2006. *Biol. Direct* 1: 7). The CRISPR-associated (cas) genes are often associated with CRISPR repeat-spacer arrays. More than forty different Cas protein families have been described. Of these protein families, Cas1 appears to be ubiquitous among different CRISPR/Cas systems. Particular combinations of cas genes and repeat structures have been used to define 8 CRISPR subtypes (Ecoli, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

The Type II CRISPR, initially described in *S. pyogenes*, is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences where processing occurs by a double strand-specific RNase III in the presence of the Cas9 protein. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. In addition, the tracrRNA must also be present as it base pairs with the crRNA at its 3' end, and this association triggers Cas9 activity. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien nucleic acid. Thus, in the bacterial cell, several of the so-called 'Os' proteins are involved with the natural function of the CRISPR/Cas system.

Type II CRISPR systems have been found in many different bacteria. BLAST searches on publically available genomes by Fonfara et al ((2013) *Nuc Acid Res* 42(4):2377-2590) found Cas9 orthologs in 347 species of bacteria. Additionally, this group demonstrated in vitro CRISPR/Cas cleavage of a DNA target using Cas9 orthologs from *S. pyogenes, S. mutans, S. therophilus, C. jejuni, N. meningitides, P. multocida* and *F. novicida*. Thus, the term "Cas9" refers to an RNA guided DNA nuclease comprising a DNA binding domain and two nuclease domains, where the gene encoding the Cas9 may be derived from any suitable bacteria. The sequence of *S. pyogenes* Cas9 is shown below (see, also, UniProtKB/Swiss-Prot: Q99ZW2.1 and Nishimasu et al. (2014) *Cell* 156(5):9325-949):

```
                                                            (SEQ ID NO: 2)
   1 mdkkysigld igtnsvgwav itdeykvpsk kfkvlgntdr hsikknliga llfdsgetae 61 atrlkrtarr rytrrknric ylqeifsnem akvddsffhr leesflveed kkherhpifg 121 nivdevayhe kyptiyhlrk klvdstdkad lrliylalah mikfrghfli egdlnpdnsd 181 vdklfiqlvq tynqlfeenp inasgvdaka ilsarlsksr rlenliaqlp gekknglfgn 241 lialslgltp nfksnfdlae daklqlskdt ydddldnlla qigdqyadlf laaknlsdai 301 llsdilrvnt eitkaplsas mikrydehhq dltllkalvr qqlpekykei ffdqskngya 361 gyidggasqe efykfikpil ekmdgteell vklnredllr kqrtfdngsi phqihlgelh 421 ailrrqedfy pflkdnreki ekiltfripy yvgplargns rfawmtrkse etitpwnfee 481 vvdkgasaqs fiermtnfdk nlpnekvlpk hsllyeyftv yneltkvkyv tegmrkpafl 541 sgeqkkaivd llfktnrkvt vkqlkedyfk kiecfdsvei sgvedrfnas lgtyhdllki 601 ikdkdfldne enedilediv ltltlfedre mieerlktya hlfddkvmkq lkrrrytgwg 661 rlsrklingi rdkqsgktil dflksdgfan rnfmqlihdd sltfkediqk aqvsgqgdsl 721 hehianlags paikkgilqt vkvvdelvkv mgrhkpeniv iemarenqtt qkgqknsrer 781 mkrieegike lgsqilkehp ventqlqnek lylyylqngr dmyvdqeldi nrlsdydvdh 841 ivpqsflkdd sidnkvltrs dknrgksdnv pseevvkkmk nywrqllnak litqrkfdnl 901 tkaergglse ldkagfikrq lvetrqitkh vaqildsrmn tkydendkli revkvitlks 961 klvsdfrkdf qfykvreinn yhhandayln avvgtalikk ypklesefvy gdykvydvrk 1021 miakseqeig katakyffys nimnffktei tlangeirkr plietngetg eivwdkgrdf
```

-continued

```
1081 atvrkvlsmp qvnivkktev qtggfskesi lpkrnsdkli arkkdwdpkk yggfdsptva 1141 ysvlvvakve kgkskklksv kellgitime rssfeknpid fleakgykev kkdliiklpk 1201 yslfelengr krmlasagel qkgnelalps kyvnflylas hyeklkgspe dneqkqlfve 1261 qhkhyldeii eqisefskry iladanldkv lsaynkhrdk pireqaenii hlftltnlga 1321 paafkyfdtt idrkrytstk evldatlihq sitglyetri dlsqlggd
```

The Cas9 protein includes a recognition lobe that is involved in binding sgRNA and DNA and a nuclease lobe that includes a domain involved in interaction with the PAM sequence. See, e.g., Nishimasu et al. (2014) Cell 156(5): 9325-949). The Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand. The Cas 9 nuclease can be engineered such that only one of the nuclease domains is functional, creating a Cas nickase (see Jinek et al, ibid). Nickases can be generated by specific mutation of amino acids in the catalytic domain of the enzyme, or by truncation of part or all of the domain such that it is no longer functional. Since Cas 9 comprises two nuclease domains, this approach may be taken on either domain. A double strand break can be achieved in the target DNA by the use of two such Cas 9 nickases. The nickases will each cleave one strand of the DNA and the use of two will create a double strand break.

The primary products of the CRISPR loci appear to be short RNAs that contain the invader targeting sequences, and are termed guide RNAs or prokaryotic silencing RNAs (psiRNAs) based on their hypothesized role in the pathway (Makarova et al., 2006. Biol. Direct 1: 7; Hale et al., 2008. RNA, 14: 2572-2579). RNA analysis indicates that CRISPR locus transcripts are cleaved within the repeat sequences to release 60- to 70-nt RNA intermediates that contain individual invader targeting sequences and flanking repeat fragments (Tang et al. 2002. Proc. Natl. Acad. Sci. 99: 7536-7541; Tang et al., 2005. Mol. Microbiol. 55: 469-481; Lillestol et al. 2006. Archaea 2: 59-72; Brouns et al. 2008. Science 321: 960-964; Hale et al, 2008. RNA, 14: 2572-2579). In the archaeon Pyrococcus furiosus, these intermediate RNAs are further processed to abundant, stable 35- to 45-nt mature psiRNAs (Hale et al. 2008. RNA, 14: 2572-2579). The requirement of the crRNA-tracrRNA complex can be avoided by use of an engineered "single-guide RNA" (sgRNA) that comprises the hairpin normally formed by the annealing of the crRNA and the tracrRNA (see Jinek et al (2012) Science 337:816 and Cong et al (2013) Sciencexpress/10.1126/science.1231143). In S. pyogenes, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing (see Ramalingam ibid) and has been useful for zebrafish embryo genomic editing in vivo (see Hwang et al (2013) Nature Biotechnology 31 (3):227) with editing efficiencies similar to ZFNs and TALENs.

The Cas9 protein from S. pyogenes has been crystallized in association with its guide RNA and target DNA (Nishimesu et al (2014) Cell 156(5): 935-949). This study confirmed that the PAM-interacting (PI) residues in Cas9 are found within the so-called recognition lobe (REC) of the protein. The PI location appears to be residues 1099-1368 of the protein and is suggested to recognize the PAM sequence on the non-complementary DNA strand in the target region. The work also included the swapping of PI domains from S. pyogenes and S. thermophilus, resulting in a chimeric Cas9 protein that was able to recognize PAM sequences specific to the identity of the PI sequence rather than the rest of the Cas9 protein. In addition, deletion of the PI domain all together resulted in Cas9 proteins devoid of activity, demonstrating that PI domain is essential for Cas9 function.

Other Cas Proteins

"Cas1" polypeptide refers to CRISPR associated (Cas) protein1. Cas1 (COG1518 in the Clusters of Orthologous Group of proteins classification system) is the best marker of the CRISPR-associated systems (CASS). Based on phylogenetic comparisons, seven distinct versions of the CRISPR-associated immune system have been identified (CASS1-7).

Cas1 polypeptide used in the methods described herein can be any Cas1 polypeptide present in any prokaryote. In certain embodiments, a Cas1 polypeptide is a Cas1 polypeptide of an archaeal microorganism. In certain embodiments, a Cas1 polypeptide is a Cas1 polypeptide of a Euryarchaeota microorganism. In certain embodiments, a Cas1 polypeptide is a Cas1 polypeptide of a Crenarchaeota microorganism. In certain embodiments, a Cas1 polypeptide is a Cas1 polypeptide of a bacterium. In certain embodiments, a Cas1 polypeptide is a Cas1 polypeptide of a gram negative or gram positive bacteria. In certain embodiments, a Cas1 polypeptide is a Cas1 polypeptide of Pseudomonas aeruginosa. In certain embodiments, a Cas1 polypeptide is a Cas1 polypeptide of Aquifex aeolicus. In certain embodiments, a Cas1 polypeptide is a Cas1 polypeptide that is a member of one of CASS1-7. In certain embodiments, Cas1 polypeptide is a Cas1 polypeptide that is a member of CASS3. In certain embodiments, a Cas1 polypeptide is a Cas1 polypeptide that is a member of CASS7. In certain embodiments, a Cas1 polypeptide is a Cas1 polypeptide that is a member of CASS3 or CASS7.

In some embodiments, a Cas1 polypeptide is encoded by a nucleotide sequence provided in GenBank at, e.g., GeneID number: 2781520, 1006874, 9001811, 947228, 3169280, 2650014, 1175302, 3993120, 4380485, 906625, 3165126, 905808, 1454460, 1445886, 1485099, 4274010, 888506, 3169526, 997745, 897836, or 1193018 and/or an amino acid sequence exhibiting homology (e.g., greater than 80%, 90 to 99% including 91%, 92%, 93%, 94%, 95%, 96%, 97%, 98% or 99%) to the amino acids encoded by these polynucleotides and which polypeptides function as Cas1 polypeptides.

Cas6 is another Cas polypeptide, and the endoribonuclease activity is referred to herein as Cas6 endoribonuclease activity. Non-limiting examples of suitable Cas6 polypeptides are depicted at Genbank Accession No. AAL81255. A Cas6 polypeptide may be enriched, isolated, or purified from a microbe having a CRISPR locus and the cas (CRISPR-associated) locus, such as, but not limited to, *Pyrococcus furiosus*, or may be produced using recombinant techniques, or chemically or enzymatically synthesized using routine methods. In some aspects, a Cas6 polypeptide may be enriched, isolated, or purified from a microbe that does not have CRISPR loci. A Cas6 polypeptide may include a GhGxxxxxGhG (SEQ ID NO:1) motif (where "h" indicates a hydrophobic amino acid) near the C-terminus. An Arg or Lys may be, and often is, found within the central stretch of 5 amino acids. A Cas6 polypeptide contains at least one residue that may play a role in catalysis, or conservative substitution thereof. A Cas6 polypeptide may contain other residues which may also play a role in catalysis, or conservative substitution thereof. The residue(s) expected to play a role in catalysis may be located near the G-rich loop that contains the Cas6 signature motif in the 3D structure of the protein. Cas6 polypeptides may include domains present in the TIGRFAM database at accession numbers TIGR01877 and PF01881. The TIGRFAM database includes families of polypeptides for which function is conserved (Haft et al., *Nucl. Acids Res.*, 2003, 31:371-373, Bateman and Haft, 2002, *Briefings Bioinformatics*, 3:236-245, and Haft et al., 2005, *PLoS Computational Biol.*, 1(6):e60).

Other examples of Cas6 polypeptides provided herein include those present in prokaryotic microbes having a CRISPR locus and a cas locus. Cas6 polypeptides can be easily identified in any microbe that includes a CRISPR locus. A coding region encoding a Cas6 polypeptide is typically in a cas locus located in close proximity to a CRISPR locus. Haft et al. (2005, *PLoS Computational Biol.*, 1(6):e60) review the Cas protein family, and created rules for the identification of specific subtypes of the CRISPR/Cas system. Haft et al describe the coding region encoding Cas6 polypeptides as being found in association with at least four separate CRISPR/Cas subtypes (Tneap, Hmari, Apern, and Mtube), and as typically being the cas coding region located most distal to the CRISPR locus. Cas6 polypeptides may be identified using the resources available at the JCVI Comprehensive Microbial Resource. Thus, Cas6 polypeptides that are useful in the methods described herein can be identified by the skilled person using routine methods.

Examples of prokaryotic microbes with known whole genomic sequences containing coding regions expected to encode a Cas6 polypeptide include Thermotoga *maritima* MSB8, *Campylobacter fetus* subsp. fetus 82-40, *Fusobacterium nucleatum* ATCC 25586, *Streptococcus thermophilus* LMG 18311, *Thermoanaerobacter tengcongensis* MB4(T), *Moorella* thermoacetica ATCC 39073, Desulfitobacterium hafniense Y51, *Clostridium tetani* E88, *Clostridium perfringens* SM101, *Clostridium difficile* QCD-32g58, *Clostridium botulinum* Hall A Sanger, *Clostridium botulinum* F Langeland, *Clostridium botulinum* B1 strain Okra, *Clostridium botulinum* A3 strain Loch Maree, *Clostridium botulinum* A Hall, *Clostridium botulinum* A ATCC 19397, *Carboxydothermus* hydrogenoformans Z-2901, Staphylococcus epidermidis RP62A, *Thermus thermophilus* HB8, *Thermus thermophilus* HB27, *Nostoc* sp. PCC 7120, *Anabaena variabilis* ATCC 29413, *Synechococccus* sp. OS Type B prime, *Synechococccus* sp. OS Type A, *Porphyromonas gingivalis* W83, *Bacteroides fragilis* YCH46, *Bacteroides fragilis* NCTC9343, *Aquifex aeolicus* VF5, *Rubrobacter xylanophilus* DSM 9941, *Mycobacterium tuberculosis* H37Rv (lab strain), *Mycobacterium tuberculosis* CDC1551, *Mycobacterium bovis* subsp. bovis ΔF2122/97, *Frankia alni* ACN14a, *Thermoplasma volcanium* GSS1, *Picrophilus torridus* DSM 9790, *Thermococcus kodakarensis* KOD1, *Pyrococcus horikoshii shinkaj* OT3, *Pyrococcus furiosus* DSM 3638, *Pyrococcus abyssi* GES, *Methanosarcina barkeri fusaro*, *Methanosarcina acetivorans* C2A, *Methanococcoides burtonii* DSM 6242, *Methanococcus jannaschii* DSM2661, *Methanobacterium thermoautotrophicum* delta H, *Haloarcula marismortui* ATCC 43049, *Archaeoglobus fulgidus* DSM4304, *Pyrobaculum aerophilum* 1M2, *Sulfolobus tokodaii* strain 7, *Sulfolobus solfataricus* P2, *Sulfolobus acidocaldarius* DSM 639, *Aeropyrum pernix* K1. Other examples of Cas6 polypeptides are known to the skilled person, see, for instance, members of the COG1583 group of polypeptides (available at the Clusters of Orthologous Groups of proteins (COGs) web page through the National Center for Biotechnology Information internet site, see also Tatusov et al., (1997), *Science*, 278:631-637, and Tatusov et al. (2003), *BMC Bioinformatics*, 4(1):41), members of the InterPro family having accession number IPRO10156, Makarova et al., (2002), *Nuc. Acids Res.*, 30:482-496 and Haft et al. (2005), *PLoS Comput. Biol.*, 1(6):e60, 474-483).

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. In some aspects, a functional derivative may comprise a single biological property of a naturally occurring Cas protein. In other aspects, a function derivative may comprise a subset of biological properties of a naturally occurring Cas protein.

"Cas1 polypeptide" encompasses a full-length Cas polypeptide, an enzymatically active fragment of a Cas polypeptide, and enzymatically active derivatives of a Cas polypeptide or fragment thereof. Suitable derivatives of a Cas polypeptide or a fragment thereof include but are not limited to mutants, fusions, covalent modifications of Cas protein or a fragment thereof. Cas protein which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

The CRISPR/Cas system can also be used to inhibit gene expression. Lei et al (see, (2013) *Cell*, 152, (5): 1173-1183) have shown that a catalytically dead Cas9 lacking endonuclease activity, when co-expressed with a guide RNA, generates a DNA recognition complex that can specifically interfere with transcriptional elongation, RNA polymerase binding, or transcription factor binding. This system, called CRISPR interference (CRISPRi), can efficiently repress expression of targeted genes.

The Cas proteins of the invention may be mutated to alter functionality. Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; DNA-binding domains and methods for design and construction of fusion proteins (and polynucleotides encoding same) are known to those of skill in the art and described in detail in U.S. Pat. Nos. 8,586,526; 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

B. Functional Domains

The systems described herein can include any suitable functional domain that associates with the single guide RNA to act on the target gene. Non-limiting examples of functional domains include transcriptional activation domains, transcriptional repression domains and/or nuclease domains. See, e.g., U.S. Pat. Nos. 6,534,261; and 8,409,861.

In certain embodiments, the functional domain comprises one or more cleavage domains. The functional domain (e.g., cleavage domain) may be heterologous to the DNA-binding domain, for example a functional domain that is heterologous to the single-guide RNA of the CRISPR/Cas system. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains. In some embodiments, a Cas protein may be linked to a heterologous nuclease domain. In some aspects, the Cas protein is a Cas9 protein devoid of nuclease activity linked to a FokI nuclease domain such that double strand cleavage is dependent on dimerization of the FokI nuclease domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 7,914,796; 8,034,598; and 8,623,618, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055, incorporated by reference herein). In still further embodiments, the engineered cleavage half-domain comprises mutations at positions 487 and 496 (numbered relative to wild-type FokI), for instance mutations that replace the wild-type Arg (R) residue at position 487 with an Asp (D) residue and the wild-type Asn (N) residue at position 496 with an Asp (D) residue (also referred to as "DD") and/or mutations at positions 483 and 537 (numbered relative to wild-type FokI), for instance, mutations that replace the wild-type Asp (D) residue at position 483 with an Arg (R) residue and the wild-type His (H) residue at position 537 with an Arg (R) residue (also referred to as "RR"). In other embodiments, the engineered cleavage half-domain comprises mutations at positions 487, 499 and 496 (numbered relative to wild-type FokI), for instance mutations that replace the wild-type Arg (R) residue at position 487 with an Asp (D) residue and the wild-type Ile (I) residue at position 499 with an Ala (A) and the wild-type Asn (N) residue at position 496 with an Asp (D) residue (also referred to as "DAD") and/or mutations at positions 483, 538 and 537 (numbered relative to wild-type FokI), for instance, mutations that replace the wild-type Asp (D) residue at position 483 with an Arg (R) residue and the wild-type Ile (I) residue at position 538 with a Val (V) residue, and the wild-type His (H) residue at position 537 with an Arg (R) residue (also referred to as "RVR").

In another aspect, the engineered cleavage half domains may be further engineered to contain mutations in domain of the FokI other than the dimerization domain. For example, mutations at positions 418, 432, 441, 481, 523, 527 and 559 have been shown to increase the catalytic activity of a wild-type Fok I domain. In particular, the mutations where Pro (P) replaces the wild-type Ser (S) residue at position 418 and where a Glu (E) residue replaces the wild-type Lys (K) residue at position 441 (known as "PE", also known as "Sharkey") have been shown to enhance catalytic activity (see Guo et al (2010) *J. Mol Biol*, doi:10.101b/j.jmb.2010.04.060). In another aspect, the mutations where Pro (P) replaces the wild-type Ser (S) at position 418, where Leu (L) replaces the wild-type Phe (F) at position 432, where Glu (E) replaces the wild-type Lys (K) at position 441, where His (H) replaces the wild-type Gln (Q) at position 481, where Tyr (Y) replaces the wild-type His (H) at position 523, where Asp (D) replaces the wild-type Asn (N) at position 527 and Gln (Q) replaces the wild-type Lys (K) at position 559 (known as "Sharkey", see Guo et al, ibid). Thus in one embodiment, the mutant FokI domain may comprise mutations at positions 418, 441, 486, and 499. In another embodiment, the mutant FokI domain may comprise mutations at positions 418, 441, 490, and 538. In further embodiments, the wild-type FokI domain may be mutated to include mutations at positions 418, 441, 486, 496 and 499, and/or 418, 441, 490, 537, and 538. In other embodiments, the wild-type FokI domain may be mutated at positions 418, 432, 441, 481, 486, 496, 499 523, 527 and 559 and/or positions 418, 432, 441, 481, 523, 527, 559, 490, 538 and 537. In particular, the mutations may include mutation of the wild-type Gln (Q) at position 486 with Glu (E), mutation of the wild-type Ile (I) at position 499 with a Leu (L), mutation of the wild-type Asn (N) at position 496 with an Asp (D), mutation of the wild-type Ser (S) at position 418 with a Pro (P) and mutation of the wild-type Lys (K) at position 441 with a Glu (E) (also known as "ELD-S" or "ELD Sharkey") and/or mutation of the wild-type Glu (E) at position 490 with a Lys (K), mutation of the wild-type Ile (I) at position 538 with a Lys (K), mutation of the wild-type His (H) at position 537 with an Lys (K) or Arg(R), mutation of the wild-type Ser (S) at position 418 with a Pro (P) and mutation of the wild-type Lys (K) at position 441 with a Glu (E) residue (also known as KKK-S or KKR-S, or KKK-Sharkey or KKR-Sharkey). Further embodiments encompass S418P: F432L:K441E:Q481H:Q486E:N496D:I499L:H523Y: N527D:K559Q, also known as ELD-Sharkey', and S418P: F432L:K441E:Q481H:E490K:H523Y:N527D:H537K or R:I538K:K559Q, also known as KKK-Sharkey' or KKR-Sharkey'.

Engineered cleavage half-domains described herein can be prepared using any suitable method, for example, by site-directed mutagenesis of wild-type cleavage half-domains (Fok I).

Alternatively, nucleases may be assembled in vivo at the nucleic acid target site using so-called "split-enzyme" technology (see, e.g., U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain. Further, inducible dimerization domains (e.g. the rapamycin dimerization domain) can be fused to each partner of the split enzyme to allow for controlled reassembly of the nuclease (see Zetsche et al (2015), *Nature Biotechnology* 33(2):139).

In yet another aspect, cells comprising any of the polypeptides (e.g., fusion polypeptides) and/or polynucleotides as described herein are also provided. In one embodiment, the cells comprise a pair of fusion polypeptides, one fusion polypeptide comprising an ELD or ELE cleavage half-domain and one fusion polypeptide comprising a KKK or KKR cleavage half-domain. In another embodiment, one fusion polypeptide comprises a DAD cleavage half domain while another comprises the RVR fusion polypeptide. In other embodiments, the paired fusion polypeptides further comprise mutations in other locations of the FokI nuclease domain. In some embodiments, these catalytic domain mutants are S418P and K441E, thus these mutant fusion polypeptides comprise the mutant FokI domains listed below:

(a) EL-S: S418P:K441E:Q486E:I499L
(b) KK-S: S418P:K441E:E490K:I538K
(c) ELD-S: S418P:K441E:Q486E:N496D:I499L
(d) KKK-S: S418P:K441E:E490K:H537K:I538K
(e) KKR-S: S418P:K441E:E490K:H537R:I538K
(f) DA-S: S418P:K441E:R487D:I499A
(g) RV-S: S418P:K441E:D483R:I538V
(h) DAD-S: S418P:K441E:R487D:N496D:I499A
(i) RVR-S: S418P:K441E:D483R:H537R:I538V
(j) DD-S: S418P:K441E:R487D:N496D
(k) RR-S: S418P:K441E:D483R:H537R

Nucleases can be screened for activity prior to use, for example in a yeast-based chromosomal system as described in U.S. Pat. No. 8,563,314. Nuclease expression constructs can be readily designed using methods known in the art. Expression of the nuclease may be under the control of a constitutive promoter or an inducible promoter, for example the galactokinase promoter which is activated (de-repressed) in the presence of raffinose and/or galactose and repressed in presence of glucose.

RNA Components of CRISPR/Cas

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) Sciencexpress 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek ibid and Cong, ibid).

Chimeric or sgRNAs can be engineered to comprise a sequence complementary to any desired target. The RNAs comprise 22 bases of complementarity to a target and of the form G[n19], followed by a protospacer-adjacent motif (PAM) of the form NGG. Thus, in one method, sgRNAs can be designed by utilization of a known ZFN target in a gene of interest by (i) aligning the recognition sequence of the ZFN heterodimer with the reference sequence of the relevant genome (human, mouse, or of a particular plant species); (ii) identifying the spacer region between the ZFN half-sites; (iii) identifying the location of the motif G[N20]GG that is closest to the spacer region (when more than one such motif overlaps the spacer, the motif that is centered relative to the spacer is chosen); (iv) using that motif as the core of the sgRNA. This method advantageously relies on proven nuclease targets. Alternatively, sgRNAs can be designed to target any region of interest simply by identifying a suitable target sequence the conforms to the G[n20]GG formula. Along with the complementarity region, an sgRNA may comprise additional nucleotides to extend to tail region of the tracrRNA portion of the sgRNA (see Hsu et al (2013) Nature Biotech doi:10.1038/nbt.2647). Tails may be of +67 to +85 nucleotides, or any number therebetween with a preferred length of +85 nucleotides. Truncated sgRNAs may also be used, "tru-gRNAs" (see Fu et al, (2014) Nature Biotech 32(3): 279). In tru-gRNAs, the complementarity region is diminished to 17 or 18 nucleotides in length.

Further, alternative PAM sequences may also be utilized, where a PAM sequence can be NAG as an alternative to NGG (Hsu 2014, ibid) using a S. pyogenes Cas9. Additional PAM sequences may also include those lacking the initial G (Sander and Joung (2014) Nature Biotech 32(4):347). In addition to the S. pyogenes encoded Cas9 PAM sequences, other PAM sequences can be used that are specific for Cas9 proteins from other bacterial sources. For example, the PAM sequences shown below (adapted from Sander and Joung, ibid, and Esvelt et al, (2013) Nat Meth 10(11):1116) are specific for these Cas9 proteins:

| Species | PAM |
| --- | --- |
| S. pyogenes | NGG |
| S. pyogenes | NAG |
| S. mutans | NGG |
| S. thermophilius | NGGNG |
| S. thermophilius | NNAAAW |
| S. thermophilius | NNAGAA |
| S. thermophilius | NNNGATT |
| C. jejuni | NNNNACA |
| N. meningitides | NNNNGATT |
| P. multocida | GNNNCNNA |
| F. novicida | NG |

Thus, a suitable target sequence for use with a S. pyogenes CRISPR/Cas system can be chosen according to the following guideline: [n17, n18, n19, or n20](G/A)G. Alternatively the PAM sequence can follow the guideline G[n17, n18, n19, n20](G/A)G. For Cas9 proteins derived from non-S. pyogenes bacteria, the same guidelines may be used where the alternate PAMs are substituted in for the S. pyogenes PAM sequences.

Most preferred is to choose a target sequence with the highest likelihood of specificity that avoids potential off target sequences. These undesired off target sequences can be identified by considering the following attributes: i) similarity in the target sequence that is followed by a PAM sequence known to function with the Cas9 protein being utilized; ii) a similar target sequence with fewer than three mismatches from the desired target sequence; iii) a similar target sequence as in ii), where the mismatches are all located in the PAM distal region rather than the PAM proximal region (there is some evidence that nucleotides 1-5 immediately adjacent or proximal to the PAM, sometimes referred to as the 'seed' region (Wu et al (2014) Nature Biotech doi:10.1038/nbt2889) are the most critical for recognition, so putative off target sites with mismatches located in the seed region may be the least likely be recognized by the sg RNA); and iv) a similar target sequence where the mismatches are not consecutively spaced or are spaced greater than four nucleotides apart (Hsu 2014, ibid). Thus, by performing an analysis of the number of potential off target sites in a genome for whichever CRIPSR/Cas system is being employed, using these criteria above, a suitable target sequence for the sgRNA may be identified.

Alternatively, novel PAM sequences and novel PI domains can be identified by the methods and compositions of the invention. For example, mutations can be generated in the C-terminal domain are present to alter PAM interaction. In some aspects, mutations can be generated in the Cas9 protein between amino acids 1099 to 1368 or 1200 to 1368 (or anywhere therebetween). In some embodiments, the Cas9 protein can comprise an altered tryptophan containing loop at amino acids 447-502, or at the tryptophan containing loop 1102-1137. In further embodiments, the Cas9 protein can comprise alterations in both the 447-50 and 1102-1137 loops such that an altered DNA PAM site recognition occurs. In some embodiments, mutations are made in the Cas9 protein between residues 1099-1368 or 1200-1368 and are paired with guide RNAs with altered PAM sequences to identify novel and functional sets of PI domains and PAMs on guide RNAs. These novel PI domain/PAMs are useful for increasing the density of recognition sites for the Cas9 protein, allowing an increased choice of target location.

Donors

As noted above, insertion of an exogenous sequence (also called a "donor sequence" or "donor" or "transgene"), for example for correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest. Alternatively, a donor may have no regions of homology to the targeted location in the DNA and may be integrated by NHEJ-dependent end joining following cleavage at the target site. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded and/or double-stranded and can be introduced into a cell in linear or circular form. See, e.g., U.S. Patent Publication Nos. 20100047805 and 20110207221. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the endogenous gene into which the donor is inserted (e.g., globin, AAVS1, etc.). However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. In other embodiments, the transgene (e.g., with or without globin encoding sequences) is integrated into any endogenous locus, for example a safe-harbor locus. See, e.g., US patent publications 20080299580; 20080159996 and 201000218264.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the CRISPR/Cas system(s). Any vector systems may be used including, but not limited to, plasmid vectors, DNA minicircles, retroviral vectors, lentiviral vectors, adenovirus vectors, poxvirus vectors; herpesvirus vectors and adeno-associated virus vectors, etc., and combinations thereof. See, also, U.S. Pat. Nos. 6,534,261; 6,607,882; 6,824,978; 6,933,113; 6,979,539; 7,013,219; and 7,163,824, and U.S. Patent Publication No. 20140335063, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, DNA minicircles, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, naked RNA, capped RNA, artificial virions, and agent-enhanced uptake of DNA.

Sonoporation using, e.g., the Sonitron 2000 system (RichMar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) Nature Biotechnology 27(7):643).

The use of RNA or DNA viral based systems for the delivery of nucleic acids encoding engineered CRISPR/Cas systems take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., J. Virol. 66:2731-2739 (1992); Johann et al., J. Virol. 66:1635-1640 (1992); Sommerfelt et al., Virol. 176:58-59 (1990); Wilson et al., J. Virol. 63:2374-2378 (1989); Miller et al., J. Virol. 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., Blood 85:3048-305 (1995); Kohn et al., Nat. Med. 1:1017-102 (1995); Malech et al., PNAS 94:22 12133-12138 (1997)). PA317/pLASN was the first therapeutic vector used in a gene therapy trial. (Blaese et al., Science 270:475-480 (1995)). Transduction efficiencies of 50% or greater have been observed for MFG-S packaged vectors. (Ellem et al., Immunol Immunother. 44(1):10-20 (1997); Dranoff et al., Hum. Gene Ther. 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 base pair (bp) inverted terminal repeats flanking the transgene expression cassette. Efficient gene transfer and stable transgene delivery due to integration into the genomes of the transduced cell are key features for this vector system. (Wagner et al., Lancet 351:9117 1702-3 (1998), Kearns et al., Gene Ther. 9:748-55 (1996)). Other AAV serotypes, including AAV1, AAV3, AAV4, AAV5, AAV6, AAV8, AAV9 and AAVrh10, and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., Hum. Gene Ther. 7:1083-9 (1998)). Additional examples of the use of adenovirus vectors for gene transfer in clinical trials include Rosenecker et al., Infection 24:1 5-10 (1996); Sterman et al., Hum. Gene Ther. 9:7 1083-1089 (1998); Welsh et al., Hum.

*Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, a donor polynucleotide can be carried by a plasmid, while the one or more nucleases can be carried by a AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

The nucleases of the invention can also be delivered as purified polypeptides. The nucleases can also be delivered as protein:guide RNA complexes using the purified polypeptide in combination in in vitro transcribed guide RNAs (see Kim et al (2014) *Gen Res* 24(6):1012).

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Plant Delivery

As noted above, DNA and/or RNA may be introduced into (e.g., into the genome of) a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9. See, also, U.S. Patent Publication Nos. 20090205083; 20100199389; 20110167521 and 20110189775, incorporated herein by reference in their entireties.

For example, polynucleotides may be introduced directly into the genomic DNA of the plant cell using techniques such as electroporation and microinjection of plant cell protoplasts, or the polynucleotides can be introduced directly to plant tissue using biolistic methods, such as DNA particle bombardment (see, e.g., Klein et al. (1987) *Nature* 327:70-73). Alternatively, the polynucleotide(s) can be introduced into the plant cell via nanoparticle transformation (see, e.g., U.S. Patent Publication No. 20090104700, which is incorporated herein by reference in its entirety). Alternatively, the DNA/RNA constructs may be combined with suitable T-DNA border/flanking regions and introduced into a conventional *Agrobacterium tumefaciens* host vector. *Agrobacterium tumefaciens*-mediated transformation techniques, including disarming of oncogenes and the development and use of binary vectors, are well described in the scientific literature. See, for example Horsch et al. (1984) *Science* 233:496-498, and Fraley et al. (1983) *Proc. Nat'l. Acad. Sci. USA* 80:4803.

In addition, gene transfer may be achieved using non-*Agrobacterium* bacteria or viruses such as *Rhizobium* sp. NGR234, *Sinorhizoboium meliloti, Mesorhizobium loti,* potato virus X, cauliflower mosaic virus and cassava vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of a T-strand containing the construct and adjacent marker into the plant cell DNA when the cell is infected by the bacteria using binary T-DNA vector (Bevan (1984) *Nuc. Acid Res.* 12:8711-8721) or the co-cultivation procedure (Horsch et al. (1985) *Science* 227: 1229-1231). Generally, the *Agrobacterium* transformation system is used to engineer dicotyledonous plants (Bevan et al. (1982) *Ann. Rev. Genet* 16:357-384; Rogers et al. (1986) *Methods Enzymol.* 118:627-641). The *Agrobacterium* transformation system may also be used to transform, as well as transfer, polynucleotides to monocotyledonous plants and plant cells. See U.S. Pat. No. 5,591,616; Hernalsteen et al. (1984) *EMBO J* 3:3039-3041; Hooykass-Van Slogteren et al. (1984) *Nature* 311:763-764; Grimsley et al. (1987) *Nature* 325:1677-179; Boulton et al. (1989) *Plant Mol. Biol.* 12:31-40; and Gould et al. (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA/RNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide (e.g., WHISKERS™) mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture,* pp. 124-176, Macmillian Publishing Company, New York, 1983; and Binding, *Regeneration of Plants, Plant Protoplasts,* pp. 21-73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna,* and *Zea.*

The introduction of nucleic acids introduced into a plant cell can be used to confer desired traits on essentially any plant. In certain embodiments, the altered MDH expression/function in plant cells results in plants having increased amount of fruit yield, increased biomass of plant (or fruit of the plant), higher content of fruit flesh, concentrated fruit set, larger plants, increased fresh weight, increased dry weight, increased solids context, higher total weight at harvest, enhanced intensity and/or uniformity of color of the crop, altered chemical (e.g., oil, fatty acid, carbohydrate, protein) characteristics, etc.

One with skill in the art will recognize that an exogenous sequence can be transiently incorporated into a plant cell. The introduction of an exogenous polynucleotide sequence can utilize the cell machinery of the plant cell in which the sequence has been introduced. The expression of an exogenous polynucleotide sequence comprising a Cas that is transiently incorporated into a plant cell can be assayed by analyzing the genomic DNA of the target sequence to identify and determine any indels, inversions, or insertions. These types of rearrangements result from the cleavage of the target site within the genomic DNA sequence, and the subsequent DNA repair. In addition, the expression of an exogenous polynucleotide sequence can be assayed using methods which allow for the testing of marker gene expression known to those of ordinary skill in the art. Transient expression of marker genes has been reported using a variety of plants, tissues, and DNA delivery systems. Transient analyses systems include but are not limited to direct gene delivery via electoporation or particle bombardment of tissues in any transient plant assay using any plant species of interest. Such transient systems would include but are not limited to electroporation of protoplasts from a variety of tissue sources or particle bombardment of specific tissues of interest. The present disclosure encompasses the use of any transient expression system to evaluate a site specific endo-nuclease (e.g., CRISPR/Cas system) and to introduce mutations within an MDH target gene. Examples of plant tissues envisioned to test in transients via an appropriate delivery system would include but are not limited to leaf base tissues, callus, cotyledons, roots, endosperm, embryos, floral tissue, pollen, and epidermal tissue.

One of skill in the art will recognize that an exogenous polynucleotide sequence can be stably incorporated in transgenic plants. Once the exogenous polynucleotide sequence is confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing stably inserted gene constructs, or plant cell containing target gene altered genomic DNA which results from the transient expression of a site-specific endonuclease (e.g., CRISPR/Cas system). These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-1 and PAT proteins using an ELISA assay is described in U.S. Patent Publication No. 20090093366, which reference is hereby incorporated by reference in its entirety herein. A transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

Fusion proteins (e.g., Cas nucleases) and expression vectors encoding fusion proteins can be administered directly to the plant for gene regulation, targeted cleavage, and/or recombination. In certain embodiments, the plant contains multiple paralogous MDH target genes. Thus, one or more different fusion proteins or expression vectors encoding fusion proteins may be administered to a plant in order to target one or more of these paralogous genes in the plant.

Administration of effective amounts is by any of the routes normally used for introducing fusion proteins into ultimate contact with the plant cell to be treated. The ZFPs are administered in any suitable manner, preferably with acceptable carriers. Suitable methods of administering such modulators are available and well known to those of skill in the art, and, although more than one route can be used to administer a particular composition, a particular route can often provide a more immediate and more effective reaction than another route.

Carriers may also be used and are determined in part by the particular composition being administered, as well as by the particular method used to administer the composition. Accordingly, there is a wide variety of suitable formulations of carriers that are available.

EXAMPLES

Example 1: Designing of sgRNAs

The sequence of the guide RNA (sgRNA or gRNA) for use in genome editing of a given ZFN-specified locus was identified by: (i) aligning the recognition sequence of the ZFN heterodimer with the reference sequence of the relevant genome (human, mouse, or of a particular plant species); (ii) identifying the spacer region between the ZFN half-sites; (iii) identifying the location of the motif G[N20]GG that is closest to the spacer region (when more than one such motif overlapped the spacer, the motif that is centered relative to the spacer was chosen); (iv) using that motif as the core of the gRNA. Exemplary sgRNAs for use in generating genetically modified cells using a CRISPR/Cas system are described for example in U.S. Publication No. 20140335063.

Example 2: sgRNAs and Tru-RNAs to Genes of Interest

As described in Example 1, the design of an sgRNA is accomplished through a variety of considerations: (i) aligning the recognition sequence of the ZFN heterodimer with the reference sequence of the relevant genome (human, mouse, or of a particular plant species); (ii) identifying the spacer region between the ZFN half-sites; (iii) identifying the location of the PAM motif relevant to the Cas9 protein being used (for example: G[N17-20](G/A)G when using the *S. pyogenes* Cas9) that is closest to the spacer region (when more than one such motif overlapped the spacer, the motif that is centered relative to the spacer was chosen); (iv) using that motif as the core of the sgRNA.

Shown below in Table 1 are exemplary genes for targeting with a CRISPR/Cas system and an sgRNA of the invention. Also indicated is an accession number of representative example of a cDNA associated with these genes.

TABLE 1

Exemplary genes for targeting with a CRISPR/Cas system

| Gene name | UCSC Genome Brower location | Representative Accession (cDNA) RefSeq |
|---|---|---|
| HBB | chr11: 5246696-5248301 | (NM_000518) |
| BCL11A | chr2: 60684329-60780633 | (NM_022893) |
| KLF1 | chr19: 12995237-12998017 | (NM_006563) |
| HBG1 | chr11: 5269502-5271087 | (NM_000559) |
| CCR5 | chr3: 46411633-46417697 | (NM_000579) |
| CXCR4 | chr2: 136871919-136873813 | (NM_001008540) |
| PPP1R12C | chr19: 55602281-55628968 | (NM_017607) |
| HPRT | chrX: 133594175-133634698 | (NM_000194) |
| Mouse HPRT | chrX: 52988078-53021660 (assembly GRCm38/mm10) | (NM_013556) |
| ALB | chr4: 74269972-74287129 | (NM_000477) |
| Factor VIII | chrX: 154064064-154250998 | (NM_000132.3) |
| Factor IX | chrX: 138612895-138645617 | (NM_000133) |
| LRRK2 | chr12: 40618813-40763086 | (NM_198578) |
| Htt | chr4: 3076237-3245687 | (NM_002111) |
| RHO | chr3: 129247482-129254187 | (NM_000539) |
| CFTR | chr7: 117120017-117308718 | (NM_000492) |
| TCRA | chr6: 42883727-42893575 | (NM_001243168) |
| TCRB | chr7: 142197572-142198055 | L36092.2 |
| PD-1 | chr2: 242792033-242795132 | (NM_005018) |
| CTLA-4 | chr2: 204732511-204738683 | (NM_001037631) |
| HLA-A | chr6: 29910247-29912868 | (NM_002116) |
| HLA-B | chr6: 31236526-31239913 | NM_005514.6 |
| HLA-C | chr6: 31236526-31239125 | (NM_001243042) |
| HLA-DPA | chr6: 33032346-33048555 | (NM_033554.3) |
| HLA-DQ | chr6: 32605183-32611429 | (NM_002122) |
| HLA-DRA | chr6_ssto_hap7: 3754283-3759493 | (NM_019111) |
| LMP7 | chr6_dbb_hap3: 4089872-4093057 | (X66401) |
| Tapasin | chr6: 33271410-33282164 | (NM_172208) |
| RFX5 | chr1: 151313116-151319769 | (NM_001025603) |
| CIITA | chr16: 10971055-11002744 | (NM_000246) |
| TAP1 | chr6: 32812986-32821748 | (NM_000593) |
| TAP2 | chr6: 32793187-32806547 | (NM_000544) |
| TAPBP | chr6: 33267472-33282164 | |
| DMD | chrX: 31137345-33229673 | (NM_004006) |
| RFX5 | chr1: 151313116-151319769 | (NM_000449) |
| MAPT | chr17: 43971748-44105699 | NM_001123066.3 |
| ApoE | Chr 19: 45409039-45412650 | NM_000041.2 (gene, promoter = DQ286969) |
| SCNA | chr4: 90,645,250-90,759,447 | NM_001146055.1 |
| PSEN1 | chr14: 73,603,143-73,690,399 | (NM_000021) |
| PSEN2 | chr1: 227,058,273-227,083,804 | (NM_000447) |
| SLC6A4 | chr17: 28521337-28562986 | (NM_001045) |
| CACNA1C | chr12: 2,080,229-2,080,366 | NC_000012.11 |
| CACNB2 | chr10: 18429606-18830688 | NM_201596 |
| DMPK | chr19: 46272976-46285815 | NM_001081560 |
| CACNA1A | chr19: 13317256-13617274 | NM_001127222 |
| ATP1A2 | chr1: 160,085,520-160,113,374 | NM_000702 |
| FXN | chr9: 71650479-71693993 | (NM_181425) |
| PMP22 | chr17: 15,133,096-15,165,889 | NM_153322 |
| C9orf72 | chr9: 27546543-27573491 | NM_018325 |
| SOD1 | chr21: 33,031,935-33,041,243 | (NM_000454) |
| TARDBP | chr1: 11,072,679-11,085,549 | (NM_007375) |
| FUS | chr16: 31,191,431-31,206,192 | (NR_028388) |
| ANG | chr14: 21,152,336-21,162,345 | (NM_001145) |
| ALS2 | chr2: 202,564,986-202,645,895 | (NM_020919) |
| SETX | chr9: 135,136,827-135,230,372 | (NM_015046) |
| GRN | chr17: 42,422,491-42,430,470 | (NM_002087) |
| VAPB | chr20: 56,964,175-57,026,156 | (NM_001195677) |
| FMR1 | chrX: 146,993,469-147,032,647 | NM_001185075.1 |
| MECP2 | chrX: 153,287,264-153,363,188 | (NM_001110792) |
| ASPA | chr17: 3,379,296-3,402,700 | NM_001128085.1 |
| SMN1 | chr5: 70,220,768-70,247,953 | (NM_000344) |
| UGT1A1 | chr2: 234,668,919-234,680,261 | (NM_000463) |
| OPRM1 | chr6: 154,360,443-154,440,594 | (NM_000914) |
| OPRK1 | chr8: 54,138,276-54,164,194 | NM_001282904.1 |
| OPRD1 | chr1: 29,138,654-29,190,208 | NM_000911.3 |
| SLC6A4 | chr17: 28,521,337-28,562,986 | NM_001045.5 |
| HTR2a | chr13: 47,405,677-47,471,211 | NM_001165947.2 |
| TPH2 | chr12: 72,332,626-72,426,221 | NM_173353.3 |
| DRD2 | chr11: 113,280,317-113,346,001 | NM_000795.3 |
| GRM3 | chr7: 86,273,230-86,494,192 | (NM_000840) |

TABLE 1-continued

Exemplary genes for targeting with a CRISPR/Cas system

| Gene name | UCSC Genome Brower location | Representative Accession (cDNA) RefSeq |
|---|---|---|
| GRIN2A | chr16: 9,847,265-10,276,263 | NM_001134408.2 |
| SRR | chr17: 2,207,248-2,228,553 | NM_001304803.1 |
| GRIA1 | chr5: 152,871,732-153,193,429 | NM_001258020.1 |
| CACNB2 | chr10: 18,429,606-18,830,688 | NM_201593.2 |
| GAD1 | chr2: 171,673,200-171,717,659 | NM_013445.3 |
| RELN | chr7: 103,112,231-103,629,963 | NM_173054.2 |
| BDNF | chr11: 27,676,442-27,722,600 | NM_170731.4 |
| PRDM16 | chr1: 2,985,742-3,355,185 | NM_199454.2 |
| AJAP1 | chr1: 4,715,105-4,843,851 | NM_018836.3 |
| MEF2D | chr1: 156,433,513-156,470,634 | NM_001271629.1 |
| TRPM8 | chr2: 234,826,043-234,928,166 | NM_024080.4 |
| TGFBR2 | chr3: 30,647,994-30,735,633 | NM_001024847.2 |
| PHACTR1 | chr6: 12,717,037-13,288,075 | NM_001242648.1 |
| MMP16 | chr8: 89,049,460-89,339,717 | NM_005941.4 |
| ASTN2 | chr9: 119,187,504-120,177,317 | NM_014010.4 |
| TSPAN2 | chr1: 115,590,633-115,632,121 | NM_001308315.1 |
| GFRA2 | chr8: 21,549,530-21,646,346 | NM_001165039.1 |
| LRP1 | chr12: 57,522,282-57,607,125 | NM_002332.2 |
| IL7Ra | chr5: 35,856,977-35,879,705 | NM_002185.3 |
| IL2Ra | chr10: 6,052,657-6,104,333 | NM_001308242.1 |
| CYP27Ba | chr12: 58,156,117-58,160,976 | NM_000785.3 |
| TYK2 | chr19: 10,461,204-10,491,248 | NM_003331.4 |
| NRXN1 | chr2: 50,145,643-51,259,674 | NM_004801.4 |
| AADAC | chr3: 151,531,861-151,546,276 | NM_001086.2 |
| CTNNA3 | chr10: 67,679,725-69,455,949 | (NM_013266) |
| FSCB | chr14: 44,973,354-44,976,499 | NM_032135.3 |
| RCAN1 | chr21: 35,888,784-35,987,382 | NM_004414.6 |
| NMDA R1 (NARG2) | chr15: 60,711,808-60,771,359 | NM_001018089.2 |
| GAD65 | chr10: 26,505,236-26,590,048 | NM_000818.2 |
| IGF1 | chr12: 102,811,454-102,874,378 | NM_001111284.1 |
| Neuropeptide Y | chr7: 24,323,807-24,331,484 | NM_000905.3 |
| PMP22 | chr17: 15133094-15165906 | (NM_153321) |
| Utrophin | chr6: 144612899-145174267 | (NM_001278561) |
| C9ORF72 | chr9: 27546543-27573864 | (NM_001256054) |
| FMR1 | chrX: 146993469-147032647 | (NM_002024) |
| DMPK | chr19: 46272967-46285815 | (NM_001081563) |
| FXN | chr9: 71650479-71693993 | (NM_000144) |
| *B. napus* FAD3 | See PCT publication WO2014/039684 | JN992612 |
| *B. napus* FAD2 | See PCT publication WO2014/039692 | JN992609 |
| Soybean FAD2 | See US20140090116 | |
| *Zea mays* ZP15 | See U.S. Pat. No. 8,329,986 | GBWI-61522 (MaizeCyc) |
| B-ketoacyl ACP synthase II (KASII) | See U.S. Pat. No. 8,592,645 | |
| Tomato MDH | See US 20130326725 | AY725474 |
| *B. napus* EPSPS paralogs C + D | See U.S. Pat. No. 8,399,218 | |
| Paralog D | See U.S. Pat. No. 8,399,218 | |
| Paralog A + B | See U.S. Pat. No. 8,399,218 | |
| PPP1R12C (AAVS1) | chr19: 55602840-55624858 | (NM_017607) |
| GR | 5: 142646254-142783254 | (NM_000176) |
| IL2RG | chrX: 70327254-70331481 | (NM_000206) |
| SFTPB | chr2: 85884440-85895374 | (NM_198843) |

Single-guide RNAs are then introduced into cells along with polynucleotides encoding one or more functional domains, and optionally donor sequences, for modification of the target gene.

Example 3: Construction of Cas9-FokI Fusion Proteins and Appropriate Guide RNAs

For cleavage at a single target site, fusion proteins comprising the nuclease defective *S. pyogenes* Cas9 (spCas9) DNA interaction domains are fused to obligate heterodimeric FokI nuclease domains. Thus, the fusion proteins comprise nuclease defective spCas9 linked to ELD FokI (nuc⁻spCas9-ELD) and nuclease defective spCas9 linked to KKR FokI (nuc-spCas9-KKR).

Alternatively, a first fusion protein is generated by fusing the ELD variant of the FokI cleavage domain to a catalytically inactive version of Cas9 from *S. pyogenes*: nuc⁻spCas9-ELD as described above (also Tsai (2014) ibid) and a second fusion protein is generated by fusing the KKR variant of the FokI cleavage domain to a catalytically inactive version of Cas9 from *Neisseria meningitidis*: nuc⁻nmCas9-KKR. A compatible guide RNA is created for the first fusion protein based on the strategy described in Tsai (2014) and U.S. Publication No. 20140335063 that targets a region in the human CCR5 gene. A compatible guide RNA for the second fusion protein based on the strategy described in Esvelt et al., (ibid) that targets a region of the human CCR5 gene adjacent to the locus targeted by the guide RNA for the first fusion protein. Guide RNAs designed for use with *S. pyogenes* Cas9 do not function with *Neisseria meningitidis* Cas9 because the relevant PAM sequence will not be present in the target sequence and guide RNAs designed for use with *Neisseria meningitidis* Cas9 do not function with *S. pyrogenes* Cas9 (Esvelt et al., ibid). The ELD FokI variant cannot dimerize with another copy of the ELD FokI variant and the KKR FokI variant cannot dimerize with another copy of the KKR FokI variant so DNA cleavage only occurs at genomic loci comprising the proper PAM sequences, where the guide RNA compatible with *S. pyrogenes* Cas9 and the guide RNA compatible with *Neisseria meningitidis* Cas9 target adjacent DNA sequences. Utilizing either wild type FokI in such fusions or catalytically active Cas9 proteins allows for undesired DNA cleavage at genomic loci targeted by two adjacent copies of a single type of guideRNA-Cas9 complex.

To cleave two target sites A and B in a genome, orthogonal mutant pairs of the Fok I domain are utilized. The fusion proteins that are described above are utilized to cleave target site A, where specific guide RNAs are used to target sequences comprising the correct PAM with their specific half of the pair (i.e., nuc⁻spCas9-ELD and nuc⁻nmCas9-KKR). A second pair is then used to cleave site B utilizing Cas9 proteins from other bacterial species (i.e. *S. thermophilius* Cas9-DAD FokI and *C. jejuni* Cas9-RVR FokI) also using guide RNAs that target the site B comprising the correct PAM sequences. Cells are contacted with the four different Cas9-Fok fusion proteins and the guide RNAs specific for the targeted sites A and B that comprise the correct PAM sequences, and the targets A and B are cleaved. Alternatively, cells are contacted with the fusion protein-guide RNA complexes and the targets are cleaved.

Example 4: Activity of Cas9-FokI Fusion Proteins

The fusion proteins from Example 3 are then tested in vitro and in vivo for nuclease activity. Fusion protein pairs are transfected into K562 cells as per standard protocols and nuclease activity is analyzed as described previously (see The Cel-I assay (Surveyor™, Transgenomics) as described in Perez et al. (2008) *Nat. Biotechnol.* 26: 808-816 and Guschin et al. (2010) *Methods Mol Biol.* 649:247-56). Additionally, the regions flanking the cleavage site are sequences using the MiSeq platform (Illumina) and the data reveal that the fusion proteins are active and highly specific.

Example 5: Alteration of PAM Recognition and Development of New PAM Sequences

To alter the PAM recognition characteristics of a Cas9 protein, mutations are made in the C-terminal region of Cas9. Random mutations in Cas9, specifically the *S. pyogenes* protein, targeting the region encoding amino acids 1099 to 1368 or 1200 to 1368 are generated. For example, this region is subcloned from the complete sequence into another plasmid. This plasmid is then subject to error-prone PCR to introduce random and unbiased mutations across this sequence. The mutagenized sequences are then cloned back into the holo Cas9 sequence in expression vectors as a library such that all mutagenized Cas9 sequences are expressed.

All different DNA targets are made to test a variety of PAM sequences that might interact with the mutated *S. pyogenes* Cas9 proteins using a given guide RNA in a cleavage reporter assay. For example, the wild type PAM sequence is 5'-NGG or 5'-NAG. Thus, target DNA sequences are constructed in the reporter vector such that the 14 artificial PAMs (e.g. 5'NAA, 5'NAC, 5'NAG (wild-type), 5'NAT, 5'NCA, 5'NCC, 5'NCG, 5'NCT, 5'NGA, 5'NGC, 5'NGG (wild-type), 5'NGT, 5'NTA, 5'NTC, 5'NTG, and 5'NTT) are placed adjacent to where the guide RNA would interact.

To explore the sequence preference for spCas9, a modified version of the GUIDE-seq procedure (Tsai et al, (2015) *Nature Biotechnology* 33, 187-197) was used. We used the CRISPR for the "T1" target of the hAAVS1 locus sequence chr19 55627142 (see FIG. 2 of Mali et al. (2013) *Science*, 339:823-826, 2013) and performed the analysis in K562 cells according to standard protocols. The genome target is 5'-GTCCCCTCCACCCCACAGTGGGG (SEQ ID NO:3) where the PAM is indicated in bold. Off target cleavage sites would be expected to resemble 5'-GTCCCCTCCAC-CCCACAGTGNGG (SEQ ID NO:4). 50 off target sites were identified using MiSeq analysis. The off targets and their locations are indicated in Table 2 below.

TABLE 2

Off target locations for the AAVS1-specific Cas9

| Chromosome | genome coordinate |
|---|---|
| chr9 | 133925238 |
| chr1 | 20451093 |
| chr4 | 108975650 |
| chr19 | 18608992 |
| chr17 | 18869247 |
| chr19 | 12146195 |
| chr14 | 34255211 |
| chr22 | 20132146 |
| chrX | 49066566 |
| chr14 | 50065751 |
| chr22 | 47199173 |
| chr7 | 28909356 |
| chr16 | 53089703 |
| chr14 | 85911487 |
| chr3 | 38031636 |
| chr3 | 135393333 |
| chr10 | 80231183 |
| chr3 | 43297464 |
| chr22 | 21365114 |
| chr13 | 26830044 |
| chr1 | 200866435 |
| chr11 | 134810931 |
| chr12 | 106198754 |
| chr13 | 113778869 |
| chr6 | 13862824 |
| chr16 | 85147424 |
| chr2 | 52660705 |
| chr19 | 13171201 |
| chr5 | 177032658 |
| chrX | 8623723 |
| chr3 | 52261960 |
| chr13 | 110166648 |
| chr1 | 34494934 |
| chr12 | 8524541 |
| chr11 | 134810931 |
| chr17 | 40951373 |
| chr18 | 45316719 |
| chr1 | 42757452* |
| chr15 | 78487071 |
| chr3 | 48607995 |
| chr13 | 23682499 |
| chr2 | 73516827 |
| chr3 | 4880119 |
| chr2 | 75299810 |
| chr6 | 3229546 |
| chr16 | 1037769 |
| chr5 | 131202333 |
| chr3 | 17205680** |
| chr11 | 3292514 |
| chr22 | 45467777 |

*1 bp deletion
*1 bp insertion

The 48 off target sites that did not have insertions or deletions relative to the guide RNA were then aligned to determine the preference for each base in comparison with the expected target sequence. The results are shown below in Table 3 where the bolding in the table indicated the preference for the base above that expected by chance, and the target sequence (SEQ ID NO:4) is shown across the top in a 5' to 3' orientation.

TABLE 3

Base preference for a known target sequence

| | | Known Target sequence | | | | | | | | | | | | | | | | | | | | | | |
|---|---|---|---|---|---|---|---|---|---|---|---|---|---|---|---|---|---|---|---|---|---|---|---|---|
| | | G | T | C | C | C | T | C | C | A | C | C | C | A | C | A | G | T | G | N | G | G | | |
| A | 9 | 12 | 6 | 2 | 2 | 3 | 2 | 6 | 4 | 4 | 35 | 2 | 1 | 0 | 1 | 46 | 0 | 47 | 3 | 5 | 5 | 14 | 7 | 3 | 7 | 11 |
| C | 13 | 11 | 16 | 36 | 41 | 43 | 44 | 15 | 41 | 37 | 8 | 44 | 45 | 46 | 47 | 1 | 47 | 1 | 0 | 6 | 3 | 4 | 0 | 0 | 24 | 12 |
| G | 11 | 19 | 4 | 6 | 0 | 0 | 1 | 0 | 1 | 1 | 2 | 0 | 0 | 0 | 0 | 1 | 0 | 0 | 45 | 5 | 38 | 15 | 41 | 45 | 12 | 12 |
| T | 15 | 6 | 22 | 4 | 5 | 2 | 1 | 27 | 2 | 6 | 3 | 2 | 2 | 2 | 0 | 0 | 1 | 0 | 0 | 32 | 2 | 15 | 0 | 0 | 5 | 13 |

The data in Table 3 indicates that the CRISPR/Cas9 complex has a preference for a "C" immediately 3' of the known PAM.

Additional target DNA sequences to test if specificity can be added at positions adjacent to the two bases specified by S. pyogenes Cas9 are also constructed and tested (e.g. 5'AGG, 5'CGG, 5'GGG, 5'TGG, 5'NGGA, 5'NGGC, 5'NGGG, and 5'NGGT).

The reporter assay used to select the mutants of interest is a cleavage based assay. Briefly, bacteria are transformed with the Cas9-mutant encoding plasmid library (expression of the Cas9 is driven by the arabinose inducible promoter) and a plasmid (pTox) that expresses the bacterial ccdB toxin from the T7 promoter where the toxin encoding sequence includes nuclease targets site comprising one of each of the 10 possible PAMs adjacent to a sequence that is antisense to the guide RNA. This system allows the ability to query libraries of mutant Cas9 proteins (mCas9) and novel PAM sequences to identify unique and functional combinations of mCas9s and novel PAMs.

The expressed and functional mCas9-PAM combinations, in the presence of the guide RNA, cleave pTox leading to degradation of the pTox plasmid. Non-functional mCas9-PAM combinations do not cleave pTox and the ccdB toxin is expressed, resulting in cell killing. Expression and target plasmids from the survivor colonies (Cas-cleaved pTox) are amplified and the genes encoding the novel mCas9 and PAM sequence re-cloned into new plasmids for sequence analysis.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A Cas polypeptide comprising a *S. pyogenes* Cas 9 (spCas9) protein, wherein the Cas polypeptide that forms a complex with a single guide RNA (sgRNA) that binds to a target sequence in an endogenous gene, the target sequence comprising a protospacer adjacent motif (PAM) sequence of 5'VGGC (i.e. 5' AGGC, CGGC or GGGC) at the 3' end of the target sequence, wherein the complex exhibits increased binding specificity to and cleavage of the target sequence by the Cas/sgRNA complex as compared to a target sequence comprising a PAM sequence of NGGD (i.e. 5' NGGA, NGGG or NGGT).

2. The Cas polypeptide of claim 1, wherein the spCas9 polypeptide is a mutant spCas9 protein and the mutations are in the α-helical lobe of the Cas9 protein.

3. The Cas polypeptide of claim 2, wherein the mutations are in the region of the Cas9 protein extending between amino acid 78 to amino acid 718 of SEQ ID NO:2.

4. The Cas polypeptide of claim 2, wherein the mutations are in the C-terminal domain of the Cas polypeptide.

5. The Cas polypeptide of claim 4, wherein the mutations are between amino acids 1099 to 1368 or 1200 to 1368 of SEQ ID NO:2.

6. The Cas polypeptide of claim 2, wherein the mutation is in an altered tryptophan containing loop between amino acids 447-502 or 1102-1137 of SEQ ID NO:2.

7. A complex comprising the Cas polypeptide associated with the sgRNA of claim 1 and the target sequence in the endogenous gene.

8. The complex of claim 7, wherein the target sequence is in an endogenous safe harbor gene.

9. A method of cleaving a target sequence in a cell, the method comprising generating a complex of claim 7 into the cell such that the target is cleaved.

10. A cell comprising a cleaved target made by the method of claim 9.

* * * * *

SEQUENCE LISTING

```
<160> NUMBER OF SEQ ID NOS: 4

<210> SEQ ID NO 1
<211> LENGTH: 11
<212> TYPE: PRT
<213> ORGANISM: Unknown
<220> FEATURE:
<223> OTHER INFORMATION: Description of Unknown: Cas6 peptide motif
<220> FEATURE:
<221> NAME/KEY: MOD_RES
<222> LOCATION: (2)..(2)
<223> OTHER INFORMATION: Any hydrophobic amino acid
<220> FEATURE:
<221> NAME/KEY: MOD_RES
<222> LOCATION: (4)..(8)
<223> OTHER INFORMATION: Any amino acid
<220> FEATURE:
<221> NAME/KEY: MOD_RES
<222> LOCATION: (10)..(10)
<223> OTHER INFORMATION: Any hydrophobic amino acid

<400> SEQUENCE: 1

Gly Xaa Gly Xaa Xaa Xaa Xaa Xaa Gly Xaa Gly
1               5                   10

<210> SEQ ID NO 2
<211> LENGTH: 1368
<212> TYPE: PRT
<213> ORGANISM: Streptococcus pyogenes
```

```
<400> SEQUENCE: 2

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415
```

-continued

```
Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830
```

```
Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
            1010                1015                1020

Lys Ser Glu Gln Glu Ile Gly Lys Ala Thr Ala Lys Tyr Phe Phe
            1025                1030                1035

Tyr Ser Asn Ile Met Asn Phe Phe Lys Thr Glu Ile Thr Leu Ala
            1040                1045                1050

Asn Gly Glu Ile Arg Lys Arg Pro Leu Ile Glu Thr Asn Gly Glu
            1055                1060                1065

Thr Gly Glu Ile Val Trp Asp Lys Gly Arg Asp Phe Ala Thr Val
            1070                1075                1080

Arg Lys Val Leu Ser Met Pro Gln Val Asn Ile Val Lys Lys Thr
            1085                1090                1095

Glu Val Gln Thr Gly Gly Phe Ser Lys Glu Ser Ile Leu Pro Lys
            1100                1105                1110

Arg Asn Ser Asp Lys Leu Ile Ala Arg Lys Lys Asp Trp Asp Pro
            1115                1120                1125

Lys Lys Tyr Gly Gly Phe Asp Ser Pro Thr Val Ala Tyr Ser Val
            1130                1135                1140

Leu Val Val Ala Lys Val Glu Lys Gly Lys Ser Lys Lys Leu Lys
            1145                1150                1155

Ser Val Lys Glu Leu Leu Gly Ile Thr Ile Met Glu Arg Ser Ser
            1160                1165                1170

Phe Glu Lys Asn Pro Ile Asp Phe Leu Glu Ala Lys Gly Tyr Lys
            1175                1180                1185

Glu Val Lys Lys Asp Leu Ile Ile Lys Leu Pro Lys Tyr Ser Leu
            1190                1195                1200

Phe Glu Leu Glu Asn Gly Arg Lys Arg Met Leu Ala Ser Ala Gly
            1205                1210                1215

Glu Leu Gln Lys Gly Asn Glu Leu Ala Leu Pro Ser Lys Tyr Val
            1220                1225                1230

Asn Phe Leu Tyr Leu Ala Ser His Tyr Glu Lys Leu Lys Gly Ser
```

-continued

```
                    1235                    1240                    1245
Pro  Glu  Asp  Asn  Glu  Gln  Lys  Gln  Leu  Phe  Val  Glu  Gln  His  Lys
     1250                    1255                    1260

His  Tyr  Leu  Asp  Glu  Ile  Ile  Glu  Gln  Ile  Ser  Glu  Phe  Ser  Lys
     1265                    1270                    1275

Arg  Val  Ile  Leu  Ala  Asp  Ala  Asn  Leu  Asp  Lys  Val  Leu  Ser  Ala
     1280                    1285                    1290

Tyr  Asn  Lys  His  Arg  Asp  Lys  Pro  Ile  Arg  Glu  Gln  Ala  Glu  Asn
     1295                    1300                    1305

Ile  Ile  His  Leu  Phe  Thr  Leu  Thr  Asn  Leu  Gly  Ala  Pro  Ala  Ala
     1310                    1315                    1320

Phe  Lys  Tyr  Phe  Asp  Thr  Thr  Ile  Asp  Arg  Lys  Arg  Tyr  Thr  Ser
     1325                    1330                    1335

Thr  Lys  Glu  Val  Leu  Asp  Ala  Thr  Leu  Ile  His  Gln  Ser  Ile  Thr
     1340                    1345                    1350

Gly  Leu  Tyr  Glu  Thr  Arg  Ile  Asp  Leu  Ser  Gln  Leu  Gly  Gly  Asp
     1355                    1360                    1365

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtcccctcca ccccacagtg ggg                                              23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 4
gtcccctcca ccccacagtg ngg                                              23
```